(12) United States Patent
Xiao et al.

(10) Patent No.: US 11,597,721 B2
(45) Date of Patent: Mar. 7, 2023

(54) HETEROCYCLIC COMPOUNDS COMPRISING PYRIDINE USEFUL AS MODULATORS OF IL-12, IL-23 AND/OR IFNα RESPONSES

(71) Applicant: BRISTOL-MYERS SQUIBB COMPANY, Princeton, NJ (US)

(72) Inventors: Zili Xiao, East Windsor, NJ (US); Michael G. Yang, Narberth, PA (US); Chunjian C. Liu, Pennington, NJ (US); Trevor C. Sherwood, West Windsor, NJ (US); John L. Gilmore, Yardley, PA (US); David S. Weinstein, San Diego, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 113 days.

(21) Appl. No.: 16/982,937

(22) PCT Filed: Mar. 20, 2019

(86) PCT No.: PCT/US2019/023111
§ 371 (c)(1),
(2) Date: Sep. 21, 2020

(87) PCT Pub. No.: WO2019/183186
PCT Pub. Date: Sep. 26, 2019

(65) Prior Publication Data
US 2021/0032220 A1    Feb. 4, 2021

Related U.S. Application Data

(60) Provisional application No. 62/646,432, filed on Mar. 22, 2018.

(51) Int. Cl.
| | | |
|---|---|---|
| *C07D 401/14* | (2006.01) | |
| *C07D 413/14* | (2006.01) | |
| *C07D 417/14* | (2006.01) | |
| *C07D 513/04* | (2006.01) | |

(52) U.S. Cl.
CPC ......... *C07D 401/14* (2013.01); *C07D 413/14* (2013.01); *C07D 417/14* (2013.01); *C07D 513/04* (2013.01)

(58) Field of Classification Search
CPC .. C07D 413/14; C07D 413/00; C07D 401/14; C07D 417/14; C07D 417/00; C07D 513/04
USPC ...................................................... 514/236.2
See application file for complete search history.

(56) References Cited

U.S. PATENT DOCUMENTS

2013/0178478 A1   7/2013  Hermann et al.
2015/0299183 A1   10/2015 Moslin et al.

FOREIGN PATENT DOCUMENTS

WO    13052393 A1    4/2013

OTHER PUBLICATIONS

Liao et al. Arthritis Research & Therapy (2013), 15(5), R146/1-R146/14, 14 pp.*
U.S. Appl. No. 14/441,193, filed May 7, 2015, U.S. Pat. No. 9,315,494.
PCT/US2013/068842, Filing date: Nov. 7, 2013, Published Publication No. WO2014/074660.
U.S. Appl. No. 14/441,213, filed May 7, 2015, U.S. Pat. No. 9,540,333.
PCT/US2013/068866, Filing date: Nov. 7, 2013, Published Publication No. WO2014/074670.
U.S. Appl. No. 14/441,183, filed May 7, 2015, U.S. Pat. No. 9,505,748.
U.S. Appl. No. 15/289,437, filed Oct. 10, 2016, U.S. Pat. No. 10,000,480.
U.S. Appl. No. 15/979,770, filed May 15, 2018, U.S. Pat. No. 10,526,321.
U.S. Appl. No. 16/687,279, filed Nov. 18, 2019, Published Publication No. US20200071315A1.
U.S. Appl. No. 16/201,653, filed Nov. 27, 2018, U.S. Pat. No. RE47929.
PCT/US2013/068846, Filing date: Nov. 7, 2013, Published Publication No. WO2014/074661.
U.S. Appl. No. 15/034,915, filed May 6, 2016, U.S. Pat. No. 9,663,467.
U.S. Appl. No. 15/480,787, filed Apr. 6, 2017, U.S. Pat. No. 9,987,266.

(Continued)

*Primary Examiner* — Kahsay Habte
(74) *Attorney, Agent, or Firm* — Elliott Korsen

(57) ABSTRACT

Compounds having the following formula (I) or a stereoisomer or pharmaceutically-acceptable salt thereof, where $R^1, R^2, R^3, R^4$, and $R^5$ are as defined herein, are useful in the modulation of IL-12, IL-23 and/or IFNα, by acting on Tyk-2 to cause signal transduction inhibition.

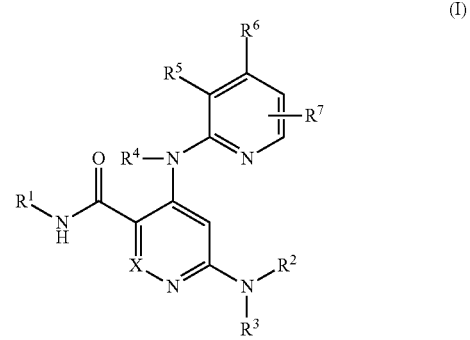

(I)

11 Claims, No Drawings

(56) References Cited

OTHER PUBLICATIONS

PCT/US2014/011769, Filing date: Jan. 31, 2020, Published Publication No. WO2018/111787.
U.S. Appl. No. 15/838,434, filed Dec. 12, 2017, U.S. Pat. No. 10,294,256.
PCT/US2017/065665, Filing date: Dec. 12, 2017, Published Publication No. WO2018/111787.
U.S. Appl. No. 16/195,951, filed Nov. 20, 2018, Filed.
PCT/US2018/061726, Filing date: Nov. 19, 2018, Published Publication No. WO2019/103952.
PCT/US2020/015291, Filing date: Jan. 28, 2020, Published Publication No. WO2020/159904.
PCT/US2019/058268, Filing date: Oct. 28, 2019, Published Publication No. WO2020/092196.
U.S. Appl. No. 63/016,539, filed Apr. 28, 2020, Filed.

\* cited by examiner

HETEROCYCLIC COMPOUNDS COMPRISING PYRIDINE USEFUL AS MODULATORS OF IL-12, IL-23 AND/OR IFNα RESPONSES

CROSS-REFERENCE TO RELATED APPLICATIONS

This application is a national phase application under 35 U.S.C. § 371 of International Patent Application No. PCT/US2019/023111, filed Mar. 20, 2019, which claims priority to U.S. Provisional Application Ser. 62/646,432, filed Mar. 22, 2018, the contents of which are specifically incorporated fully herein by reference.

FIELD OF THE INVENTION

This invention relates to compounds useful in the modulation of IL-12, IL-23 and/or IFNα by acting on Tyk-2 to cause signal transduction inhibition. Provided herein are amide-substituted heterocyclic compounds, compositions comprising such compounds, and methods of their use. The invention further pertains to pharmaceutical compositions containing at least one compound according to the invention that are useful for the treatment of conditions related to the modulation of IL-12, IL-23 and/or IFNα in a mammal.

BACKGROUND OF THE INVENTION

The heterodimeric cytokines interleukin (IL)-12 and IL-23, which share a common p40 subunit, are produced by activated antigen-presenting cells and are critical in the differentiation and proliferation of Th1 and Th17 cells, two effector T cell lineages which play key roles in autoimmunity. IL-23 is composed of the p40 subunit along with a unique p19 subunit. IL-23, acting through a heterodimeric receptor composed of IL-23R and IL-12Rβ1, is essential for the survival and expansion of Th17 cells which produce pro-inflammatory cytokines such as IL-17A, IL-17F, IL-6 and TNF-α (McGeachy, M. J. et al., "The link between IL-23 and Th17 cell-mediated immune pathologies", Semin. Immunol., 19:372-376 (2007)). These cytokines are critical in mediating the pathobiology of a number of autoimmune diseases, including rheumatoid arthritis, multiple sclerosis, inflammatory bowel disease, and lupus. IL-12, in addition to the p40 subunit in common with IL-23, contains a p35 subunit and acts through a heterodimeric receptor composed of IL-12Rβ1 and IL-12Rβ2. IL-12 is essential for Th1 cell development and secretion of IFNγ, a cytokine which plays a critical role in immunity by stimulating MHC expression, class switching of B cells to IgG subclasses, and the activation of macrophages (Gracie, J. A. et al., "Interleukin-12 induces interferon-gamma-dependent switching of IgG alloantibody subclass", Eur. J. Immunol., 26:1217-1221 (1996); Schroder, K. et al., "Interferon-gamma: an overview of signals, mechanisms and functions", J. Leukoc. Biol., 75(2):163-189 (2004)).

The importance of the p40-containing cytokines in autoimmunity is demonstrated by the discovery that mice deficient in either p40, p19, or IL-23R are protected from disease in models of multiple sclerosis, rheumatoid arthritis, inflammatory bowel disease, lupus and psoriasis, among others (Kyttaris, V. C. et al., "Cutting edge: IL-23 receptor deficiency prevents the development of lupus nephritis in C57BL/6-lpr/lpr mice", J. Immunol., 184:4605-4609 (2010); Hong, K. et al., "IL-12, independently of IFN-gamma, plays a crucial role in the pathogenesis of a murine psoriasis like skin disorder", J. Immunol., 162:7480-7491 (1999); Hue, S. et al., "Interleukin-23 drives innate and T cell-mediated intestinal inflammation", J. Exp. Med., 203:2473-2483 (2006); Cua, D. J. et al., "Interleukin-23 rather than interleukin-12 is the critical cytokine for autoimmune inflammation of the brain", Nature, 421:744-748 (2003): Murphy, C. A. et al., "Divergent pro- and anti-inflammatory roles for IL-23 and IL-12 in joint autoimmune inflammation", J. Exp. Med., 198:1951-1957 (2003)).

In human disease, high expression of p40 and p19 has been measured in psoriatic lesions, and Th17 cells have been identified in active lesions in the brain from MS patients and in the gut mucosa of patients with active Crohn's disease (Lee, E. et al., "Increased expression of interleukin 23 p19 and p40 in lesional skin of patients with psoriasis vulgaris", J. Exp. Med., 199:125-130 (2004); Tzartos, J. S. et al., "Interleukin-17 production in central nervous system infiltrating T cells and glial cells is associated with active disease in multiple sclerosis", Am. J. Pathol., 172:146-155 (2008)). The mRNA levels of p19, p40, and p35 in active SLE patients were also shown to be significantly higher compared with those in inactive SLE patients (Huang, X. et al., "Dysregulated expression of interleukin-23 and interleukin-12 subunits in systemic lupus erythematosus patients", Mod. Rheumatol., 17:220-223 (2007)), and T cells from lupus patients have a predominant Th1 phenotype (Tucci, M. et al., "Overexpression of interleukin-12 and T helper 1 predominance in lupus nephritis", Clin. Exp. Immunol., 154:247-254 (2008)).

Moreover, genome-wide association studies have identified a number of loci associated with chronic inflammatory and autoimmune diseases that encode factors that function in the IL-23 and IL-12 pathways. These genes include IL23A, IL12A, IL12B, IL12RB1, IL12RB2, IL23R, JAK2, TYK2, STAT3, and STAT4 (Lees, C. W. et al., "New IBD genetics: common pathways with other diseases", Gut, 60:1739-1753 (2011): Tao, J. H. et al., "Meta-analysis of TYK2 gene polymorphisms association with susceptibility to autoimmune and inflammatory diseases", Mol. Biol. Rep., 38:4663-4672 (2011); Cho, J. H. et al., "Recent insights into the genetics of inflammatory bowel disease", Gastroenterology, 140:1704-1712 (2011)).

Indeed, anti-p40 treatment, which inhibits both IL-12 and IL-23, as well as IL-23-specific anti-p19 therapies have been shown to be efficacious in the treatment of autoimmunity in diseases including psoriasis, Crohn's Disease and psoriatic arthritis (Leonardi, C. L. et al., "PHOENIX 1 study investigators. Efficacy and safety of ustekinumab, a human interleukin-12/23 monoclonal antibody, in patients with psoriasis: 76-week results from a randomized, double-blind, placebo-controlled trial (PHOENIX 1)", Lancet, 371:1665-1674 (2008); Sandborn, W. J. et al., "Ustekinumab Crohn's Disease Study Group. A randomized trial of Ustekinumab, a human interleukin-12/23 monoclonal antibody, in patients with moderate-to-severe Crohn's disease". Gastroenterology, 135:1130-1141 (2008); Gottlieb, A. et al., "Ustekinumab, a human interleukin 12/23 monoclonal antibody, for psoriatic arthritis: randomized, double-blind, placebo-controlled, crossover trial". Lancet, 373:633-640 (2009)). Therefore, agents which inhibit the action of IL-12 and IL-23 may be expected to have therapeutic benefit in human autoimmune disorders.

The Type I group of interferons (IFNs), which include the IFNα members as well as IFNβ, IFNε, IFNκ and IFNω, act through a heterodimer IFNα/β receptor (IFNAR). Type I IFNs have multiple effects in both the innate and adaptive immune systems including activation of both the cellular and humoral immune responses as well as enhancing the expression and release of autoantigens (Hall, J. C. et al., "Type I interferons: crucial participants in disease amplification in autoimmunity", *Nat. Rev. Rheumatol.,* 6:40-49 (2010)).

In patients with systemic lupus erythematosus (SLE), a potentially fatal autoimmune disease, increased serum levels of interferon (IFN)α (a type I interferon) or increased expression of type I IFN-regulated genes (a so-called IFNα signature) in peripheral blood mononuclear cells and in affected organs has been demonstrated in a majority of patients (Bennett, L. et al., "Interferon and granulopoiesis signatures in systemic lupus erythematosus blood", *J. Exp. Med.,* 197:711-723 (2003); Peterson, K. S. et al., "Characterization of heterogeneity in the molecular pathogenesis of lupus nephritis from transcriptional profiles of laser-captured glomeruli", *J. Clin. Invest.,* 113:1722-1733 (2004)), and several studies have shown that serum IFNα levels correlate with both disease activity and severity (Bengtsson, A. A. et al., "Activation of type I interferon system in systemic lupus erythematosus correlates with disease activity but not with antiretroviral antibodies", *Lupus,* 9:664-671 (2000)). A direct role for IFNα in the pathobiology of lupus is evidenced by the observation that the administration of IFNα to patients with malignant or viral diseases can induce a lupus-like syndrome. Moreover, the deletion of the IFNAR in lupus-prone mice provides high protection from autoimmunity, disease severity and mortality (Santiago-Raber, M. L. et al., "Type-I interferon receptor deficiency reduces lupus-like disease in NZB mice", *J Exp. Med.,* 197:777-788 (2003)), and genome-wide association studies have identified loci associated with lupus that encode factors that function in the type I interferon pathway, including IRF5, IKBKE, TYK2, and STAT4 (Deng, Y. et al., "Genetic susceptibility to systemic lupus erythematosus in the genomic era", *Nat. Rev. Rheumatol.,* 6:683-692 (2010); Sandling, J. K. et al., "A candidate gene study of the type 1 interferon pathway implicates IKBKE and IL8 as risk loci for SLE", *Eur. J. Hum. Genet.,* 19:479-484 (2011)). In addition to lupus, there is evidence that aberrant activation of type I interferon-mediated pathways are important in the pathobiology of other autoimmune diseases such as Sjögren's syndrome and scleroderma (Båve, U. et al., "Activation of the type I interferon system in primary Sjögren's syndrome: a possible etiopathogenic mechanism", *Arthritis Rheum.,* 52:1185-1195 (2005); Kim, D. et al., "Induction of interferon-alpha by scleroderma sera containing autoantibodies to topoisomerase 1: association of higher interferon-alpha activity with lung fibrosis", *Arthritis Rheum.,* 58:2163-2173 (2008)). Therefore, agents which inhibit the action of type I interferon responses may be expected to have therapeutic benefit in human autoimmune disorders.

Tyrosine kinase 2 (Tyk2) is a member of the Janus kinase (JAK) family of nonreceptor tyrosine kinases and has been shown to be critical in regulating the signal transduction cascade downstream of receptors for IL-12, IL-23 and type I interferons in both mice (Ishizaki, M. et al., "Involvement of Tyrosine Kinase-2 in Both the IL-12/Th1 and IL-23/Th17 Axes In vivo", *J. Immunol.,* 187:181-189 (2011); Prchal-Murphy, M. et al., "TYK2 kinase activity is required for functional type I interferon responses in vivo", *PLoS One,* 7:e39141 (2012)) and humans (Minegishi, Y. et al., "Human tyrosine kinase 2 deficiency reveals its requisite roles in multiple cytokine signals involved in innate and acquired immunity", *Immunity,* 25:745-755 (2006)). Tyk2 mediates the receptor-induced phosphorylation of members of the STAT family of transcription factors, an essential signal that leads to the dimerization of STAT proteins and the transcription of STAT-dependent pro-inflammatory genes. Tyk2-deficient mice are resistant to experimental models of colitis, psoriasis and multiple sclerosis, demonstrating the importance of Tyk2-mediated signaling in autoimmunity and related disorders (Ishizaki, M. et al., "Involvement of Tyrosine Kinase-2 in Both the IL-12/Th1 and IL-23/Th17 Axes In vivo", *J. Immunol.,* 187:181-189 (2011); Oyamada. A. et al., "Tyrosine kinase 2 plays critical roles in the pathogenic CD4 T cell responses for the development of experimental autoimmune encephalomyelitis", *J. Immunol.,* 183:7539-7546 (2009)).

In humans, individuals expressing an inactive variant of Tyk2 are protected from multiple sclerosis and possibly other autoimmune disorders (Couturier, N. et al., "Tyrosine kinase 2 variant influences T lymphocyte polarization and multiple sclerosis susceptibility". *Brain,* 134:693-703 (2011)). Genome-wide association studies have shown other variants of Tyk2 to be associated with autoimmune disorders such as Crohn's Disease, psoriasis, systemic lupus erythematosus, and rheumatoid arthritis, further demonstrating the importance of Tyk2 in autoimmunity (Ellinghaus, D. et al., "Combined Analysis of Genome-wide Association Studies for Crohn Disease and Psoriasis Identifies Seven Shared Susceptibility Loci", *Am. J. Hum. Genet.,* 90:636-647 (2012); Graham, D. et al., "Association of polymorphisms across the tyrosine kinase gene, TYK2 in UK SLE families", *Rheumatology (Oxford),* 46:927-930 (2007); Eyre, S. et al., "High-density genetic mapping identifies new susceptibility loci for rheumatoid arthritis", *Nat. Genet.,* 44:1336-1340 (2012)).

In view of the conditions that may benefit by treatment involving the modulation of cytokines and/or interferons, new compounds capable of modulating cytokines and/or interferons, such as IL-12, IL-23 and/or IFNα, and methods of using these compounds may provide substantial therapeutic benefits to a wide variety of patients in need thereof.

SUMMARY OF THE INVENTION

The invention is directed to compounds of Formula I, infra, that which are useful as modulators of IL-12, IL-23 and/or IFNα by inhibiting Tyk2-mediated signal transduction.

The present invention also provides processes and intermediates for making the compounds of the present invention.

The present invention also provides pharmaceutical compositions comprising a pharmaceutically acceptable carrier and at least one of the compounds of the present invention.

The present invention also provides a method for the modulation of IL-12, IL-23 and/or IFNα by inhibiting Tyk-2-mediated signal transduction comprising administering to a host in need of such treatment a therapeutically effective amount of at least one of the compounds of the present invention.

The present invention also provides a method for treating proliferative, metabolic, allergic, autoimmune and inflammatory diseases, comprising administering to a host in need of such treatment a therapeutically effective amount of at least one of the compounds of the present invention.

A preferred embodiment is a method for treating inflammatory and autoimmune diseases or diseases. For the purposes of this invention, an inflammatory and autoimmune disease or disorder includes any disease having an inflammatory or autoimmune component.

The present invention also provides the use of the compounds of the present invention for the manufacture of a medicament for the treatment of cancers.

The present invention also provides the compounds of the present invention for use in therapy.

These and other features of the invention will be set forth in the expanded form as the disclosure continues.

DETAILED DESCRIPTION OF THE EMBODIMENTS OF THE INVENTION

In a first aspect of the present invention, there is provided a compound of formula (I)

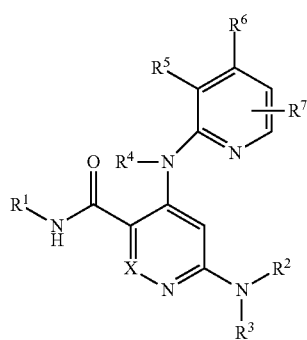

I wherein

X is N or CH;

$R^1$ is selected from H, $CD_3$, $C_{1-3}$ alkyl or $C_{3-6}$ cycloalkyl;

$R^2$ is —C(O)$R^{2a}$; $C_{1-6}$alkyl, —(CH$_2$)$_r$-3-14 membered carbocycle substituted with 0-1 $R^{2a}$ or a 5-12 membered heterocycle containing 1-4 heteroatoms selected from N, O, and S, substituted with 0-4 $R^{2a}$;

$R^{2a}$ at each occurrence is independently H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, (CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, $C_{1-6}$ alkyl substituted with 0-3 $R^a$, $C_{1-6}$ haloalkyl, $C_{2-6}$ alkenyl substituted with 0-3 $R^a$, —(CH$_2$)$_r$-3-14 membered carbocycle substituted with 0-1 $R^a$ or a —(CH$_2$)$_r$-5-7 membered heterocycle containing 1-4 heteroatoms selected from N, O, and S(O)$_p$ substituted with 0-2 $R^a$;

$R^3$ is H, $C_{1-3}$ alkyl or $C_{3-6}$ cycloalkyl; $R^4$ is H, $C_{1-3}$ alkyl or $C_{3-6}$ cycloalkyl;

$R^5$ is $C_{1-4}$ alkyl substituted with 0-1 $R^{5a}$, $C_{1-4}$ alkoxy substituted with 0-1 $R^a$, (CH$_2$)$_r$-phenyl substituted with 0-3 $R^{5a}$ or a —(CH$_2$)-5-7 membered heterocycle containing 1-4 heteroatoms selected from N, O, and S(O)$_p$;

$R^{5a}$ is independently at each occurrence, H, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^e$, $C_{1-6}$ alkyl or (CH$_2$)$_r$-phenyl substituted with 0-3 $R^f$;

$R^6$ is $C_{1-4}$ alkyl substituted with 0-1 $R^{6a}$, (CH$_2$)$_r$-phenyl substituted with 0-3 $R^{6a}$ or a —(CH$_2$)-5-7 membered heterocycle containing 1-4 heteroatoms selected from N, O, and S(O)$_p$ substituted with 0-3 $R^{6a}$;

$R^{6a}$ is H, $C_{1-4}$ alkyl substituted with 0-3 $R^f$, CF$_3$, $C_{3-10}$ cycloalkyl substituted with 0-1 $R^f$, (CH)$_r$-phenyl substituted with 0-3 $R^d$ or —(CH$_2$)$_r$-5-7 membered heterocycle containing 1-4 heteroatoms selected from N, O, and S(O)$_p$ substituted with 0-3 $R^d$;

$R^7$ is H, $C_{1-3}$ alkyl or $C_{3-6}$ cycloalkyl;

$R^{11}$ at each occurrence is independently H, $C_{1-4}$ alkyl substituted with 0-3 $R^f$, CF$_3$, $C_{3-10}$ cycloalkyl substituted with 0-1 $R^f$, (CH$_2$)$_r$-phenyl substituted with 0-3 $R^d$ or —(CH$_2$)$_r$-5-7 membered heterocycle containing 1-4 heteroatoms selected from N, O, and S(O)$_p$ substituted with 0-3 $R^d$;

$R^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_2$R$^c$, —S(O)$_2$R$^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 $R^f$;

$R^b$ is H, $C_{1-6}$ alkyl substituted with 0-3 $R^d$, $C_{1-6}$ haloalkyl, $C_{3-6}$ cycloalkyl substituted with 0-2 $R^d$, or —(CH$_2$)$_r$-5-7 membered heterocycle containing 1-4 heteroatoms selected from N, O, and S(O)$_p$ substituted with 0-3 $R^f$ or (CH$_2$)$_r$-phenyl substituted with 0-3 $R^d$;

$R^c$ is $C_{1-6}$ alkyl substituted with 0-3 $R^f$, (CH$_2$)$_r$—$C_{3-6}$ cycloalkyl substituted with 0-3 $R^f$ or (CH$_2$)$_r$-phenyl substituted with 0-3 $R^f$;

$R^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, $C_{1-6}$ alkyl or (CH$_2$)$_r$-phenyl substituted with 0-3 $R^f$;

$R^e$ is independently at each occurrence, hydrogen, $C_{1-6}$ alkyl, $C_{3-6}$ cycloalkyl or (CH$_2$)$_r$-phenyl substituted with 0-3 $R^f$;

$R^f$ is independently at each occurrence, hydrogen, halo, CN, NH$_2$, OH, $C_{3-6}$ cycloalkyl, CF$_3$, O($C_{1-6}$ alkyl) or a —(CH$_2$)$_r$-5-7 membered heterocycle containing 1-4 heteroatoms selected from N, O, and S(O)$_p$;

p is 0, 1, or 2;

r is 0, 1, 2, 3, or 4;

or a stereoisomer or pharmaceutically acceptable salt thereof.

In a second aspect of the invention, there is provided a compound of the formula

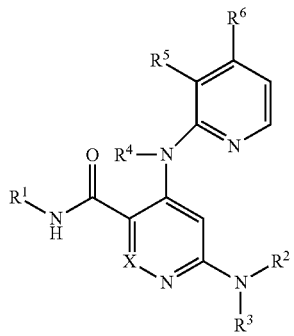

wherein

X is N or CH;

$R^1$ is selected from H, $CD_3$, $C_{1-3}$ alkyl or $C_{3-6}$ cycloalkyl;

$R^2$ is —C(O)$R^{2a}$; $C_{1-6}$ alkyl, —(CH$_2$)$_r$-3-14 membered carbocycle substituted with 0-1 $R^{2a}$ or a 5-12 membered heterocycle containing 1-4 heteroatoms selected from N, O, and S, substituted with 0-4 $R^{2a}$;

$R^{2a}$ at each occurrence is independently H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH)$_r$-5-7 membered heterocycle containing 1-4 heteroatoms selected from N, O, and S(O)$_p$ substituted with 0-2 R$^a$;

R$^3$ is H, C$_{1-3}$ alkyl or C$_{3-6}$cycloalkyl; R$^4$ is H, C$_{1-3}$ alkyl or C$_{3-6}$ cycloalkyl;

R$^5$ is C$_{1-4}$ alkyl substituted with 0-1 R$^{5a}$, C$_{1-4}$ alkoxy substituted with 0-1R$^{5a}$, (CH$_2$)$_r$-phenyl substituted with 0-3 R$^{5a}$ or a —(CH$_2$)-5-7 membered heterocycle containing 1-4 heteroatoms selected from N, O, and S(O)$_p$;

R$^{5a}$ is independently at each occurrence, H, F, Cl, Br, OCF$_3$, CF$_3$, CN, NO$_2$, —OR$^c$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^6$ is C$_{1-4}$ alkyl substituted with 0-1 R$^{6a}$, (CH$_2$)$_r$-phenyl substituted with 0-3 R$^{6a}$ or a —(CH$_2$)-5-7 membered heterocycle containing 1-4 heteroatoms selected from N, O, and S(O)$_p$ substituted with 0-3 R$^{6a}$;

R$^{6a}$ is H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^{11}$ at each occurrence is independently H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$, alkyl substituted with 0-3 R$^f$, C$_{1-6}$ haloalkyl, C$_{2-6}$ alkenyl substituted with 0-3 R$^8$, C$_{2-6}$ alkynyl substituted with 0-3 R$^f$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle containing 1-4 heteroatoms selected from N, O, and S(O)$_p$ substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle containing 1-4 heteroatoms selected from N, O, and S(O)$_p$;

p is 0, 1, or 2;

r is 0, 1, 2, 3, or 4;

or a stereoisomer or pharmaceutically acceptable salt thereof.

In a third aspect of the invention, there is provided a compound of the formula

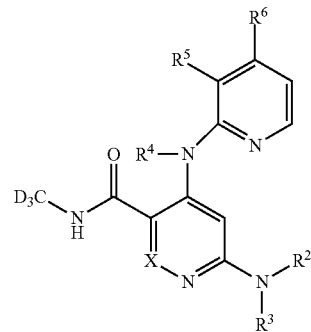

wherein

X is N or CH;

R$^2$ is —C(O)R$^{2a}$; C$_{1-6}$alkyl, —(CH$_2$)$_r$-3-14 membered carbocycle substituted with 0-1 R$^{2a}$ or a 5-12 membered heterocycle containing 1-4 heteroatoms selected from N, O, and S, substituted with 0-4 R$^{2a}$;

R$^{2a}$ at each occurrence is independently H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle containing 1-4 heteroatoms selected from N, O, and S(O)$_p$ substituted with 0-2 R$^a$;

R$^3$ is H, C$_{1-3}$ alkyl or C$_{3-6}$ cycloalkyl; R$^4$ is H, C$_{1-3}$ alkyl or C$_{3-6}$ cycloalkyl;

R$^5$ is C$_{1-4}$ alkyl substituted with 0-1 R$^{5a}$, C$_{1-4}$ alkoxy substituted with 0-1 R$^{5a}$, (CH$_2$)$_r$-phenyl substituted with 0-3 R$^{5a}$ or a —(CH$_2$)-5-7 membered heterocycle containing 1-4 heteroatoms selected from N, O, and S(O)$_p$;

R$^{5a}$ is independently at each occurrence, H, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^6$ is C$_{1-4}$ alkyl substituted with 0-1 R$^{6a}$, (CH$_2$)$_r$-phenyl substituted with 0-3 R$^{6a}$ or a —(CH$_2$)-5-7 membered heterocycle containing 1-4 heteroatoms selected from N, O, and S(O)$_p$ substituted with 0-3 R$^{6a}$;

R$^{6a}$ is H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^{11}$ at each occurrence is independently H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$, alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle containing 1-4 heteroatoms selected from N, O, and S(O)$_p$ substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle containing 1-4 heteroatoms selected from N, O, and S(O)$_p$;

p is 0, 1, or 2;

r is 0, 1, 2, 3, or 4;

or a stereoisomer or pharmaceutically acceptable salt thereof.

In a 4th aspect of the invention, there is provided a compound of the formula

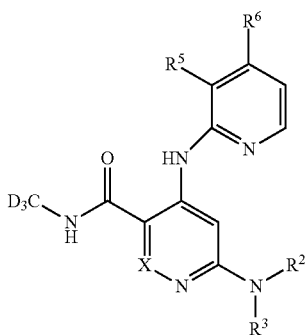

wherein

X is N or CH;

R$^2$ is —C(O)R$^{2a}$, C$_{1-6}$ alkyl, —(CH$_2$)$_r$-3-14 membered carbocycle substituted with 0-1 R$^{2a}$ or a 5-12 membered heterocycle containing 1-4 heteroatoms selected from N, O, and S, substituted with 0-4 R$^{2a}$;

R$^{2a}$ at each occurrence is independently H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, (CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle containing 1-4 heteroatoms selected from N, O, and S(O)$_p$ substituted with 0-2 R$^a$;

R$^3$ is H, C$_{1-3}$alkyl or C$_{3-6}$ cycloalkyl; R$^5$ is C$_{1-4}$ alkyl substituted with 0-1 R$^{5a}$, C$_{1-4}$ alkoxy substituted with 0-1 R$^{5a}$, (CH$_2$)$_r$-phenyl substituted with 0-3 R$^{5a}$ or a —(CH$_2$)-5-7 membered heterocycle containing 1-4 heteroatoms selected from N, O, and S(O)$_p$;

R$^{5a}$ is independently at each occurrence, H, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^6$ is C$_{1-4}$ alkyl substituted with 0-1 R$^{6a}$, (CH$_2$)$_r$-phenyl substituted with 0-3 R$^{6a}$ or a —(CH$_2$)-5-7 membered heterocycle containing 1-4 heteroatoms selected from N, O, and S(O)$_p$ substituted with 0-3 R$^{6a}$;

R$^{6a}$ is H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^{11}$ at each occurrence is independently H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$, alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle containing 1-4 heteroatoms selected from N, O, and S(O)$_p$ substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle containing 1-4 heteroatoms selected from N, O, and S(O)$_p$;

p is 0, 1, or 2;

r is 0, 1, 2, 3, or 4;

or a stereoisomer or pharmaceutically acceptable salt thereof.

In a 5th aspect of the invention, there is provided a compound of the formula

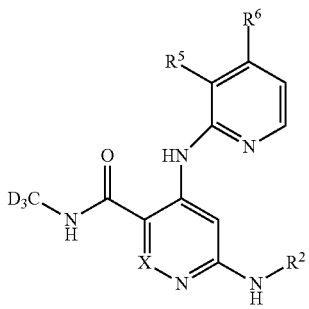

wherein

X is N or CH;

R$^2$ is —C(O)R$^{2a}$; C$_{1-6}$ alkyl, —(CH$_2$)$_r$-3-14 membered carbocycle substituted with 0-1 R$^{2a}$ or a 5-12 membered heterocycle containing 1-4 heteroatoms selected from N, O, and S, substituted with 0-4 R$^{2a}$;

R$^{2a}$ at each occurrence is independently H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$haloalkyl, C$_{2-6}$alkenyl substituted with 0-3 R$^a$, —(CH$_2$)$_r$-3-14 membered carbocycle substituted with 0-1 R$^a$ or a —(CH$_2$)$_r$-5-7 membered heterocycle containing 1-4 heteroatoms selected from N, O, and S(O)$_p$ substituted with 0-2 R$^a$;

R$^5$ is C$_{1-4}$ alkyl substituted with 0-1 R$^{5a}$, C$_{1-4}$ alkoxy substituted with 0-1 R$^{5a}$, (CH$_2$)$_r$-phenyl substituted with 0-3 R$^{5a}$ or a —(CH$_2$)-5-7 membered heterocycle containing 1-4 heteroatoms selected from N, O, and S(O)$_p$;

R$^{5a}$ is independently at each occurrence, H, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^6$ is C$_{1-4}$ alkyl substituted with 0-1 R$^{6a}$, (CH$_2$)$_r$-phenyl substituted with 0-3 R$^{6a}$ or a —(CH$_2$)-5-7 membered heterocycle containing 1-4 heteroatoms selected from N, O, and S(O)$_p$ substituted with 0-3 R$^{6a}$;

R$^{6a}$ is H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^{11}$ at each occurrence is independently H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^a$ at each occurrence is independently H, F, Cl, Br, OCF$_3$, CF$_3$, CHF$_2$, CN, NO$_2$, —(CH$_2$)$_r$OR$^b$, (CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle containing 1-4 heteroatoms selected from N, O, and S(O)$_p$ substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —OR$^e$, —(CH$_2$)$_r$(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle containing 1-4 heteroatoms selected from N, O, and S(O)$_p$;

p is 0, 1, or 2;

r is 0, 1, 2, 3, or 4;

or a stereoisomer or pharmaceutically acceptable salt thereof.

In a 6th aspect of the invention, there is provided a compound of the formula

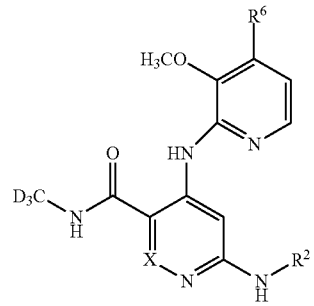

wherein

X is N or CH;

R$^2$ is —C(O)R$^{2a}$; C$_{1-6}$alkyl, —(CH$_2$)$_r$-3-14 membered carbocycle substituted with 0-1 R$^{2a}$ or a 5-12 membered heterocycle containing 1-4 heteroatoms selected from N, O, and S, substituted with 0-4 R$^{2a}$;

R$^{2a}$ at each occurrence is independently H, OCF$_3$, CN, NO$_2$, (CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_r$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle containing 1-4 heteroatoms selected from N, O, and S(O)$_p$ substituted with 0-2 R$^a$;

R$^6$ is C$_{1-4}$ alkyl substituted with 0-1 R$^b$, (CH$_2$)$_r$-phenyl substituted with 0-3 R$^{6a}$ or a —(CH$_2$)-5-7 membered heterocycle containing 1-4 heteroatoms selected from N, O, and S(O)$_p$ substituted with 0-3 R$^{6a}$;

R$^{6a}$ is H, C$_{1-4}$ alkyl substituted with 0-3 R$^f$ CF$_3$, C$_{3-10}$ cycloalkyl substituted with 0-1 R$^f$ (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^{11}$ at each occurrence is independently H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle containing 1-4 heteroatoms selected from N, O, and S(O)$_p$ substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH)$_r$-phenyl substituted with 0-3 R$^f$;

R$^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle containing 1-4 heteroatoms selected from N, O, and S(O)$_p$;

p is 0, 1, or 2;

r is 0, 1, 2, 3, or 4;

or a stereoisomer or pharmaceutically acceptable salt thereof.

In a 7th aspect of the invention, there is provided a compound of the formula

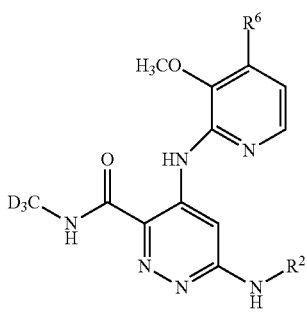

wherein

R$^2$ is —C(O)R$^{2a}$; C$_{1-6}$ alkyl, —(CH$_2$)$_r$-3-14 membered carbocycle substituted with 0-1 R$^{2a}$ or a 5-12 membered heterocycle containing 1-4 heteroatoms selected from N, O, and S, substituted with 0-4 R$^{2a}$;

R$^{2a}$ at each occurrence is independently H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle containing 1-4 heteroatoms selected from N, O, and S(O)$_p$ substituted with 0-2 R$^a$;

R$^6$ is C$_{1-4}$ alkyl substituted with 0-1 R$^{6a}$, (CH$_2$)$_r$-phenyl substituted with 0-3 R$^{6a}$ or a —(CH$_2$)-5-7 membered heterocycle containing 1-4 heteroatoms selected from N, O, and S(O)$_p$ substituted with 0-3 R$^{6a}$;

R$^{6a}$ is H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^{11}$ at each occurrence is independently H, C$_{1-4}$ alkyl substituted with 0-3 R$^f$, CF$_3$, C$_{3-10}$ cycloalkyl substituted with 0-1 R$^f$ (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, (CH$_2$)$_r$OC(O)R$^b$, —(CH$_2$)$_r$NR$^{11}$R$^{11}$, (CH$_2$)$_r$C(O)NR$^{11}$R$^{11}$, —(CH$_2$)$_r$NR$^b$C(O)R$^c$, (CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$ C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle containing 1-4 heteroatoms selected from N, O, and S(O)$_p$ substituted with 0-3 R$^f$ or (CH$_2$)$_r$-phenyl substituted with 0-3 R$^d$; R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle containing 1-4 heteroatoms selected from N, O, and S(O)$_p$;

p is 0, 1, or 2;

r is 0, 1, 2, 3, or 4;

or a stereoisomer or pharmaceutically acceptable salt thereof.

In an 8th aspect of the invention, there is provided a compound of the formula

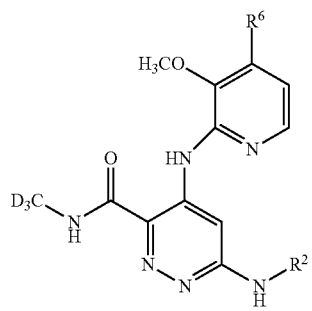

wherein
R² is —C(O)R²ᵃ; C₁₋₆ alkyl, —(CH₂)ᵣ-3-14 membered carbocycle substituted with 0-1 R²ᵃ or a 5-12 membered heterocycle containing 1-4 heteroatoms selected from N, O, and S, substituted with 0-4 R²ᵃ;

R²ᵃ at each occurrence is independently H, OCF₃, CN, NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, —S(O)ₚRᶜ, C₁₋₆ alkyl substituted with 0-3 Rᵃ, C₁₋₆ haloalkyl, C₂₋₆ alkenyl substituted with 0-3 Rᵃ, —(CH₂)ᵣ-3-14 membered carbocycle substituted with 0-1 Rᵃ or a —(CH₂)ᵣ-5-7 membered heterocycle containing 1-4 heteroatoms selected from N, O, and S(O)ₚ substituted with 0-2 Rᵃ;

R⁶ is C₁₋₄ alkyl substituted with 0-1 R⁶ᵃ, (CH₂)ᵣ-phenyl substituted with 0-3 R⁶ᵃ or a —(CH₂)-5-7 membered heterocycle containing 1-4 heteroatoms selected from N, O, and S(O)ₚ substituted with 0-3 R⁶ᵃ;

R⁶ᵃ is H, C₁₋₄ alkyl substituted with 0-3 Rᶠ, CF₃, C₃₋₁₀ cycloalkyl substituted with 0-1 Rᶠ, (CH)ᵣ-phenyl substituted with 0-3 Rᵈ or —(CH₂)ᵣ-5-7 membered heterocycle containing 1-4 heteroatoms selected from N, O, and S(O)ₚ substituted with 0-3 Rᵈ;

R¹¹ at each occurrence is independently H, C₁₋₄ alkyl substituted with 0-3 Rᶠ, CF₃, C₃₋₁₀ cycloalkyl substituted with 0-1 Rᶠ, (CH)ᵣ-phenyl substituted with 0-3 Rᵈ or —(CH₂)ᵣ-5-7 membered heterocycle containing 1-4 heteroatoms selected from N, O, and S(O)ₚ substituted with 0-3 Rᵈ;

Rᵃ at each occurrence is independently H, F, Cl, Br, OCF₃, CF₃, CHF₂, CN, NO₂, —(CH₂)ᵣORᵇ, —(CH₂)ᵣSRᵇ, —(CH₂)ᵣC(O)Rᵇ, (CH₂)ᵣC(O)ORᵇ, —(CH₂)ᵣOC(O)Rᵇ, —(CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, —S(O)Rᶜ, —S(O)₂Rᶜ, C₁₋₆ alkyl substituted with 0-3 Rᶠ, C₁₋₆ haloalkyl, C₂₋₆ alkenyl substituted with 0-3 Rᵃ, C₂₋₆ alkynyl substituted with 0-3 Rᵃ, —(CH₂)ᵣ-3-14 membered carbocycle or —(CH₂)ᵣ-5-7 membered heterocycle containing 1-4 heteroatoms selected from N, O, and S(O)ₚ substituted with 0-3 Rᶠ;

Rᵇ is H, C₁₋₆ alkyl substituted with 0-3 Rᵈ, C₁₋₆ haloalkyl, C₃₋₆ cycloalkyl substituted with 0-2 Rᵈ, or —(CH₂)ᵣ-5-7 membered heterocycle containing 1-4 heteroatoms selected from N, O, and S(O)ₚ substituted with 0-3 Rᶠ or (CH₂)ᵣ-phenyl substituted with 0-3 Rᵈ;

Rᶜ is C₁₋₆ alkyl substituted with 0-3 Rᶠ, (CH₂)ᵣ—C₃₋₆ cycloalkyl substituted with 0-3 Rᶠ or (CH₂)ᵣ-phenyl substituted with 0-3 Rᶠ;

Rᵈ is independently at each occurrence, hydrogen, F, Cl, Br, OCF₃, CF₃, CN, NO₂, —ORᵉ, —(CH₂)ᵣC(O)Rᶜ, —NRᵉRᵉ, —NRᵉC(O)ORᶜ, C₁₋₆ alkyl or (CH₂)ᵣ-phenyl substituted with 0-3 Rᶠ;

Rᵉ is independently at each occurrence, hydrogen, C₁₋₆ alkyl, C₃₋₆ cycloalkyl or (CH₂)ᵣ-phenyl substituted with 0-3 Rᶠ;

Rᶠ is independently at each occurrence, hydrogen, halo, CN, NH₂, OH, C₃₋₆ cycloalkyl, CF₃, O(C₁₋₆ alkyl) or a —(CH₂)ᵣ-5-7 membered heterocycle containing 1-4 heteroatoms selected from N, O, and S(O)ₚ;

p is 0, 1, or 2;
r is 0, 1, 2 or 3;
or a stereoisomer or pharmaceutically acceptable salt thereof.

In a 9th aspect of the invention, there is provided a compound of the formula

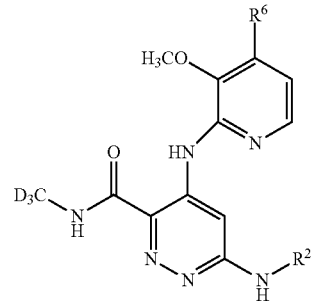

wherein
R² is —C(O)R²ᵃ or a 5-12 membered heterocycle containing 1-4 heteroatoms selected from N, O, and S, substituted with 0-4 R²ᵃ;

R²ᵃ at each occurrence is independently H, OCF₃, CN, NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, CH₂)ᵣNR¹¹R¹¹, —(CH₂)ᵣC(O)NR¹¹R¹¹, —(CH₂)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, —S(O)ₚRᶜ, C₁₋₆ alkyl substituted with 0-3 Rᵃ, C₁₋₆ haloalkyl, C₂₋₆ alkenyl substituted with 0-3 Rᵃ, —(CH₂)ᵣ-3-14 membered carbocycle substituted with 0-1 Rʷ or a —(CH)ᵣ-5-7 membered heterocycle containing 1-4 heteroatoms selected from N, O, and S(O)ₚ substituted with 0-2 Rᵃ;

R⁶ is C₁₋₄ alkyl substituted with 0-1 R⁶ᵃ, (CH₂)ᵣ-phenyl substituted with 0-3 R⁶ᵃ or a —(CH₂)-5-7 membered heterocycle containing 1-4 heteroatoms selected from N, O, and S(O)ₚ substituted with 0-3 R⁶ᵃ;

R¹¹ is H, C₁₋₄ alkyl substituted with 0-3 Rᶠ, CF₃, C₃₋₁₀ cycloalkyl substituted with 0-1 Rᶠ, (CH)ᵣ-phenyl substituted with 0-3 Rᵈ or —(CH₂)ᵣ-5-7 membered heterocycle containing 1-4 heteroatoms selected from N, O, and S(O)ₚ substituted with 0-3 Rᵈ;

R¹¹ at each occurrence is independently H, C₁₋₄ alkyl substituted with 0-3 Rᶠ, CF₃, C₃₋₁₀ cycloalkyl substituted with 0-1 Rᶠ, (CH)ᵣ-phenyl substituted with 0-3 Rᵈ or —(CH₂)ᵣ-5-7 membered heterocycle containing 1-4 heteroatoms selected from N, O, and S(O)ₚ substituted with 0-3 Rᵈ;

Rᵃ at each occurrence is independently H, F, Cl, Br, OCF₃, CF₃, CHF₂, CN, NO₂, —(CH₂)ᵣORᵇ, —(CH₂)ᵣSRᵇ, —(CH₂)ᵣC(O)Rᵇ, —(CH₂)ᵣC(O)ORᵇ, —(CH₂)ᵣOC(O)Rᵇ, —(CH₂)ᵣNR¹¹R¹¹, —(CH₂)ᵣC(O)NR¹¹R¹¹, —(CH)ᵣNRᵇC(O)Rᶜ, —(CH₂)ᵣNRᵇC(O)ORᶜ, —NRᵇC(O)NR¹¹R¹¹, —S(O)ₚNR¹¹R¹¹, —NRᵇS(O)ₚRᶜ, —S(O)Rᶜ, —S(O)₂Rᶜ, C₁₋₆ alkyl substituted with 0-3 Rᶠ, C₁₋₆ haloalkyl, C₂₋₆ alkenyl substituted with 0-3 Rᵃ, C₂₋₆ alkynyl substituted with 0-3 Rᵃ, —(CH₂)ᵣ-3-14 membered carbocycle or —(CH₂)ᵣ-5-7 membered heterocycle containing 1-4 heteroatoms selected from N, O, and S(O)ₚ substituted with 0-3 Rᶠ;

Rᵇ is H, C₁₋₆ alkyl substituted with 0-3 Rᵈ, C₁₋₆ haloalkyl, C₃₋₆ cycloalkyl substituted with 0-2 Rᵈ, or —(CH₂)ᵣ-5-7 membered heterocycle containing 1-4 heteroatoms selected from N, O, and S(O)ₚ substituted with 0-3 Rᶠ or (CH₂)ᵣ-phenyl substituted with 0-3 Rᵈ;

Rᶜ is C₁₋₆ alkyl substituted with 0-3 Rᶠ, (CH₂)ᵣ—C₃₋₆ cycloalkyl substituted with 0-3 Rᶠ or (CH₂)ᵣ-phenyl substituted with 0-3 Rᶠ;

Rᵈ is independently at each occurrence, hydrogen, F, Cl, Br, OCF₃, CF₃, CN, NO₂, —ORᵉ, —(CH₂)ᵣC(O)Rᶜ, —NRᵉRᵉ, —NRᵉC(O)ORᶜ, C₁₋₆ alkyl or (CH₂)ᵣ-phenyl substituted with 0-3 Rᶠ;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a $-(CH_2)_r$-5-7 membered heterocycle containing 1-4 heteroatoms selected from N, O, and $S(O)_p$;

p is 0, 1, or 2;

r is 0, 1, 2 or 3;

or a stereoisomer or pharmaceutically acceptable salt thereof.

In a 10th aspect of the invention, there is provided a compound of the formula

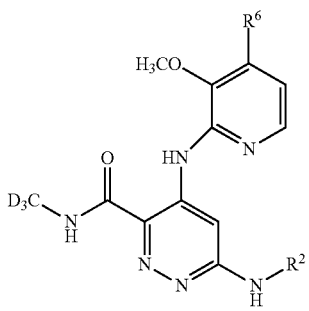

wherein $R^2$ is $-C(O)R^{2a}$ or a 5-12 membered heterocycle containing 1-4 heteroatoms selected from N, O, and S, substituted with 0-4 $R^{2a}$;

$R^{2a}$ at each occurrence is independently H, $OCF_3$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)_pR^c$, $C_{1-6}$ alkyl substituted with 0-3 $R^a$, $C_{1-6}$ haloalkyl, $C_{2-6}$ alkenyl substituted with 0-3 $R^a$, $-(CH_2)_r$-3-14 membered carbocycle substituted with 0-1 $R^a$ or a $-(CH)_r$-5-7 membered heterocycle containing 1-4 heteroatoms selected from N, O, and $S(O)_p$ substituted with 0-2 $R^a$;

$R^6$ is a $-(CH_2)$-5-7 membered heterocycle containing 1-4 heteroatoms selected from N, O, and $S(O)_p$ substituted with 0-3 $R^{6a}$;

$R^{11}$ at each occurrence is independently H, $C_{1-4}$ alkyl substituted with 0-3 $R^f$, $CF_3$, $R^{6a}$ is H, $C_{1-4}$ alkyl substituted with 0-3 $R^f$, $CF_3$, $C_{3-10}$ cycloalkyl substituted with 0-1 $R^f$, $(CH)_r$-phenyl substituted with 0-3 $R^d$ or $-(CH_2)_r$-5-7 membered heterocycle containing 1-4 heteroatoms selected from N, O, and $S(O)_p$ substituted with 0-3 $R^d$;

$R^{11}$ at each occurrence is independently H, $C_{1-4}$ alkyl substituted with 0-3 $R^f$, $CF_3$, $C_{3-10}$ cycloalkyl substituted with 0-1 $R^f$, $(CH)_r$-phenyl substituted with 0-3 $R^d$ or $-(CH_2)_r$-5-7 membered heterocycle containing 1-4 heteroatoms selected from N, O, and $S(O)_p$ substituted with 0-3 $R^d$;

$R^a$ at each occurrence is independently H, F, Cl, Br, $OCF_3$, $CF_3$, $CHF_2$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $(CH)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)_pR^c$, $-S(O)_2R^c$, $C_{1-6}$ alkyl substituted with 0-3 $R^f$ $C_{1-6}$ haloalkyl, $C_{2-6}$ alkenyl substituted with 0-3 $R^a$, $C_{2-6}$ alkynyl substituted with 0-3 $R^a$, $-(CH_2)_r$-3-14 membered carbocycle or $-(CH_2)_r$-5-7 membered heterocycle containing 1-4 heteroatoms selected from N, O, and $S(O)_p$ substituted with 0-3 $R^f$;

$R^b$ is H, $C_{1-6}$ alkyl substituted with 0-3 $R^d$, $C_{1-6}$ haloalkyl, $C_{3-6}$ cycloalkyl substituted with 0-2 $R^d$, or $-(CH_2)_r$-5-7 membered heterocycle containing 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, $-OR^e$, $-(CH_2)_rC(O)R^c$, $-NR^eR^e$, $-NR^eC(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a $-(CH_2)_r$-5-7 membered heterocycle containing 1-4 heteroatoms selected from N, O, and $S(O)_p$;

p is 0, 1, or 2;

r is 0, 1, 2 or 3;

or a stereoisomer or pharmaceutically acceptable salt thereof.

In an 1th aspect of the invention, there is provided a compound of the formula

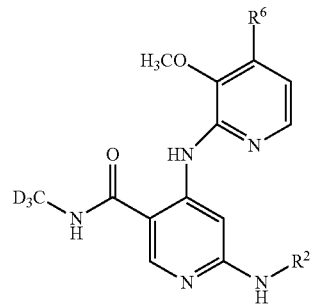

wherein $R^2$ is $-C(O)R^{2a}$ or a 5-12 membered heterocycle containing 1-4 heteroatoms selected from N, O, and S, substituted with 0-4 $R^{2a}$;

$R^{2a}$ at each occurrence is independently H, $OCF_3$, CN, $N_2$, $(CH_2)_rOR^b$, $-(CH_2)_rSR^b$ $(CH_2)_rC(O)R^b$, $-(CH_2)_rC(O)OR^b$, $-(CH_2)_rOC(O)R^b$, $CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)_p^c$, $C_{1-6}$ alkyl substituted with 0-3 $R^a$, $C_{1-6}$ haloalkyl, $C_{2-6}$ alkenyl substituted with 0-3 $R^a$, $-(CH_2)_r$-3-14 membered carbocycle substituted with 0-1 $R^a$ or a $-(CH_2)_r$-5-7 membered heterocycle containing 1-4 heteroatoms selected from N, O, and $S(O)_p$ substituted with 0-2 $R^a$;

$R^6$ is a $-(CH_2)$-5-7 membered heterocycle containing 1-4 heteroatoms selected from N, O, and $S(O)_p$ substituted with 0-3 $R^{6a}$;

$R^{6a}$ is H, $C_{1-4}$ alkyl substituted with 0-3 $R^f$ $CF_3$, $C_{3-10}$ cycloalkyl substituted with 0-1 $R^f$ $(CH)_r$-phenyl substituted with 0-3 $R^d$ or $-(CH_2)_r$-5-7 membered heterocycle containing 1-4 heteroatoms selected from N, O, and $S(O)_p$ substituted with 0-3 $R^d$;

$R^{11}$ at each occurrence is independently H, $C_{1-4}$ alkyl substituted with 0-3 $R^f$, $CF_3$, $C_{3-10}$ cycloalkyl substituted with 0-1 $R^f$, $(CH)_r$-phenyl substituted with 0-3 $R^d$ or —(CH$_2$)$_r$-5-7 membered heterocycle containing 1-4 heteroatoms selected from N, O, and S(O)$_p$ substituted with 0-3 R$^d$;

R$^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle containing 1-4 heteroatoms selected from N, O, and S(O)$_p$ substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle containing 1-4 heteroatoms selected from N, O, and S(O)$_p$;

p is 0, 1, or 2;

r is 0, 1, 2 or 3;

or a stereoisomer or pharmaceutically-acceptable salt thereof.

In another aspect, there is provided a compound selected from the exemplified examples within the scope of the first aspect, or a pharmaceutically acceptable salt or stereoisomer thereof.

In another aspect, there is provided a compound selected from any subset list of compounds within the scope of any of the above aspects.

In another aspect, there is provided a compound (IUPAC naming convention) selected from 6-cyclopropaneamido-4-{[3-methoxy-4-(1-methyl-1H-1,2,4-triazol-3-yl)pyridin-2-yl]amino}-N—($^2$H$_3$)methylpyridazine-3-carboxamide, 4-{[3-methoxy-4-(1-methyl-1H-1,2,4-triazol-3-yl)pyridin-2-yl]amino}-N—($^2$H$_3$)methyl-6-[(pyridin-2-yl)amino]pyridazine-3-carboxamide, 6-cyclobutaneamido-4-{[3-methoxy-4-(1-methyl-1H-1,2,4-triazol-3-yl)pyridin-2-yl]amino}-N—($^2$H$_3$)methylpyridazine-3-carboxamide, 4-{[3-methoxy-4-(1-methyl-1H-1,2,4-triazol-3-yl)pyridin-2-yl]amino}-N—($^2$H$_3$)methy-6-[2-(morpholin-4-yl)acetamido]pyridazine-3-carboxamide, 6-acetamido-4-{[3-methoxy-4-(1-methyl-1H-1,2,4-triazol-3-yl)pyridin-2-yl]amino}-N—($^2$H$_3$)methylpyridazine-3-carboxamide, 6-[(5-fluoropyridin-2-yl)amino]-4-{[3-methoxy-4-(1-methyl-1H-1,2,4-triazol-3-yl)pyridin-2-yl]amino}-N—($^2$H$_3$)methylpyridazine-3-carboxamide, 6-butanamido-4-{[3-methoxy-4-(1-methyl-1H-1,2,4-triazol-3-yl)pyridin-2-yl]amino}-N—($^2$H$_3$)methylpyridazine-3-carboxamide, 4-{[3-methoxy-4-(1-methyl-1H-1,2,4-triazol-3-yl)pyridin-2-yl]amino}-N—($^2$H$_3$)methyl-6-propanamidopyridazine-3-carboxamide, methyl N-(5-{[3-methoxy-4-(1-methyl-1H-1,2,4-triazol-3-yl)pyridin-2-yl]amino}-6-[($^2$H$_3$)methylcarbamoyl]pyridazin-3-yl)carbamate, 6-(2-cyclopropylacetamido)-4-{[3-methoxy-4-(1-methyl-1H-1,2,4-triazol-3-yl)pyridin-2-yl]amino}-N—($^2$H$_3$)methylpyridazine-3-carboxamide, 4-{[3-methoxy-4-(1-methyl-1H-1,2,4-triazol-3-yl)pyridin-2-yl]amino}-N—($^2$H$_3$)methyl-6-[(4-methylpyridin-2-yl)amino]pyridazine-3-carboxamide, 4-{[3-methoxy-4-(1-methyl-1H-1,2,4-triazol-3-yl)pyridin-2-yl]amino}-6-[4-methoxypyridin-2-yl)amino]-N—($^2$H$_3$)methylpyridazine-3-carboxamide, 6-[(4-cyanopyridin-2-yl)amino]-4-{[3-methoxy-4-(1-methyl-1H-1,2,4-triazol-3-yl)pyridin-2-yl]amino}-N—($^2$H$_3$)methylpyridazine-3-carboxamide, 6-[(5-fluoropyridin-2-yl)amino]-4-{[3-methoxy-4-(1-methyl-1H-1,2,4-triazol-3-yl)pyridin-2-yl]amino}-N—($^2$H$_3$)methylpyridazine-3-carboxamide, 6-[(4,5-dimethylpyridin-2-yl)amino]-4-{[3-methoxy-4-(1-methyl-1H-1,2,4-triazol-3-yl)pyridin-2-yl]amino}-N—($^2$H$_3$)methylpyridazine-3-carboxamide, 6-[(5-fluoro-4-methylpyridin-2-yl)amino]-4-{[3-methoxy-4-(1-methyl-1H-1,2,4-triazol-3-yl)pyridin-2-yl]amino}-N—($^2$H$_3$)methylpyridazine-3-carboxamide, 6-[(4-ethylpyridin-2-yl)amino]-4-{[3-methoxy-4-(1-methyl-1H-1,2,4-triazol-3-yl)pyridin-2-yl]amino}-N—($^2$H$_3$)methylpyridazine-3-carboxamide, 4-{[3-methoxy-4-(1-methyl-1H-1,2,4-triazol-3-yl)pyridin-2-yl]amino}-N—($^2$H$_3$)methyl-6-{[5-(2-oxopyrrolidin-1-yl)pyridin-2-yl]amino}pyridazine-3-carboxamide, 6-[(4-fluoropyridin-2-yl)amino]-4-{[3-methoxy-4-(1-methyl-1H-1,2,4-triazol-3-yl)pyridin-2-yl]amino}-N—($^2$H$_3$)methylpyridazine-3-carboxamide, 4-{[3-methoxy-4-(1-methyl-1H-1,2,4-triazol-3-yl)pyridin-2-yl]amino}-N—($^2$H$_3$)methyl-6-[(5-methyl-1,3,4-thiadiazol-2-yl)amino]pyridazine-3-carboxamide, 6-[(4-chloropyridin-2-yl)amino]-4-{[3-methoxy-4-(1-methyl-1H-1,2,4-triazol-3-yl)pyridin-2-yl]amino}-N—($^2$H$_3$)methylpyridazine-3-carboxamide, 6-[(5-chloro-4-methylpyridin-2-yl)amino]-4-{[3-methoxy-4-(1-methyl-1H-1,2,4-triazol-3-yl)pyridin-2-yl]amino}-N—($^2$H$_3$)methylpyridazine-3-carboxamide, 6-[(4-chloro-5-methylpyridin-2-yl)amino]-4-{[3-methoxy-4-(1-methyl-1H-1,2,4-triazol-3-yl)pyridin-2-yl]amino}-N—($^2$H$_3$)methylpyridazine-3-carboxamide, 4-{[3-methoxy-4-(1-methyl-1H-1,2,4-triazol-3-yl)pyridin-2-yl]amino}-N—($^2$H$_3$)methyl-6-({2-oxo-2H-[1,3'-bipyridine]-6'-yl}amino)pyridazine-3-carboxamide, 6-{[4-(2-hydroxypropan-2-yl)pyridin-2-yl]amino}-4-{[3-methoxy-4-(1-methyl-1H-1,2,4-triazol-3-yl)pyridin-2-yl]amino}-N—($^2$H$_3$)methylpyridazine-3-carboxamide, 4-{[3-methoxy-4-(1-methyl-1H-1,2,4-triazol-3-yl)pyridin-2-yl]amino}-N—($^2$H$_3$)methyl-6-{[2-oxo-3-(trifluoromethyl)-2H-[1,3'-bipyridine]-6'-yl]amino}pyridazine-3-carboxamide, 4-{[3-methoxy-4-(1-methyl-1H-1,2,4-triazol-3-yl)pyridin-2-yl]amino}-6-[(6-methoxypyridin-2-yl)amino]-N—($^2$H$_3$)methylpyridazine-3-carboxamide, 4-{[3-methoxy-4-(1-methyl-1H-1,2,4-triazol-3-yl)pyridin-2-yl]amino}-N—($^2$H$_3$)methyl-6-(phenylamino)pyridazine-3-carboxamide, 6-[(4-acetylpyridin-2-yl)amino]-4-{[3-methoxy-4-(1-methyl-1H-1,2,4-triazol-3-yl)pyridin-2-yl]amino}-N—($^2$H$_3$)methylpyridazine-3-carboxamide, 6-({5-chloro-2-oxo-2H-[1,3'-bipyridine]-6'-yl}amino)-4-{[3-methoxy-4-(I-methyl-1H-1,2,4-triazol-3-yl)pyridin-2-yl]amino}-N—($^2$H$_3$)methylpyridazine-3-carboxamide, 4-{[3-methoxy-4-(1-methyl-1H-1,2,4-triazol-3-yl)pyridin-2-yl]amino}-N—($^2$H$_3$)methyl-6-({[1,3]thiazolo[5,4-b]pyridin-5-yl}amino)pyridazine-3-carboxamide, 4-{[3-methoxy-4-(1-methyl-1H-1,2,4-triazol-3-yl)pyridin-2-yl]amino}-N—($^2$H$_3$)methyl-6-{[4-(trifluoromethyl)pyridin-2-yl]amino}pyridazine-3-carboxamide, 6-{[5-(2-hydroxypropan-2-yl)pyridin-2-yl]amino}-4-{[3-methoxy-4-(1-methyl-1H-1,2,4-triazol-3-yl)pyridin-2-yl]amino}-N—($^2$H$_3$)methylpyridazine-3-carboxamide, 6-[(4-fluorophenyl)amino]-4-{[3-methoxy-4-(1-methyl-1H-1,2,4-triazol-3-yl)pyridin-2-yl]amino}-N—($^2$H$_3$)methylpyridazine-3-carboxamide, 4-{[3-methoxy-4-(1-methyl-1H-1,2,4-triazol-3-yl)pyridin-2-yl]amino}-N—($^2$H$_3$)methyl-6-[(pyridin-4-yl)amino]pyridazine-3-carboxamide, 6-[(6-ethoxypyridazin-3-yl)amino]-4-{[3-methoxy-4-(1-methyl-1H-1,2,4-triazol-3-yl)pyridin-2-yl]amino}-N—($^2$H$_3$)methylpyridazine-3-carboxamide, 6-{[5-(3-tert-butyl-2-oxoimidazolidin-1-yl)pyridin-2-yl]amino}-4-{[3-methoxy-4-(1-methyl-1H-1,2,4-triazol-3-yl)pyridin-2-yl]amino}-N—($^2$H$_3$)methylpyridazine-3-carboxamide, 4-{[3-methoxy-4-(1-methyl-1H-1,2,4-triazol-3-yl)pyridin-2-yl]amino}-N—($^2$H$_3$)methyl-6-{[5-(morpholin-4-yl)pyridin-2-yl]amino}pyridazine-3-carboxamide, 6-[(4,5-difluoropyridin-2-yl)amino]-4-{[3-methoxy-4-(1-methyl-1H-1,2,4-triazol-3-yl)pyridin-2-yl]amino}-N—($^2$H$_3$)methylpyridazine-3-carboxamide, 4-{[3-methoxy-4-(1-methyl-1H-1,2,4-triazol-3-yl)pyridin-2-yl]amino}-N—($^2$H$_3$)methyl-6-[(6-methylpyridin-2-yl)amino]pyridazine-3-carboxamide, 6-cyclopropaneamido-4-{[3-methoxy-4-(5-methyl-1,2,4-oxadiazol-3-yl)pyridin-2-yl]amino}-N—($^2$H$_3$)methylpyridine-3-carboxamide, 4-[(3-methoxy-4-{5-[(morpholin-4-yl)methyl]-1,2,4-oxadiazol-3-yl}pyridin-2-yl)amino]-N—($^2$H$_3$)methy-6-[(4-methylpyridin-2-yl)amino]pyridazine-3-carboxamide, 4-{[3-methoxy-4-(5-methyl-1,2,4-oxadiazol-3-yl)pyridin-2-yl]amino}-N—($^2$H$_3$)methy-6-propanamidopyridine-3-carboxamide, 6-(2-cyclopropylacetamido)-4-{[3-methoxy-4-(5-methyl-1,2,4-oxadiazol-3-yl)pyridin-2-yl]amino}-N—($^2$H$_3$)methylpyridine-3-carboxamide, 6-cyclopropaneamido-4-({3-methoxy-4-[5-(methoxymethyl)-1,2,4-oxadiazol-3-yl]pyridin-2-yl}amino)-N—($^2$H$_3$)methylpyridine-3-carboxamide, 6-cyclopropaneamido-4-({4-[5-(ethoxymethyl)-1,2,4-oxadiazol-3-yl]-3-methoxypyridin-2-yl}amino)-N—($^2$H$_3$)methylpyridine-3-carboxamide, 6-cyclopropaneamido-4-[(3-methoxy-4-{5-[(propan-2-yloxy)methyl]-1,2,4-oxadiazol-3-yl}pyridin-2-yl)amino]-N—($^2$H$_3$)methylpyridine-3-carboxamide, 4-({3-methoxy-4-[5-(methoxymethyl)-1,2,4-oxadiazol-3-yl]pyridin-2-yl}amino)-N—($^2$H$_3$)methyl-6-propanamidopyridine-3-carboxamide, 4-({4-[5-(ethoxymethyl)-1,2,4-oxadiazol-3-yl]-3-methoxypyridin-2-yl}amino)-N—($^2$H$_3$)methyl-6-propanamidopyridine-3-carboxamide, 6-cyclopropaneamido-4-({3-methoxy-4-[5-(methoxymethyl)-1,2,4-oxadiazol-3-yl]pyridin-2-yl}amino)-N—($^2$H$_3$)methylpyridazine-3-carboxamide, 4-[(4-cyano-3-methoxypyridin-2-yl)amino]-6-cyclopropaneamido-N—($^2$H$_3$)methylpyridazine-3-carboxamide, methyl N-{5-[(3-methoxy-4-{5-[(N-methylmethanesulfonamido)methyl]-1,2,4-oxadiazol-3-yl}pyridin-2-yl)amino]-6-[($^2$H$_3$)methylcarbamoyl]pyridazin-3-yl}carbamate, methyl N-{5-[(3-methoxy-4-{5-[(morpholin-4-yl)methyl]-1,2,4-oxadiazol-3-yl}pyridin-2-yl)amino]-6-[($^2$H$_3$)methylcarbamoyl]pyridazin-3-yl}carbamate, 6-cyclopropaneamido-4-[(3-methoxy-4-{5-[(N-methylmethanesulfonamido)methyl]-1,2,4-oxadiazol-3-yl}pyridin-2-yl)amino]-N—($^2$H$_3$)methylpyridazine-3-carboxamide, 6-cyclopropaneamido-4-[(3-methoxy-4-{5-[(morpholin-4-yl)methyl]-1,2,4-oxadiazol-3-yl}pyridin-2-yl)amino]-N—($^2$H$_3$)methylpyridazine-3-carboxamide, methyl N-(5-{[3-methoxy-4-(5-methyl-1,2,4-oxadiazol-3-yl)pyridin-2-yl]amino}-6-[($^2$H$_3$)methylcarbamoyl]pyridazin-3-yl)carbamate, 6-cyclopropaneamido-4-[(4-{5-[(1S)-1-hydroxyethyl]-1,2,4-oxadiazol-3-yl}-3-methoxypyridin-2-yl)amino]-N—($^2$H$_3$)methylpyridazine-3-carboxamide, 6-cyclopropaneamido-4-[(4-{5-[(dimethylamino)methyl]-1,2,4-oxadiazol-3-yl}-3-methoxypyridin-2-yl)amino]-N—($^2$H$_3$)methylpyridazine-3-carboxamide, 6-cyclopropaneamido-4-[(3-methoxy-4-{5-[(methylamino)methyl]-1,2,4-oxadiazol-3-yl}pyridin-2-yl)amino]-N—($^2$H$_3$)methylpyridazine-3-carboxamide, 4-({4-[5-(cyanomethyl)-1,2,4-oxadiazol-3-yl]-3-methoxypyridin-2-yl}amino)-6-cyclopropaneamido-N—($^2$H$_3$)methylpyridazine-3-carboxamide, 4-[(3-methoxy-4-{5-[(N-methylmethanesulfonamido)methyl]-1,2,4-oxadiazol-3-yl}pyridin-2-yl)amino]-N—($^2$H$_3$)methyl-6-[(4-methylpyridin-2-yl)amino]pyridazine-3-carboxamide, 4-({3-methoxy-4-[5-(methoxymethyl)-1,2,4-oxadiazol-3-yl]pyridin-2-yl}amino)-N—($^2$H$_3$)methyl-6-[(4-methylpyridin-2-yl)amino]pyridazine-3-carboxamide, 4-((3-methoxy-4-(5-(morpholinomethyl)-1,2,4-oxadiazol-3-yl)pyridin-2-yl)amino)-N-(methyl-d3)-6-((4-methylpyridin-2-yl)amino)pyridazine-3-carboxamide, methyl N-{5-[(4-{5-[(1,1-dioxo-1λ$^6$,2-thiazinan-2-yl)methyl]-1,2,4-oxadiazol-3-yl}-3-methoxypyridin-2-yl)amino]-6-[($^2$H$_3$)methylcarbamoyl]pyridazin-3-yl}carbamate, 4-[(3-methoxy-4-{5-[(morpholin-4-yl)methyl]-1,2,4-oxadiazol-3-yl}pyridin-2-yl)amino]-N—($^2$H$_3$)methyl-6-propanamidopyridazine-3-carboxamide, 4-({3-methoxy-4-[5-(methoxymethyl)-1,2,4-oxadiazol-3-yl]pyridin-2-yl}amino)-N—($^2$H$_3$)methyl-6-propanamidopyridazine-3-carboxamide, 6-(2-cyclopropylacetamido)-4-[(3-methoxy-4-{5-[(N-methylmethanesulfonamido)methyl]-1,2,4-oxadiazol-3-yl}pyridin-2-yl)amino]-N—($^2$H$_3$)methylpyridazine-3-carboxamide, 4-({3-methoxy-4-[5-(methoxymethyl)-1,2,4-oxadiazol-3-yl]pyridin-2-yl}amino)-N—($^2$H$_3$)methyl-6-(3-methylbutanamido)pyridazine-3-carboxamide, 4-[(3-methoxy-4-{5-[(morpholin-4-yl)methyl]-1,2,4-oxadiazol-3-yl}pyridin-2-yl)amino]-N—($^2$H$_3$)methyl-6-(3-methylbutanamido)pyridazine-3-carboxamide, 4-[(3-methoxy-4-{5-[(N-methylmethanesulfonamido)methyl]-1,2,4-oxadiazol-3-yl}pyridin-2-yl)amino]-N—($^2$H$_3$)methyl-6-(3-methylbutanamido)pyridazine-3-carboxamide, 4-[(3-methoxy-4-{5-[(2-oxo-1,3-oxazolidin-3-yl)methyl]-1,2,4-oxadiazol-3-yl}pyridin-2-yl)amino]-N—($^2$H$_3$)methyl-6-(3-methylbutanamido)pyridazine-3-carboxamide, 6-(2-cyclopropylacetamido)-4-({3-methoxy-4-[5-(methoxymethyl)-1,2,4-oxadiazol-3-yl]pyridin-2-yl}amino)-N—($^2$H$_3$)methylpyridazine-3-carboxamide, 6-(2-cyclopropylacetamido)-4-({4-[5-(hydroxymethyl)-1,2,4-oxadiazol-3-yl]-3-methoxypyridin-2-yl}amino)-N—($^2$H$_3$)methylpyridazine-3-carboxamide, 6-cyclopropaneamido-4-{[3-methoxy-4-(5-methyl-1,2,4-oxadiazol-3-yl)pyridin-2-yl]amino}-N—($^2$H$_3$)methylpyridazine-3-carboxamide 6-(2-cyclopropylacetamido)-4-{[3-methoxy-4-(5-methyl-1,2,4-oxadiazol-3-yl)pyridin-2-yl]amino}-N—($^2$H$_3$)methylpyridazine-3-carboxamide, 4-({3-methoxy-4-[5-(methoxymethyl)-1,2,4-oxadiazol-3-yl]pyridin-2-yl}amino)-N—($^2$H$_3$)methyl-6-[2-(oxetan-3-yl)acetamido]pyridazine-3-carboxamide, 6-[(5-chloro-4-methylpyridin-2-yl)amino]-4-{[3-methoxy-4-(5-methyl-1,2,4-oxadiazol-3-yl)pyridin-2-yl]amino}-N—($^2$H$_3$)methylpyridazine-3-carboxamide, 4-{[3-methoxy-4-(5-methyl-1,2,4-oxadiazol-3-yl)pyridin-2-yl]amino}-N—($^2$H$_3$)methyl-6-[(4-methylpyridin-2-yl)amino]pyridazine-3-carboxamide, 4-{[3-methoxy-4-(5-methyl-1,2,4-oxadiazol-3-yl)pyridin-2-yl]amino}-N—($^2$H$_3$)methyl-6-[(6-methyl pyrimidin-4-yl)amino]pyridazine-3-carboxamide, 6-{[4-(2-hydroxypropan-2-yl)pyridin-2-yl]amino}-4-{[3-methoxy-4-(5-methyl-1,2,4-oxadiazol-3-yl)pyridin-2-yl]amino}-N—($^2$H$_3$)methylpyridazine-3-carboxamide, 4-{[3-methoxy-4-(5-methyl-1,2,4-oxadiazol-3-yl)pyridin-2-yl]amino}-N—($^2$H$_3$)methyl-6-propanamidopyridazine-3-carboxamide, 6-{[5-(2-hydroxypropan-2-yl)pyridin-2-yl]amino}-4-{[3-methoxy-4-(5-methyl-1,2,4-oxadiazol-3-yl)pyridin-2-yl]amino}-N—($^2$H$_3$)methylpyridazine-3-carboxamide 6-cyclopropaneamido-4-({3'-methoxy-[2,4'-bipyridine]-2'-yl}amino)-N—($^2$H$_3$)methylpyridazine-3-carboxamide, 6-cyclopropaneamido-4-({3'-methoxy-[2,4'-bipyridine]-2'-yl}amino)-N—($^2$H$_3$)methylpyridine-3-carboxamide, 6-cyclopropaneamido-4-({5-cyclopropaneamido-3'-methoxy-[2,4'-bipyridine]-2'-yl}amino)-N—($^2$H$_3$)methylpyridine-3-carboxamide, 4-({5-chloro-3'-methoxy-[2,4'-bipyridine]-2'-yl}amino)-6-cyclopropaneamido-N—($^2$H$_3$)methylpyridine-3-carboxamide, 6-cyclopropaneamido-4-({4-[5-(dimethylcarbamoyl)pyrazin-2-yl]-3-methoxypyridin-2-yl}amino)-N—($^2$H$_3$)methylpyridazine-3-carboxamide, 6-cyclopropaneamido-4-[(4-{5-[ethyl(methyl)carbamoyl]pyrazin-2-yl}-3-methoxypyridin-2-yl)amino]-N—($^2$H$_3$)methylpyridazine-3-carboxamide, 6-(2-cyclopropylacetamido)-4-({4-[5-(dimethylcarbamoyl)pyrazin-2-yl]-3-methoxypyridin-2-yl}amino)-N—($^2$H$_3$)methylpyridazine-3-carboxamide, 4-({4-[5-(dimethylcarbamoyl)pyrazin-2-yl]-3-methoxypyridin-2-yl}amino)-N—($^2$H$_3$)methyl-6-[(1-methyl-1H-pyrazol-3-yl)amino]pyridazine-3-carboxamide, 6-[(1,5-dimethyl-1H-pyrazol-3-yl)amino]-4-({4-[5-(dimethylcarbamoyl)pyrazin-2-yl]-3-methoxypyridin-2-yl}amino)-N—($^2$H$_3$)methylpyridazine-3-carboxamide, 6-[(5-chloro-1-methyl-1H-pyrazol-3-yl)amino]-4-({4-[5-(dimethylcarbamoyl)pyrazin-2-yl]-3-methoxypyridin-2-yl}amino)-N—($^2$H$_3$)methylpyridazine-3-carboxamide, 4-{[4-(5-fluoropyrimidin-2-yl)-3-methoxypyridin-2-yl]amino}-6-{[5-(2-hydroxypropan-2-yl)pyridin-2-yl]amino}-N—($^2$H$_3$)methylpyridazine-3-carboxamide, 6-{[5-(2-aminopropan-2-yl)pyridin-2-yl]amino}-4-{[4-(5-fluoropyrimidin-2-yl)-3-methoxypyridin-2-yl]amino}-N—($^2$H$_3$)methylpyridazine-3-carboxamide, 4-{[4-(5-fluoropyrimidin-2-yl)-3-methoxypyridin-2-yl]amino}-N—($^2$H$_3$)methyl-6-[(5-methylpyrazin-2-yl)amino]pyridazine-3-carboxamide, 6-[(6-ethoxypyridazin-3-yl)amino]-4-{[4-(5-fluoropyrimidin-2-yl)-3-methoxypyridin-2-yl]amino}-N—($^2$H$_3$)methylpyridazine-3-carboxamide, 4-{[4-(5-fluoropyrimidin-2-yl)-3-methoxypyridin-2-yl]amino}-N—($^2$H$_3$)methyl-6-{[5-(morpholin-4-yl)pyridin-2-yl]amino}pyridazine-3-carboxamide, 6-[(4-fluoropyridin-2-yl)amino]-4-{[4-(5-fluoropyrimidin-2-yl)-3-methoxypyridin-2-yl]amino}-N—($^2$H$_3$)methylpyridazine-3-carboxamide, 4-{[4-(5-fluoropyrimidin-2-yl)-3-methoxypyridin-2-yl]amino}-N—($^2$H$_3$)methyl-6-[(4-methylpyridin-2-yl)amino]pyridazine-3-carboxamide, 4-{[4-(5-fluoropyrimidin-2-yl)-3-methoxypyridin-2-yl]amino}-6-[(6-methoxypyridazin-3-yl)amino]-N—($^2$H$_3$)methylpyridazine-3-carboxamide, 4-{[4-(5-fluoropyrimidin-2-yl)-3-methoxypyridin-2-yl]amino}-N—($^2$H$_3$)methyl-6-[(pyridin-2-yl)amino]pyridazine-3-carboxamide, 6-cyclopropaneamido-4-{[4-(5-fluoropyrimidin-2-yl)-3-methoxypyridin-2-yl]amino}-N—($^2$H$_3$)methylpyridazine-3-carboxamide, 4-{[3-methoxy-4-(2-methyl-2H-1,2,3,4-tetrazol-5-yl)pyridin-2-yl]amino}-N—($^2$H$_3$)methyl-6-[(4-methylpyridin-2-yl)amino]pyridine-3-carboxamide, methyl N-(4-{[3-methoxy-4-(2-methyl-2H-1,2,3,4-tetrazol-5-yl)pyridin-2-yl]amino}-5-[($^2$H$_3$)methylcarbamoyl]pyridin-2-yl)carbamate, 4-{[3-methoxy-4-(2-methyl-2H-1,2,3,4-tetrazol-5-yl)pyridin-2-yl]amino}-N—($^2$H$_3$)methyl-6-propanamidopyridine-3-carboxamide, or 6-[(4-cyanopyridin-2-yl)amino]-4-{[3-methoxy-4-(2-methyl-2H-1,2,3,4-tetrazol-5-yl)pyridin-2-yl]amino}-N—($^2$H$_3$)methylpyridine-3-carboxamide, or a stereoisomer or pharmaceutically acceptable salt thereof.

In another embodiment, there is provided a pharmaceutical composition comprising one or more compounds of formula I and a pharmaceutically acceptable carrier or diluent.

The present invention is also directed to pharmaceutical compositions useful in treating diseases associated with the modulation of IL-12, IL-23 and/or IFNα by acting on Tyk-2 to cause signal transduction inhibition, comprising compounds of formula I, or pharmaceutically-acceptable salts thereof, and pharmaceutically-acceptable carriers or diluents.

The invention further relates to methods of treating diseases associated with the modulation of IL-12, IL-23, and/or IFNα, comprising administering to a patient in need of such treatment a therapeutically-effective amount of a compound according to formula I.

The present invention also provides processes and intermediates for making the compounds of the present invention.

The present invention also provides a method for treating proliferative, metabolic, allergic, autoimmune and inflammatory diseases (or use of the compounds of the present invention for the manufacture of a medicament for the treatment of these diseases), comprising administering to a host in need of such treatment a therapeutically effective amount of at least one of the compounds of the present invention.

The present invention also provides a method of treating an inflammatory or autoimmune disease (or use of the compounds of the present invention for the manufacture of a medicament for the treatment of these diseases) comprising administering to a patient in need of such treatment a therapeutically-effective amount of a compound of Formula I.

The present invention also provides a method for treating a disease (or use of the compounds of the present invention for the manufacture of a medicament for the treatment of these diseases), comprising administering to a patient in need of such treatment a therapeutically-effective amount of a compound of Formula I, wherein the disease is rheumatoid arthritis, multiple sclerosis, systemic lupus erythematosus (SLE), lupus nephritis, cutaneous lupus, inflammatory bowel disease, psoriasis, Crohn's Disease, psoriatic arthritis, Sjögren's syndrome, systemic scleroderma, ulcerative colitis, Graves' disease, discoid lupus erythematosus, adult onset Stills, systemic onset juvenile idiopathic arthritis, gout, gouty arthritis, type 1 diabetes, insulin dependent diabetes mellitus, sepsis, septic shock, Shigellosis, pancreatitis (acute or chronic), glomerulonephritis, autoimmune gastritis, diabetes, autoimmune hemolytic anemia, autoimmune neutropenia, thrombocytopenia, atopic dermatitis, myasthenia gravis, pancreatitis (acute or chronic), ankylosing spondylitis, pemphigus vulgaris, Goodpasture's disease, antiphospholipid syndrome, idiopathic thrombocytopenia, ANCA-associated vasculitis, pemphigus, Kawasaki disease, Chronic Inflammatory Demyelinating Polyneuropathy (CIDP), dermatomyositis, polymyositis, uveitis, Guillain-Barre syndrome, autoimmune pulmonary inflammation, autoimmune thyroiditis, autoimmune inflammatory eye disease, and chronic demyelinating polyneuropathy.

The present invention also provides a method of treating an inflammatory or autoimmune disease (or use of the compounds of the present invention for the manufacture of a medicament for the treatment of said diseases), comprising administering to a patient in need of such treatment a therapeutically-effective amount of a compound of Formula I, wherein the disease is selected from systemic lupus erythematosus (SLE), lupus nephritis, cutaneous lupus, Crohn's Disease, ulcerative colitis, type 1 diabetes, psoriasis, rheumatoid arthritis, systemic onset juvenile idiopathic arthritis, ankylosing spondylitis, and multiple sclerosis.

The present invention also provides a method for treating a rheumatoid arthritis (or use of the compounds of the present invention for the manufacture of a medicament for the treatment of rheumatoid arthritis, comprising administering to a patient in need of such treatment a therapeutically-effective amount of a compound of Formula I.

In addition, the present invention also provides a method of treating a condition (or use of the compounds of the present invention for the manufacture of a medicament for the treatment of these conditions) comprising administering to a patient in need of such treatment a therapeutically-effective amount of a compound of Formula I, wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evans syndrome, hemolytic uremic syndromethrombotic thrombocytopenic purpura (HUS/TTP), sarcoidosis, Sjögren's syndrome, peripheral neuropathies, pemphigus vulgaris and asthma.

The present invention also provides a method of treating an IL-12, IL-23, and/or IFNα mediated disease (or use of the compounds of the present invention for the manufacture of a medicament for the treatment of these diseases), comprising administering to a patient in need of such treatment a therapeutically-effective amount of a compound of formula I.

The present invention also provides a method of treating an IL-12, IL-23 and/or IFNα mediated disease (or use of the compounds of the present invention for the manufacture of a medicament for the treatment of these diseases), comprising administering to a patient in need of such treatment a therapeutically-effective amount of a compound of formula I, wherein the IL-12, IL-23 and/or IFNα mediated disease is a disease modulated by IL-12, IL-23 and/or IFNα.

The present invention also provides a method of treating diseases, comprising administering to a patient in need of such treatment a therapeutically-effective amount of a compound of formula I in combination with other therapeutic agents.

The present invention also provides the compounds of the present invention for use in therapy.

In another embodiment, compounds of formula I are selected from exemplified compounds or combinations of exemplified compounds or other embodiments herein.

In another embodiment are compounds having an $IC_{50}$<1000 nM in at least one of the assays described below.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C═N double bonds, and the like can also be present in the compounds, and all such stable isomers are contemplated in the present invention. Cis- and trans-geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —CONH$_2$ is attached through the carbon atom.

The term "optionally substituted" in reference to a particular moiety of the compound of Formula I (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound".

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example. "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "CO$_2$" is used herein, this is intended to refer to the group

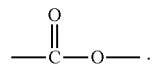

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, $S(O)_2H$, or $S(O)H$ group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane. [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula I, the term "cycloalkyl" includes cyclopropyl, cyclobutyl, cyclopentyl, cyclohexyl, cycloheptyl, bicyclooctyl, etc., as well as the following ring systems:

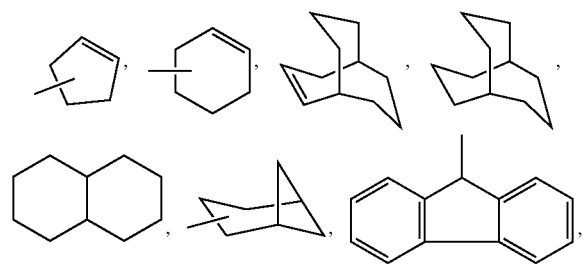

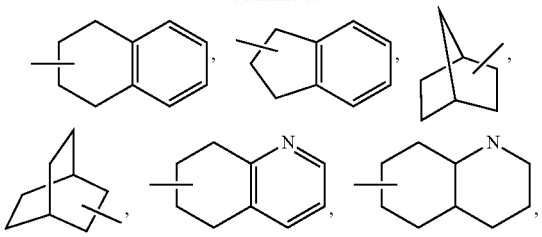

and the like, which optionally may be substituted at any available atoms of the ring(s). Preferred cycloalkyl groups include cyclopropyl, cyclopentyl, cyclohexyl, and

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

Thus, examples of aryl groups include:

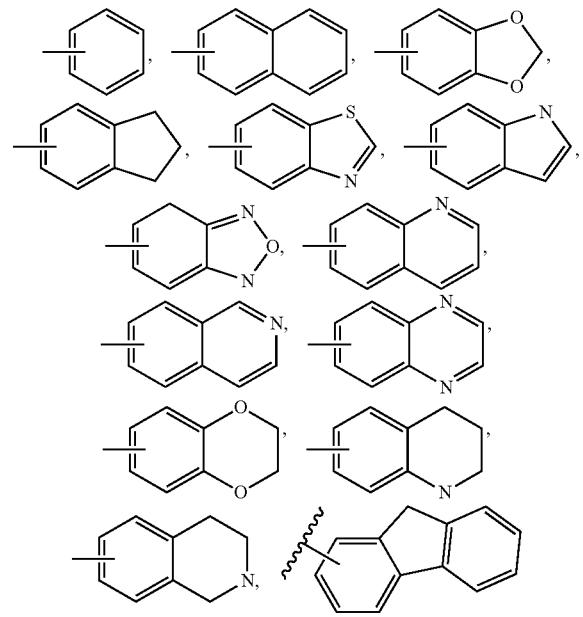

(fluorenyl) and the like, which optionally may be substituted at any available carbon or nitrogen atom. A preferred aryl group is optionally-substituted phenyl.

The terms "heterocycle", "heterocycloalkyl", "heterocyclo", "heterocyclic", or "heterocyclyl" may be used interchangeably and refer to substituted and unsubstituted 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or fully unsaturated. The heterocyclo group may be attached at any available nitrogen or carbon atom. As used herein the terms "heterocycle", "heterocycloalkyl", "heterocyclo", "heterocyclic", and "heterocycyl" include "heteroaryl" groups, as defined below.

In addition to the heteroaryl groups described below, exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional monocyclic heterocyclyl groups include

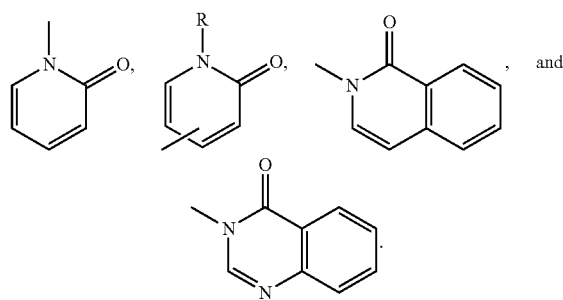

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, fluoropyridyl, dihydroisoindolyl, tetrahydroquinolinyl and the like.

Exemplary tricyclic heteroaryl groups include carbazolyl, benzindolyl, phenanthrolinyl, acridinyl, phenanthridinyl, xanthenyl and the like.

In compounds of formula I, preferred heteroaryl groups include:

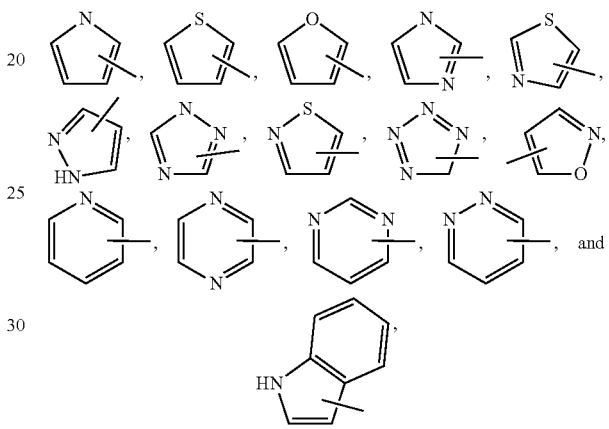

and L, and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0 to 2, substituents selected from those recited above for the aryl, cycloalkyl, heterocyclo and/or heteroaryl groups, as appropriate.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula I may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s)" may include zwitterions (inner salts), e.g., when a compound of formula I, contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula I may be formed for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically-acceptable salts" refer to derivatives of the disclosed compounds wherein the parent compound is modified by making acid or base salts thereof. Examples of pharmaceutically-acceptable salts include, but are not limited to, mineral or organic acid salts of basic groups such as amines; and alkali or organic salts of acidic groups such as carboxylic acids. The pharmaceutically-acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically-acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula I, and/or a salt and/or solvate thereof. Any compound that will be converted in vivo to provide the bioactive agent (i.e., the compound for formula I) is a prodrug within the scope and spirit of the invention. For example, compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) Bundgaard, H., ed., *Design of Prodrugs*, Elsevier (1985), and Widder, K. et al., eds., *Methods in Ezymology*, 112: 309-396, Academic Press (1985);
b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and
c) Bundgaard, H., *Adv. Drug Deliv. Rev.*, 8:1-38 (1992), each of which is incorporated herein by reference.

Compounds of the formula I and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention. Additionally, inventive compounds may have trans- and cis-isomers.

It should further be understood that solvates (e.g., hydrates) of the compounds of Formula I are also with the scope of the present invention. Methods of solvation are generally known in the art.

Utility

The compounds of the invention modulate IL-23-stimulated and IFNα-stimulated cellular functions, including gene transcription. Other types of cellular functions that may be modulated by the compounds of the instant invention include, but are not limited to, IL-12-stimulated responses.

Accordingly, compounds of formula I have utility in treating conditions associated with the modulation of the function of IL-23 or IFNα, and particularly the selective inhibition of function of IL-23, IL-12 and/or IFNα, by acting on Tyk2 to mediate signal transduction. Such conditions include IL-23-, IL-12-, or IFNα-associated diseases in which pathogenic mechanisms are mediated by these cytokines.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as modulators of IL-23-, IL-12 and IFNα-stimulated cellular responses, compounds of Formula I are useful in treating IL-23-, IL-12- or IFNα-associated diseases including, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, cutaneous lupus, lupus nephritis, discoid lupus erythematosus, psoriasis; auto-inflammatory diseases including CAPS, TRAPS, FMF, adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder: proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma. Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, cutaneous lupus, lupus nephritis, discoid lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis. Reiter's syndrome, gout, traumatic arthritis, rubella arthritis, acute synovitis, pancreatic R-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis:

Alzheimer's disease, Parkinson's disease, cerebral ischemias or neurodegenerative disease caused by traumatic injury: angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia [should this be hypoxia], vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's disease, ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

When the terms "IL-23-, IL-12- and/or IFNα-associated condition" or "IL-23-, IL-12- and/or IFNα-associated disease or disorder" are used herein, each is intended to encompass all of the conditions identified above as if repeated at length, as well as any other condition that is affected by IL-23, IL-12 and/or IFNα.

The present invention thus provides methods for treating such conditions, comprising administering to a subject in need thereof a therapeutically-effective amount of at least one compound of Formula I or a salt thereof. "Therapeutically effective amount" is intended to include an amount of a compound of the present invention that is effective when administered alone or in combination to inhibit IL-23, IL-12 and/or IFNα function and/or treat diseases.

The methods of treating IL-23-, IL-12 and/or IFNα-associated conditions may comprise administering compounds of Formula I alone or in combination with each other and/or other suitable therapeutic agents useful in treating such conditions. Accordingly, "therapeutically effective amount" is also intended to include an amount of the combination of compounds claimed that is effective to inhibit IL-23, IL-12 and/or IFNα function and/or treat diseases associated with IL-23. IL-12 and/or IFNα.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG): non-steroidal anti-inflammatory drugs (NSAIDs) such as ibuprofen, celecoxib and rofecoxib: steroids such as prednisone or dexamethasone: antiviral agents such as abacavir: antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating IL-23-, IL-12- or IFNα-associated conditions by inhibiting Tyk2-mediated signal transduction, including IL-23-, IL-12- and/or IFNα-mediated diseases, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula I and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered: the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

The compounds of Formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg: 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species that are affected by modulation of IL-23, IL-12 and/or IFNα-mediated functions.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter.

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

In the Examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared). Columnchromatographywasperformedwithpre-packedsilicagelcartridges using an Isco medium pressure chromatography apparatus (Teledyne Corporation), eluting with the solvent or solvent mixture indicated. The following abbreviations are used:

| Abbreviations | |
|---|---|
| Abbreviation | Meaning |
| Ac | acetyl |
| ACN | acetonitrile |
| AcOH | acetic acid |
| anhyd. | anhydrous |
| aq. | aqueous |
| Bn | benzyl |
| Bu | butyl |
| Boc | tert-butoxycarbonyl |
| BOP | benzotriazol-1-yloxytris-(dimethylamino)-phosphonium hexafluorophosphate |
| CV | Column Volumes |
| DCE | dichloroethane |
| DCM | dichloromethane |
| DIPEA | diisopropylethylamine |
| DMF | dimethylformamide |
| DMSO | dimethylsulfoxide |
| EtOAc | ethyl acetate |
| Et | ethyl |

-continued

Abbreviations

| Abbreviation | Meaning |
| --- | --- |
| EtOH | ethanol |
| H or $H_2$ | hydrogen |
| h, hr or hrs | hour(s) |
| HATU | O-(7-azabenzotriazol-1-yl)-N,N,N',N'-tetramethyluronium hexafluorophosphate |
| hex | hexane |
| i | iso |
| IPA | isopropyl alcohol |
| ISCO | automated chromatography |
| HOAc | acetic acid |
| HCl | hydrochloric acid |
| HPLC | high pressure liquid chromatography |
| LC | liquid chromatography |
| LIHMDS | Lithium bis(trimethylsilyl)amide |
| M | molar |
| mM | millimolar |
| Me | methyl |
| MeOH | methanol |
| MHz | megahertz |
| min. | minute(s) |
| mins | minute(s) |
| M + 1 | (M + H)+ |
| MS | mass spectrometry |
| n or N | normal |
| nm | nanometer |
| nM | nanomolar |
| NMP | N-methylpyrrolidine |
| Pd/C | palladium on carbon |
| $PdCl_2(dppf)_2$ | [1,1'-bis(diphenylphosphino)ferrocene]dichloropalladium(II) |
| $Pd_2dba_3$ | Tris(dibenzylideneacetone)dipalladium(0) |
| Ph | phenyl |
| $PPh_3$ | triphenylphosphine |
| Pr | propyl |
| PSI | pounds per square inch |
| rb | round bottle |
| rt | room temperature |
| Ret Time | retention time |
| sat. | saturated |
| SEC | supercritical fluid chromatography |
| TEA | triethylamine |
| TFA | trifluoroacetic acid |
| THF | tetrahydrofuran |

Preparations

The preparations set out below are for the synthesis of reagents that were not obtained from commercial sources and were employed for the preparation of compounds of formula I of the invention. All chiral compounds in the Tables and Schemes are racemic unless specified otherwise.

Reverse-phase preparative high performance liquid chromatography ("HPLC") was performed with Shimadzu 8A liquid chromatographs using YMC S5 ODS columns (20× 100, 20×250, or 30×250 millimeter ("mm")). Gradient elution was performed with methanol ("MeOH")/water mixtures in the presence of 0.1% trifluoroacetic acid ("TFA").

HPLC Methods

Method A: (Analytical)

Column: Waters Acquity BEH $C_{18}$ 2.0×50 mm, 1.7 µm; mobile phase A: water with 0.1% TFA; mobile phase B: MeCN with 0.1% TFA; temperature: 40° C.; flow rate 1 mL/min; gradient: 0-100% B over 1.5 min, then 0.5 min isocratic at 100% B.

Method B: (Analytical)

Column: Acquity UPLC® BEH $C_{18}$ 2.1×50 mm, 1.7 µm (Waters Corp.); mobile phase A: water with 0.05% TFA; mobile phase B: MCN with 0.05% TFA; temperature: 50° C.; flow rate 0.8 mL/min; gradient: 0-100% B over 1.8 min.

Method C: (Analytical)

Column: Acquity UPLC® BEH $C_{18}$ 2.1×50 mm, 1.7 µm (Waters Corp.); mobile phase A: water with 0.1% TFA; mobile phase B: MeCN with 0.1% TFA; temperature: 50° C.; flow rate mL/min; gradient: 0-100% B over 3 min, then 0.5 min isocratic at 100% B.

Method D: (OC-ACN-AA-XB)

Waters Acquity UPLC BEH C18, 2.1×50 mm, 1.7-µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

Example 1

6-(cyclopropanecarboxamido)-4-((3-methoxy-4-(1-methyl-1H-1,2,4-triazol-3-yl)pyridin-2-yl)amino)-N-(methyl-d3)pyridazine-3-carboxamide

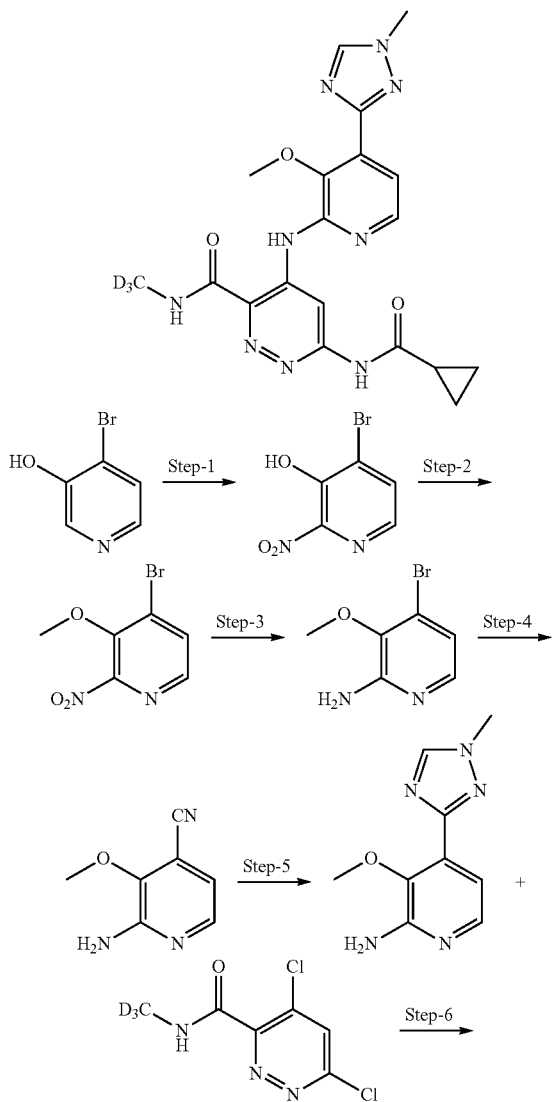

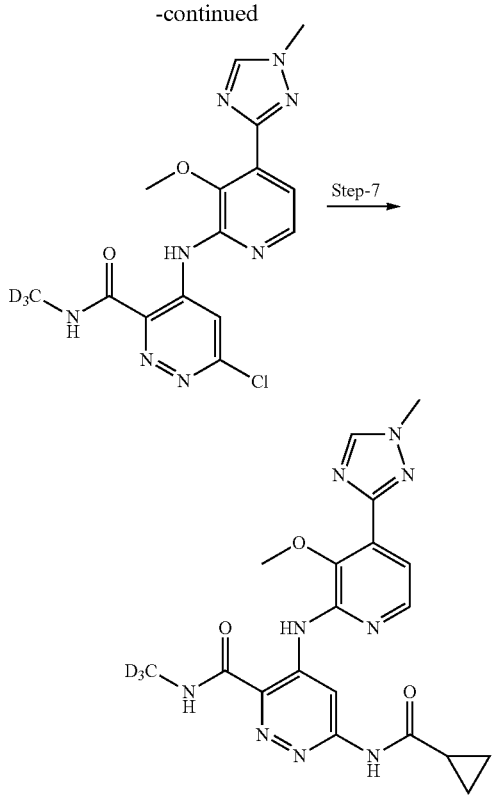

Step 1

4-Bromopyridin-3-ol (0.98 g, 5.63 mmol) was dissolved in concentrated sulfuric acid (3 mL), nitric acid (0.378 ml, 8.45 mmol) (fuming) was added under ice-cooling and the mixture was stirred for 20 hours. The reaction mixture was gently poured into ice water (40 mL) with stirring. The mixture was extracted with AcOEt (50 mL), which was washed with brine (30 mL), dried over Na$_2$SO$_4$ and concentrated under vacuo to give 4-bromo-2-nitropyridin-3-ol (0.45 g) which was used as is. LCMS m/z 219.1 (M+H)$^+$; HPLC ta 1.04 min (analytical HPLC Method A); $^1$H NMR (400 MHz, METHANOL-d$_4$) δ 8.01 (d, J=4.6 Hz, 1H), 7.95 (d, J=4.6 Hz, 1H).

Step 2

4-Bromo-2-nitropyridin-3-ol (400 mg, 1.827 mmol) was dissolved in DMF (5 mL). K$_2$CO$_3$ (505 mg, 3.65 mmol) was added and the mixture was stirred at rt for 10 min. then MeI (228 μl, 3.65 mmol) was added and the mixture was stirred at r for o/n. The reaction mixture was diluted with AcOEt (40 mL) and water (20 mL), the organic layer was separated and washed with sat. NaHCO$_3$ (2×20 mL), brine (20 mL), dried over Na$_2$SO$_4$ and concentrated under vacuo. The crude product was purified with ISCO column (12 g, AcOEt/Hexane=0-60%, gradient time=16 mm) to give 4-bromo-3-methoxy-2-nitropyridine (260 mg). LCMS m/z 233.1 (M+H)$^+$; HPLC t$_R$ 1.17 min (analytical HPLC Method A); $^1$H NMR (400 MHz, CHLOROFORM-d) δ 8.10 (d, J=5.1 Hz, 1H), 7.79 (d, J=5.1 Hz, 1H), 4.06 (s, 3H).

Step 3

4-Bromo-3-methoxy-2-nitropyridine (350 mg, 1.502 mmol) was dissolved in AcOH (1 mL), EtOH (1 mL) and water (0.5 mL), IRON (419 mg, 7.51 mmol) was added. After 1 h the LC-MS indicated the complete consumption of the sm and the mixture was filtered, the filtrate was diluted with AcOEt (50 mL), which was mixed with sat. NaHCO$_3$ and the organic layer was washed with brine (30 mL), dried over Na$_2$SO$_4$ and concentrated under vacuo to give the desired product which was used as is (300 mg). LCMS m/z 205.1 (M+H)$^+$; HPLC t$_R$ 0.66 min (analytical HPLC Method A); $^1$H NMR (400 MHz, METHANOL-d$_4$) δ 7.51 (d, J=5.7 Hz, 1H), 6.81 (d, J=5.5 Hz, 1H), 3.89-3.78 (m, 3H).

Step 4

4-Bromo-3-methoxypyridin-2-amine (100 mg, 0.493 mmol) was mixed with dicyanozinc (57.8 mg, 0.493 mmol), Pd$_2$(dba)$_3$ (18.04 mg, 0.020 mmol), DPPF (21.84 mg, 0.039 mmol), Zinc (3.86 mg, 0.059 mmol) in Acetamide (2 mL). The mixture was flushed with N$_2$ for a couple min and heated at 135° C. for o/n. LC-MS indicated the complete consumption of the starting material and the mixture was filtered, the filtrate was diluted with AcOEt (40 mL), which was washed with sat. NaHCO$_3$ (2×20 mL) and brine (20 mL), dried over Na$_2$SO$_4$ and concentrated under vacuo to give 2-amino-3-methoxyisonicotinonitrile which was purified with isco column (12 g, MeOH/DCM=0-15%, 12 min gradient) (45 mg of the desired product). LCMS m/z 150.3 (M+H)$^+$; HPLC t$_R$ 0.34 min (analytical HPLC Method A); $^1$H NMR (400 MHz, METHANOL-d$_4$) δ 7.80-7.67 (m, 1H), 6.79-6.71 (m, 1H), 4.06 (s, 3H).

Step 5

To 2-amino-3-methoxyisonicotinonitrile (100 mg, 0.670 mmol) and N-methylformohydrazide (174 mg, 2.347 mmol) in 5 mL of THF (55-60° C.) was added potassium tert-butoxide (2682 μl, 2.68 mmol). The mixture was stirred at 60° C. for 1 h. The mixture was mixed with 1 mL of MeOH, concentrated and purified with isco column (12 g, MeOH/DCM=0-10%, gradient time=12 min) to give 3-methoxy-4-(1-methyl-1H-1,2,4-triazol-3-yl)pyridin-2-amine (62 mg). LCMS m/z 206.3 (M+H)$^+$; HPLC ta 0.36 min (analytical HPLC Method A); $^1$H NMR (400 MHz, METHANOL-d$_4$) δ 8.50 (s, 1H), 7.74 (d, J=5.5 Hz, 1H), 7.10 (d, J=5.3 Hz, H), 4.03 (s, 3H), 3.75 (s, 3H).

Step 6

To a clear solution of 4,6-dichloro-N-(methyl-d3) pyridazine-3-carboxamide (61.1 mg, 0.292 mmol) and 3-methoxy-4-(1-methyl-1H-1,2,4-triazol-3-yl)pyridin-2-amine (60 mg, 0.292 mmol) in Tetrahydrofuran (10 mL) was added lithium bis(trimethylsilyl)amide (877 μl, 0.877 mmol) dropwise to cause color changing to dark amber, the mixture was stirred at rt for o/n. The reaction was quenched with addition of water (2 mL), and extracted with AcOEt (40 mL) and washed with brine (20 mL), the organic layer was dried over Na$_2$SO$_4$ and concentrated under vacuo and the residue was purified with ISCO column (12 g, AcOEt/Hexane=0-100% gradient time=12 min) to give 6-chloro-4-((3-methoxy-4-(1-methyl-1H-1,2,4-triazol-3-yl)pyridin-2-yl)amino)-N-(methyl-d3)pyridazine-3-carboxamide (50 mg). LCMS m/z 378.4 (M+H)$^+$; HPLC t$_R$ 1.01 min (analytical HPLC Method A); $^1$H NMR (400 MHz CHLOROFORM-d) δ 9.41-9.36 (m, 1H), 8.22-8.16 (m, 2H), 7.67-7.61 (m, 1H), 4.05 (d, J=13.4 Hz, 6H).

Step 7

A mixture of 6-chloro-4-((3-methoxy-4-(1-methyl-1H-1,2,4-triazol-3-yl)pyridin-2-yl)amino)-N-(methyl-d3) pyridazine-3-carboxamide (15 mg, 0.040 mmol), cyclopropanecarboxamide (6.76 mg, 0.079 mmol), xantphos (4.59 mg, 7.94 μmol), Cs₂CO₃ (25.9 mg, 0.079 mmol) and Pd₂(dba)₃ (3.64 mg, 3.97 μmol) in dioxane (1 mL) was sparged with nitrogen for 2 min., then it was stirred at 130° C. for 3 h. After cooling the mixture was diluted with DMSO and the crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 5-55% B over 20 minutes, then a 5-minute hold at 100% B; Flow: 20 mL/min. Fractions containing the desired product were combined and dried via centrifugal evaporation. The yield of 6-(cyclopropanecarboxamido)-4-((3-methoxy-4-(1-methyl-1H-1,2,4-triazol-3-yl)pyridin-2-yl)amino)-N-(methyl-d3)pyridazine-3-carboxamide was 8.6 mg, and its estimated purity by LCMS analysis was 99%. LCMS m/z 427.5 (M+H)⁺; HPLC t$_R$ 0.89 min (analytical HPLC Method A); ¹H NMR (500 MHz, DMSO-d₆) δ 12.43 (s, 1H), 11.46-11.25 (m, 1H), 9.88 (s, 1H), 9.24 (br s, 1H), 8.75-8.60 (m, 1H), 8.14 (d, J=5.1 Hz, 1H), 7.50 (d, J=5.2 Hz, 1H), 3.99 (s, 3H), 3.94-3.81 (m, 3H), 2.18-2.04 (m, 1H), 0.96-0.80 (m, 4H).

The Examples in Table 1 were prepared using a similar procedure used to prepare Example 1.

TABLE 1

| Ex. No. | Structure | Mol Wt | LCMS m/z observed | HPLC t$_R$ (min) | HPLC method |
|---|---|---|---|---|---|
| 2 | 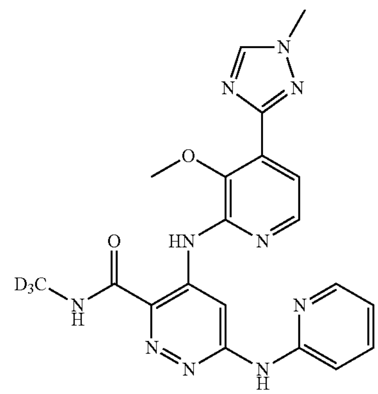 [SMILES: [2H]C([2H])([2H])NC(=O)c1nnc(Nc2ccccn2)cc1Nc1nccc(-c2ncn(C)n2)c1OC] | 435 | 436.1 | 0.62 | B |
| 3 | 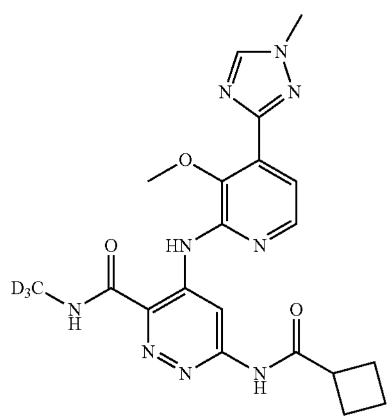 [SMILES: [2H]C([2H])([2H])NC(=O)c1nnc(NC(=O)C2CCC2)cc1Nc1nccc(-c2ncn(C)n2)c1OC] | 440 | 441.1 | 0.95 | A |
| 4 | 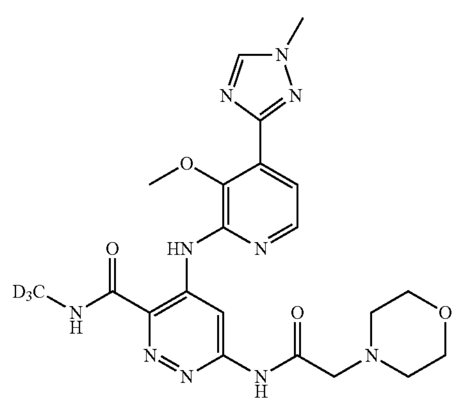 [SMILES: [2H]C([2H])([2H])NC(=O)c1nnc(NC(=O)CN2CCOCC2)cc1Nc1nccc(-c2ncn(C)n2)c1OC] | 485 | 486.4 | 0.89 | A |

TABLE 1-continued

| Ex. No. | Structure | Mol Wt | LCMS m/z observed | HPLC $t_R$ (min) | HPLC method |
|---|---|---|---|---|---|
| 5 | 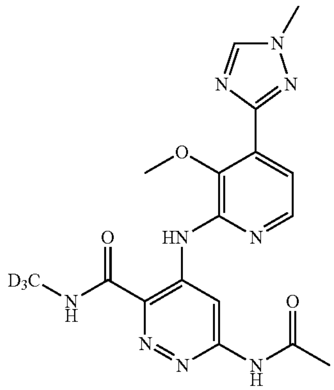 [SMILES: [2H]C([2H])([2H])NC(=O)c1nnc(NC(C)=O)cc1Nc1nccc(-c2ncn(C)n2)c1OC] | 400 | 401.3 | 0.89 | A |
| 6 | 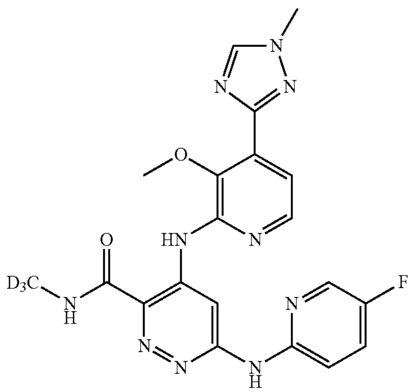 [SMILES: [2H]C([2H])([2H])NC(=O)c1nnc(Nc2ccc(F)cn2)cc1Nc1nccc(-c2ncn(C)n2)c1OC] | 453 | 454.3 | 0.91 | A |
| 7 | 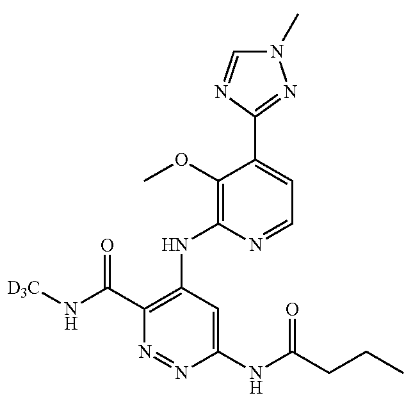 [SMILES: [2H]C([2H])([2H])NC(=O)c1nnc(NC(=O)CCC)cc1Nc1nccc(-c2ncn(C)n2)c1OC] | 428 | 429.5 | 1.04 | A |
| 8 | 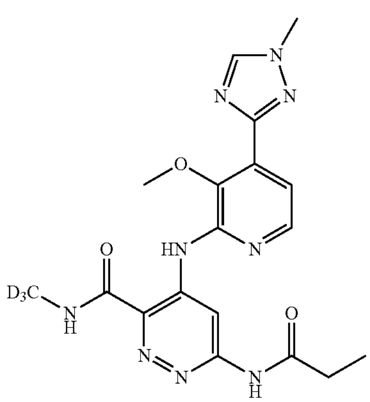 [SMILES: [2H]C([2H])([2H])NC(=O)c1nnc(NC(=O)CC)cc1Nc1nccc(-c2ncn(C)n2)c1OC] | 414 | 415.5 | 0.88 | A |

TABLE 1-continued

| Ex. No. | Structure | Mol Wt | LCMS m/z observed | HPLC t$_R$ (min) | HPLC method |
|---|---|---|---|---|---|
| 9 | 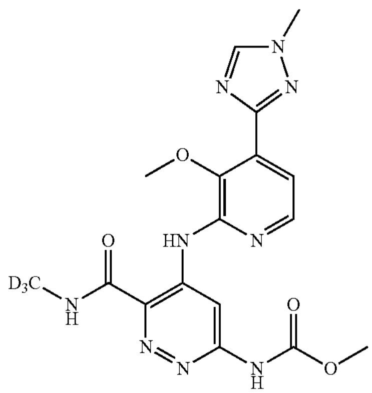 [SMILES: [2H]C([2H])([2H])NC(=O)c1nnc(NC(=O)OC)cc1Nc1nccc(-c2ncn(C)n2)c1OC] | 416 | 417.2 | 1.09 | C |
| 10 | 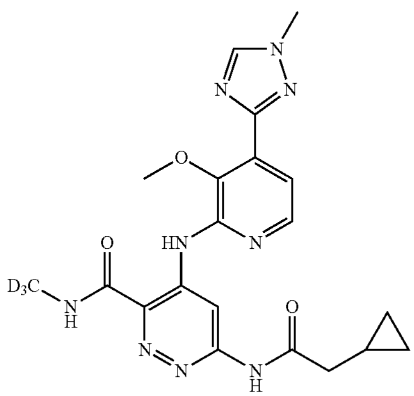 [SMILES: [2H]C([2H])([2H])NC(=O)c1nnc(NC(=O)CC2CC2)cc1Nc1nccc(-c2ncn(C)n2)c1OC] | 440 | 441.4 | 0.94 | A |
| 11 | 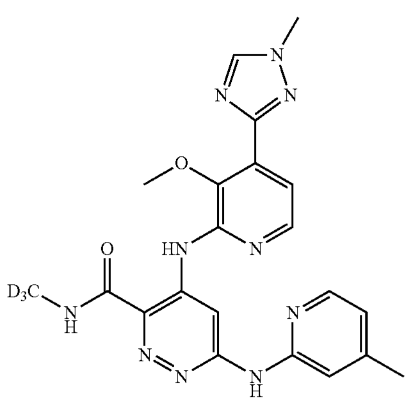 [SMILES: [2H]C([2H])([2H])NC(=O)c1nnc(Nc2cc(C)ccn2)cc1Nc1nccc(-c2ncn(C)n2)c1OC] | 449 | 450.4 | 0.92 | A |

TABLE 1-continued

| Ex. No. | Structure | Mol Wt | LCMS m/z observed | HPLC $t_R$ (min) | HPLC method |
|---|---|---|---|---|---|
| 12 | 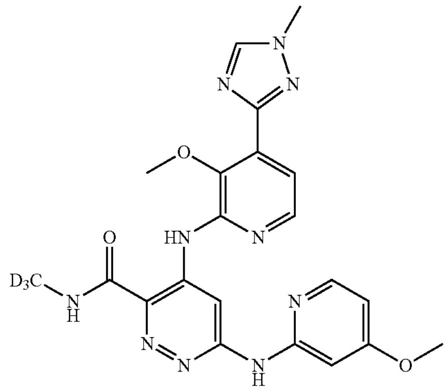 [SMILES: [2H]C([2H])([2H])NC(=O)c1nnc(Nc2cc(OC)ccn2)cc1Nc1nccc(-c2ncn(C)n2)c1OC] | 465 | 466.4 | 0.91 | A |
| 13 | 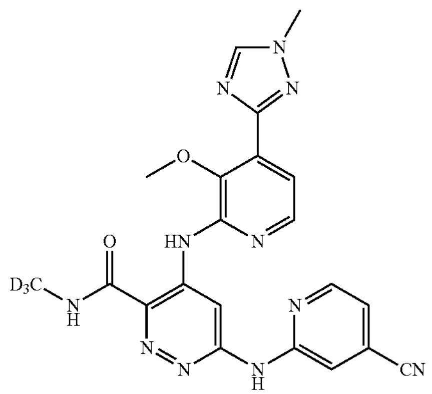 [SMILES: [2H]C([2H])([2H])NC(=O)c1nnc(Nc2cc(C#N)ccn2)cc1Nc1nccc(-c2ncn(C)n2)c1OC] | 460 | 461.4 | 0.93 | A |
| 15 | 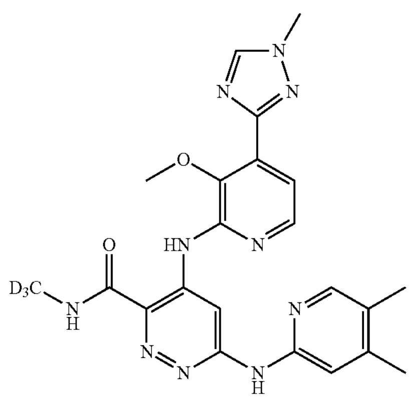 [SMILES: [2H]C([2H])([2H])NC(=O)c1nnc(Nc2cc(C)c(C)cn2)cc1Nc1nccc(-c2ncn(C)n2)c1OC] | 463 | 464.5 | 0.94 | A |
| 16 | 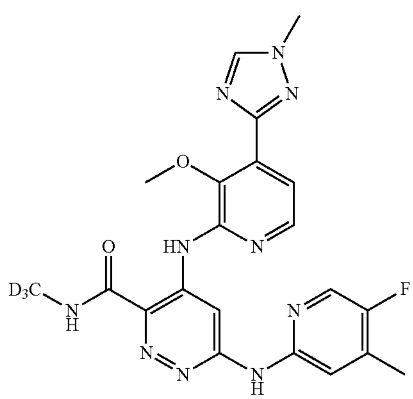 [SMILES: [2H]C([2H])([2H])NC(=O)c1nnc(Nc2cc(C)c(F)cn2)cc1Nc1nccc(-c2ncn(C)n2)c1OC] | 467 | 468.5 | 0.93 | A |

TABLE 1-continued

| Ex. No. | Structure | Mol Wt | LCMS m/z observed | HPLC t_R (min) | HPLC method |
|---|---|---|---|---|---|
| 17 | 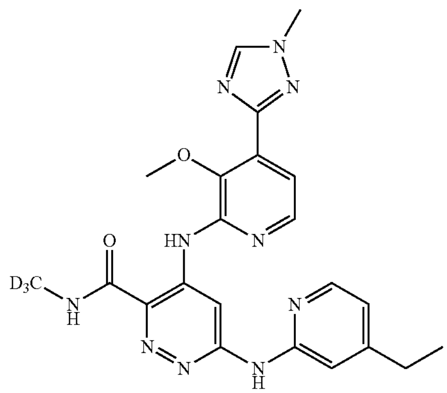 [SMILES: [2H]C([2H])([2H])NC(=O)c1nnc(Nc2cc(CC)ccn2)cc1Nc1nccc(-c2ncn(C)n2)c1OC] | 463 | 464.5 | 0.98 | A |
| 18 | 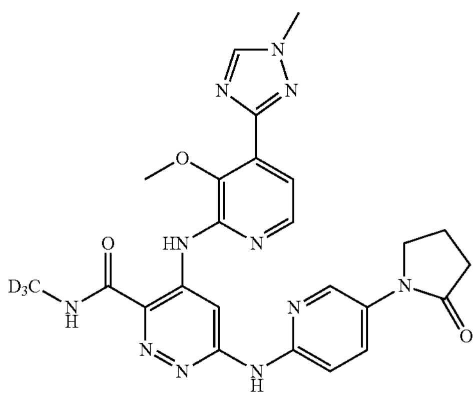 [SMILES: [2H]C([2H])([2H])NC(=O)c1nnc(Nc2ccc(N3CCCC3=O)cn2)cc1Nc1nccc(-c2ncn(C)n2)c1OC] | 518 | 519.4 | 0.94 | A |
| 19 | 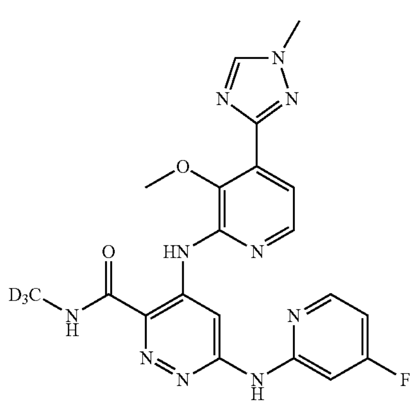 [SMILES: [2H]C([2H])([2H])NC(=O)c1nnc(Nc2cc(F)ccn2)cc1Nc1nccc(-c2ncn(C)n2)c1OC] | 453 | 454.3 | 0.96 | A |

TABLE 1-continued

| Ex. No. | Structure | Mol Wt | LCMS m/z observed | HPLC $t_R$ (min) | HPLC method |
|---|---|---|---|---|---|
| 20 | 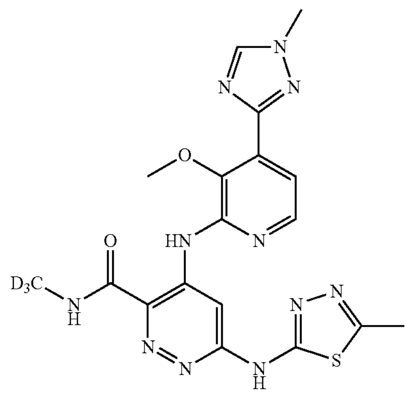 [SMILES: [2H]C([2H])([2H])NC(=O)c1nnc(Nc2nnc(C)s2)cc1Nc1nccc(-c2ncn(C)n2)c1OC] | 456 | 457.3 | 0.95 | A |
| 21 | 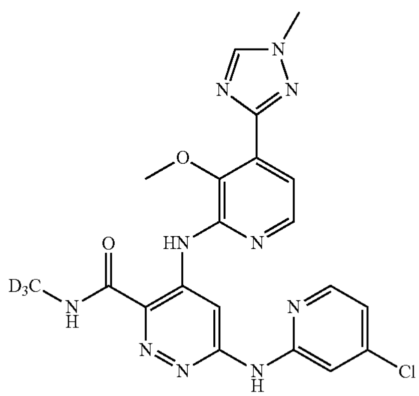 [SMILES: [2H]C([2H])([2H])NC(=O)c1nnc(Nc2cc(Cl)ccn2)cc1Nc1nccc(-c2ncn(C)n2)c1OC] | 469 | 470.4 | 0.97 | A |
| 22 | 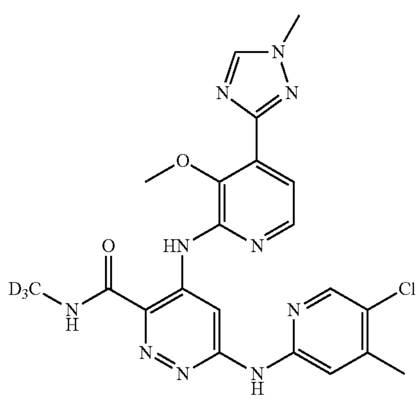 [SMILES: [2H]C([2H])([2H])NC(=O)c1nnc(Nc2cc(C)c(Cl)cn2)cc1Nc1nccc(-c2ncn(C)n2)c1OC] | 483 | 484.5 | 1.01 | A |
| 23 | 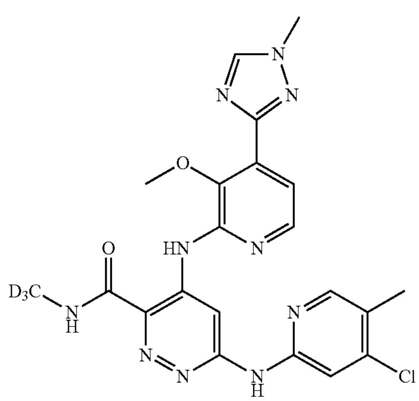 [SMILES: [2H]C([2H])([2H])NC(=O)c1nnc(Nc2cc(Cl)c(C)cn2)cc1Nc1nccc(-c2ncn(C)n2)c1OC] | 483 | 484.5 | 1.02 | A |

TABLE 1-continued

| Ex. No. | Structure | Mol Wt | LCMS m/z observed | HPLC $t_R$ (min) | HPLC method |
|---|---|---|---|---|---|
| 24 | 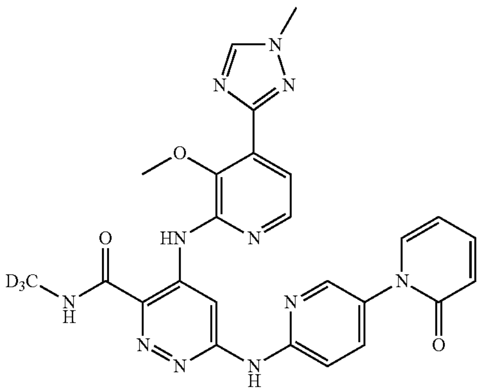 [SMILES: [2H]C([2H])([2H])NC(=O)c1nnc(Nc2ccc(-n3ccccc3=O)cn2)cc1Nc1nccc(-c2ncn(C)n2)c1OC] | 528 | 529.6 | 0.95 | A |
| 25 | 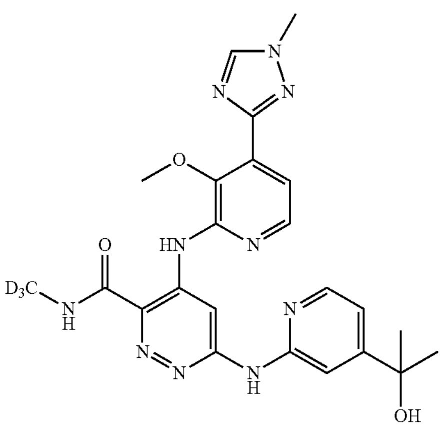 [SMILES: [2H]C([2H])([2H])NC(=O)c1nnc(Nc2cc(C(C)(C)O)ccn2)cc1Nc1nccc(-c2ncn(C)n2)c1OC] | 493 | 494.5 | 0.96 | A |
| 26 | 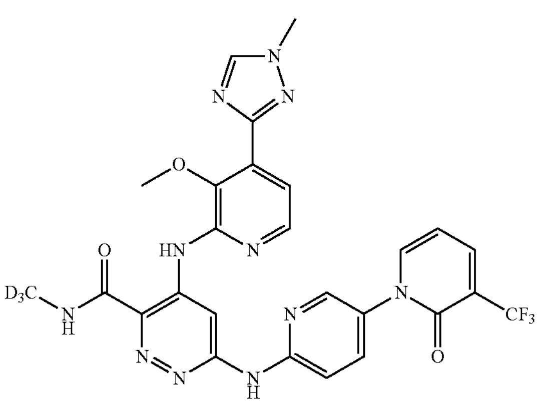 [SMILES: [2H]C([2H])([2H])NC(=O)c1nnc(Nc2ccc(-n3cccc(C(F)(F)F)c3=O)cn2)cc1Nc1nccc(-c2ncn(C)n2)c1OC] | 596 | 597.6 | 0.94 | A |

TABLE 1-continued

| Ex. No. | Structure | Mol Wt | LCMS m/z observed | HPLC $t_R$ (min) | HPLC method |
|---|---|---|---|---|---|
| 27 | 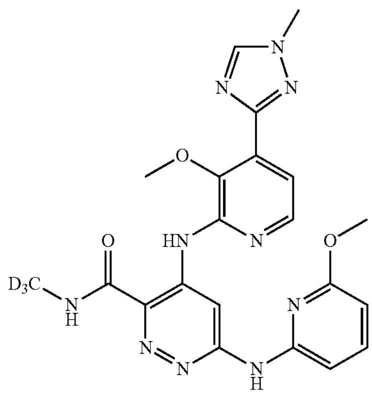 [SMILES: [2H]C([2H])([2H])NC(=O)c1nnc(Nc2cccc(OC)n2)cc1Nc1nccc(-c2ncn(C)n2)c1OC] | 465 | 466.4 | 1.07 | A |
| 28 | 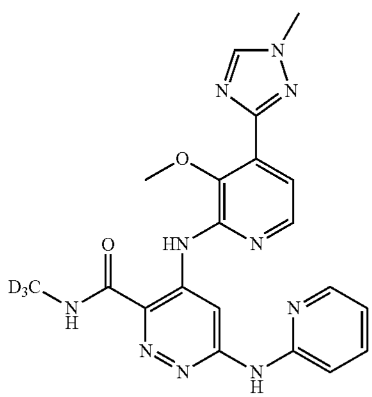 [SMILES: [2H]C([2H])([2H])NC(=O)c1nnc(Nc2ccccn2)cc1Nc1nccc(-c2ncn(C)n2)c1OC] | 435 | 436.4 | 0.99 | A |
| 29 | 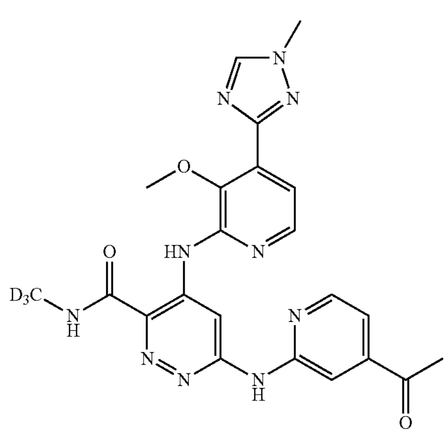 [SMILES: [2H]C([2H])([2H])NC(=O)c1nnc(Nc2cc(C(C)=O)ccn2)cc1Nc1nccc(-c2ncn(C)n2)c1OC] | 477 | 478.5 | 0.95 | A |

TABLE 1-continued

| Ex. No. | Structure | Mol Wt | LCMS m/z observed | HPLC $t_R$ (min) | HPLC method |
|---|---|---|---|---|---|
| 30 | 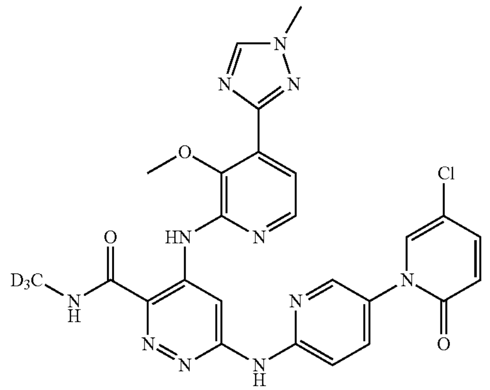 [SMILES: [2H]C([2H])([2H])NC(=O)c1nnc(Nc2ccc(-n3cc(Cl)ccc3=O)cn2)cc1Nc1nccc(-c2ncn(C)n2)c1OC] | 562 | 563.5 | 0.93 | A |
| 31 | 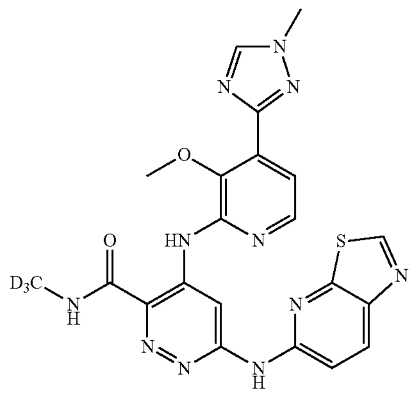 [SMILES: [2H]C([2H])([2H])NC(=O)c1nnc(Nc2ccc3ncsc3n2)cc1Nc1nccc(-c2ncn(C)n2)c1OC] | 492 | 493.3 | 0.89 | A |
| 32 | 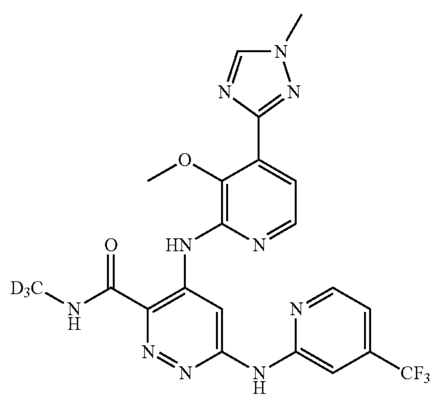 [SMILES: [2H]C([2H])([2H])NC(=O)c1nnc(Nc2cc(C(F)(F)F)ccn2)cc1Nc1nccc(-c2ncn(C)n2)c1OC] | 503 | 504.1 | 0.74 | B |
| 33 | 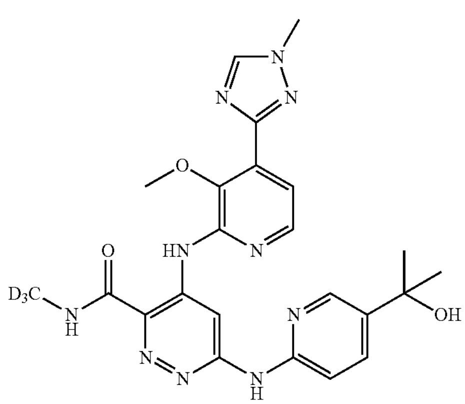 [SMILES: [2H]C([2H])([2H])NC(=O)c1nnc(Nc2ccc(C(C)(C)O)cn2)cc1Nc1nccc(-c2ncn(C)n2)c1OC] | 493 | 494.5 | 0.91 | A |

TABLE 1-continued

| Ex. No. | Structure | Mol Wt | LCMS m/z observed | HPLC $t_R$ (min) | HPLC method |
|---|---|---|---|---|---|
| 34 | 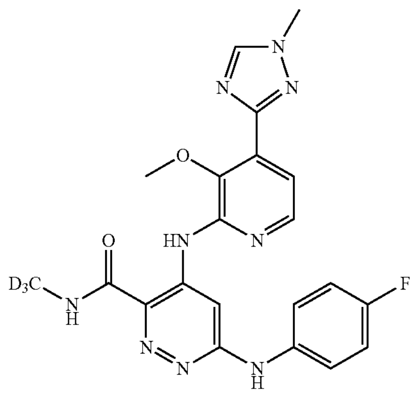 [SMILES: [2H]C([2H])([2H])NC(=O)c1nnc(Nc2ccc(F)cc2)cc1Nc1nccc(-c2ncn(C)n2)c1OC] | 452 | 453.4 | 1.05 | A |
| 35 | 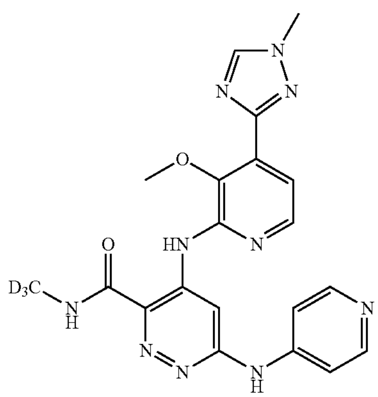 [SMILES: [2H]C([2H])([2H])NC(=O)c1nnc(Nc2ccncc2)cc1Nc1nccc(-c2ncn(C)n2)c1OC] | 435 | 436.4 | 0.88 | A |
| 36 | 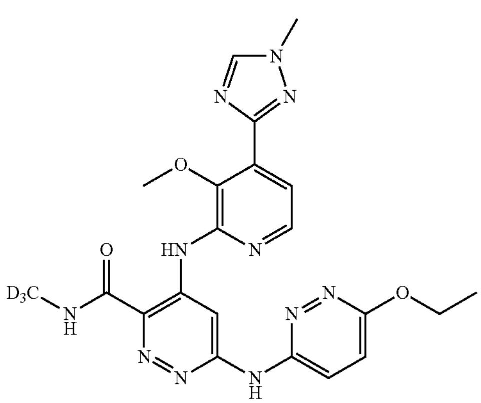 [SMILES: [2H]C([2H])([2H])NC(=O)c1nnc(Nc2ccc(OCC)nn2)cc1Nc1nccc(-c2ncn(C)n2)c1OC] | 480 | 481.5 | 0.93 | A |

TABLE 1-continued

| Ex. No. | Structure | Mol Wt | LCMS m/z observed | HPLC $t_R$ (min) | HPLC method |
|---|---|---|---|---|---|
| 37 | 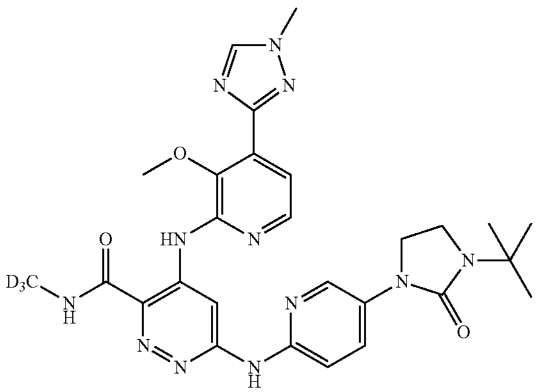 [SMILES: [2H]C([2H])([2H])NC(=O)c1nnc(Nc2ccc(N3CCN(C(C)(C)C)C3=O)cn2)cc1Nc1nccc(-c2ncn(C)n2)c1OC] | 575 | 576.5 | 1.01 | A |
| 38 | 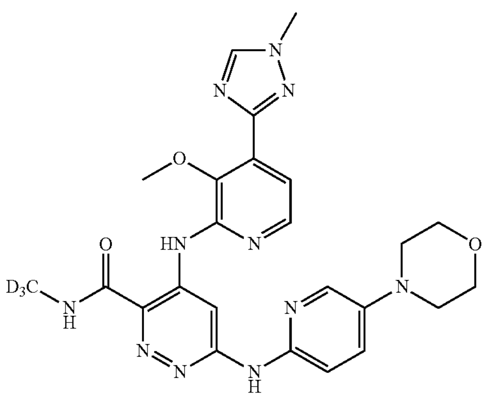 [SMILES: [2H]C([2H])([2H])NC(=O)c1nnc(Nc2ccc(N3CCOCC3)cn2)cc1Nc1nccc(-c2ncn(C)n2)c1OC] | 520 | 521.5 | 0.91 | A |
| 39 | 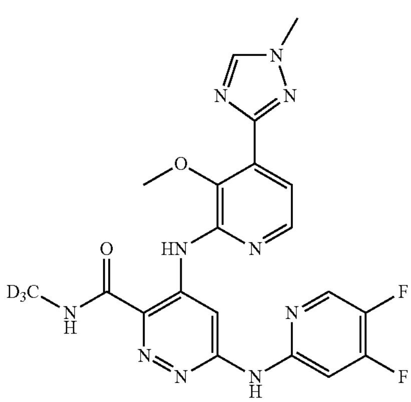 [SMILES: [2H]C([2H])([2H])NC(=O)c1nnc(Nc2cc(F)c(F)cn2)cc1Nc1nccc(-c2ncn(C)n2)c1OC] | 471 | 472.4 | 1.38 | A |

TABLE 1-continued

| Ex. No. | Structure | Mol Wt | LCMS m/z observed | HPLC $t_R$ (min) | HPLC method |
|---|---|---|---|---|---|
| 40 | 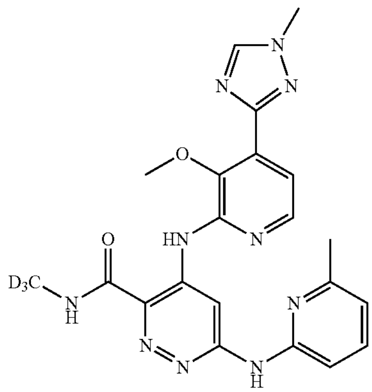 [SMILES: [2H]C([2H])([2H])NC(=O)c1nnc(Nc2cccc(C)n2)cc1Nc1nccc(-c2ncn(C)n2)c1OC] | 449 | 450.4 | 0.93 | A |

Example 41

6-(cyclopropncoamido)((3-methoxy-4-(methyl-1,24-oxadiazol-3-yl)pyridin-2-yl)amino)-N-(methyl-d3)nicotinamide

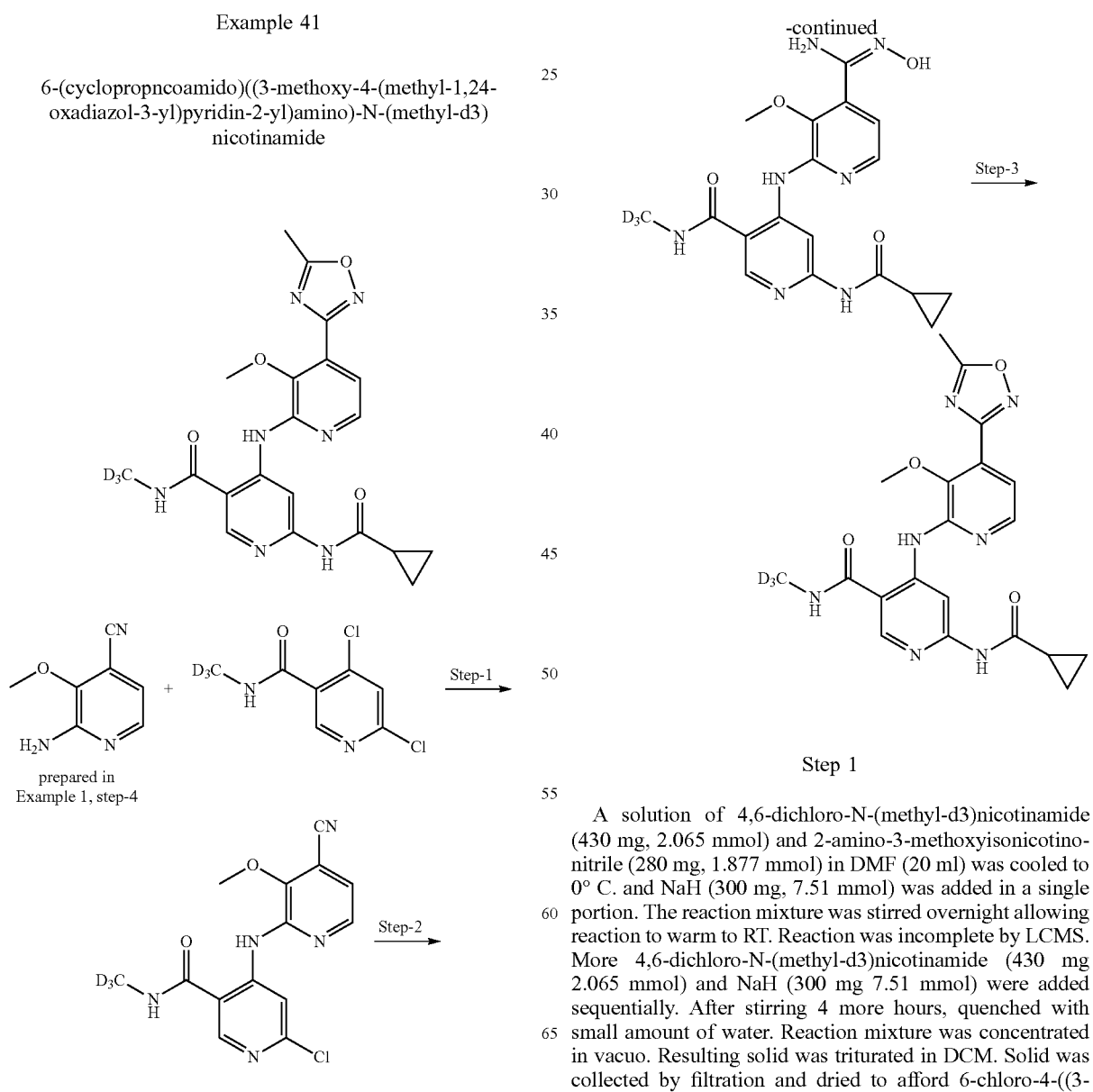

Step 1

A solution of 4,6-dichloro-N-(methyl-d3)nicotinamide (430 mg, 2.065 mmol) and 2-amino-3-methoxyisonicotinonitrile (280 mg, 1.877 mmol) in DMF (20 ml) was cooled to 0° C. and NaH (300 mg, 7.51 mmol) was added in a single portion. The reaction mixture was stirred overnight allowing reaction to warm to RT. Reaction was incomplete by LCMS. More 4,6-dichloro-N-(methyl-d3)nicotinamide (430 mg 2.065 mmol) and NaH (300 mg 7.51 mmol) were added sequentially. After stirring 4 more hours, quenched with small amount of water. Reaction mixture was concentrated in vacuo. Resulting solid was triturated in DCM. Solid was collected by filtration and dried to afford 6-chloro-4-((3- methoxy-4-(1-methyl-1H-1,2,4-triazol-3-yl)pyridin-2-yl)amino)-N-(methyl-d3)pyridazine-3-carboxamide (370 mg, 1.154 mmol, 61.4% yield). MS (m+1)=321.0. HPLC Peak RT=0.86 minutes. (Method I)

Step 2

A mixture of 6-chloro-4-((4-cyano-3-methoxypyridin-2-yl)amino)-N-(methyl-d3)nicotinamide (40 mg, 0.125 mmol), cyclopropanecarboxamide (21.23 mg, 0.249 mmol), Xantphos (14.43 mg, 0.025 mmol), Cs$_2$CO$_3$ (81 mg, 0.249 mmol) and Pd$_2$(dba)$_3$ (11.42 mg, 0.012 mmol) in dioxane (0.60 mL) was sparged with nitrogen for 2 min., then sealed and stirred at 130° C. for 1 h. The reaction mixture was diluted with ethyl acetate and washed with sat NaCl. The organic layer was dried with MgSO$_4$, filtered and concentrated. MS (m+1)=370.0. HPLC Peak RT=0.67 minutes. (method?). The crude residue was transferred to a vial and Ethanol (5 mL) was added followed by 1M NH$_2$OH in EtOH (0.624 mL, 0.624 mmol). The reaction mixture was heated at 85° C. in a sealed vial overnight. Cooled and filtered away any solids. Filtrate was concentrated and used in the next step without further purification. MS (m+1)=403.1. HPLC Peak RT=0.50 minutes. (Method I).

Step 3

To a mixture of (E)-6-(cyclopropanecarboxamido)-4-((4-(N'-hydroxycarbamimidoyl)-3-methoxypyridin-2-yl)amino)-N-(methyl-d3)nicotinamide (50 mg, 0.124 mmol) and acetic acid (0.014 mL, 0.248 mmol) in DMF (2 mL) was added DIC (0.039 mL, 0.248 mmol). After 1 hour, LCMS shows coupling is complete. TBAF in THF (0.373 mL, 0.373 mmol) was added. Heated at 80° C. overnight. The reaction mixture was diluted with dichloromethane and washed with H$_2$O and 1 mL of sat. NaHCO$_3$. Washed 4 more times with water to remove TBAF. The organic layer was dried with MgSO$_4$, filtered and concentrated. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 minutes, then a 5-minute hold at 100% B; Flow: 20 mL/min. Fractions containing the desired product were combined and dried via centrifugal evaporation to afford 6-(cyclopropanecarboxamido)-4-((3-methoxy-4-(5-methyl-1,2,4-oxadiazol-3-yl)pyridin-2-yl)amino)-N-(methyl-d3)nicotinamide (6.2 mg, 0.014 mmol, 11.23% yield). $^1$H NMR (500 MHz, DMSO-d6) δ 12.12 (s, 1H), 10.81 (s, 1H), 9.59 (s, 1H), 8.71 (s, 1H), 8.62 (s, 1H), 8.21 (d, J=5.1 Hz, 1H), 7.39 (d, J=5.1 Hz, 1H), 3.88 (s, 3H), 2.72 (s, 3H), 2.03 (d, J=4.6 Hz, 1H), 0.97-0.69 (m, 4H); MS (m+1)=427.3; HPLC Peak RT=1.14 minutes. (Method qc-acn-tfa-xb-02); HPLC Purity=96%

Example 42

4-((3-methoxy-4-(5-(morpholinomethyl)-1,2,4-oxadiazol-3-yl)pyridin-2-yl)amino)-N-trideuteromethyl-6-((4-methylpyridin-2-yl)amino)pyridazine-3-carboxamide

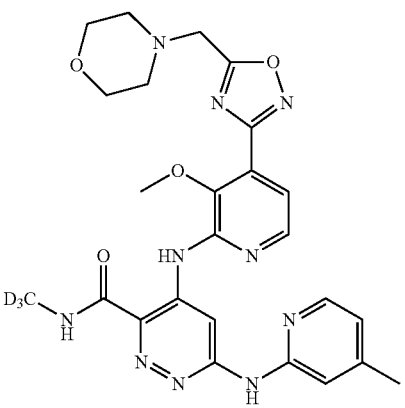 [SMILES: [2H]C([2H])([2H])NC(=O)c1nnc(Nc2cc(C)ccn2)cc1Nc1nccc(-c2noc(CN3CCOCC3)n2)c1OC]

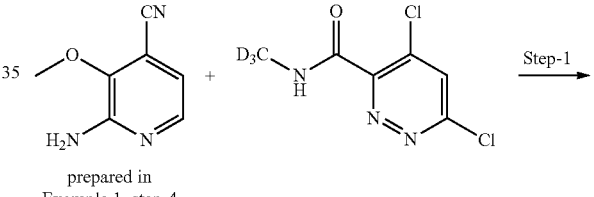

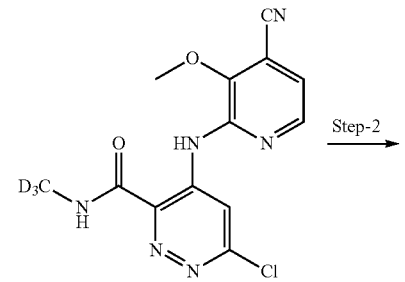

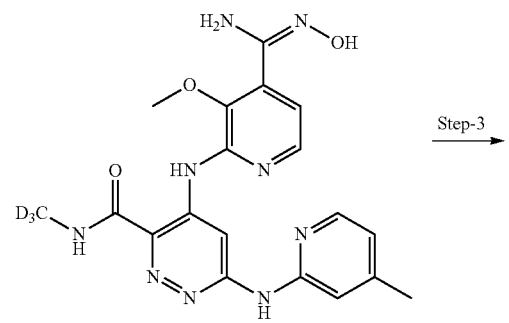

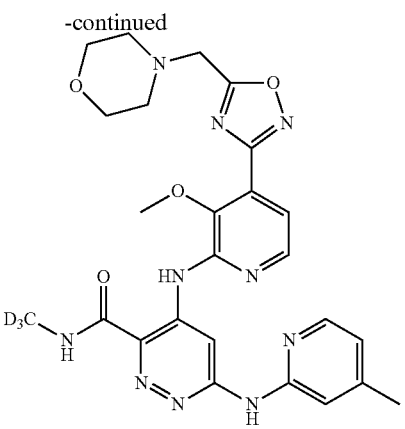

Step 1

A solution of 4,6-dichloro-N-trideuteromethylpyridazine-3-carboxamiide (0.420 g, 2.01 mmol) and 2-amino-3-methoxyisonicotinonitrile (0.300 g, 2.01 mmol) in DMF (13.4 mL) was cooled to 0° C. and NaH (0.257 g, 6.44 mmol) was added in a single portion. After 5 minutes, the reaction was allowed to warm to room temp. After 2.5 hours, more NaH (0.050 g, 1.25 mmol) was added. After stirring for 21.5 hours more, NaH (0.050 g 1.25 mmol) was added, and after 30 minutes, NaH (0.050 g, 1.25 mmol) was added again, at which point the reaction was deemed complete. Reaction was quenched with saturated aqueous ammonium chloride, water, and DCM, and solids precipitated. Saturated aqueous $KH_2PO_4$ was added to bring mixture to ~pH 5. The quenched reaction mixture was extracted with a 4/1 mixture of $CHCl_3$/iPrOH three times, and the combined organics were washed with water and concentrated without filtration because of suspended solids solids. After concentration of the organic layer, the obtained orange solid was taken up as a slurry in DCM and filtered through a medium frit. The solid was triturated with DCM and dried to obtain 6-chloro-4-((4-cyano-3-methoxypyridin-2-yl)amino)-N-trideuteromethylpyridazine-3-carboxamide (0.273 g, 0.849 mmol, 42% yield) as an off-white solid. LCMS RT=0.89 minutes (TS). MS (m+1)=322.0. This material was carried forward without additional purification.

Step 2

A mixture of 6-chloro-4-((4-cyano-3-methoxypyridin-2-yl)amino)-N-trideuteromethylpyridazine-3-carboxamide (0.100 g, 0.311 mmol), Xantphos (0.036 g, 0.062 mmol), $Pd_2(dba)_3$ (0.028 g, 0.031 mmol), 4-methylpyridin-2-amine (0.067 g, 0.622 mmol) and $Cs_2CO_3$ (0.253 g, 0.777 mmol) in dioxane (3.11 mL) was degassed by bubbling nitrogen gas through the mixture for 10 minutes. The reaction vessel was sealed and heated to 130° C. for 1 hour. The reaction was cooled to room temperature, diluted with EtOAc and filtered through a celite pad. The filtrate was washed with water twice, dried over sodium sulfate, filtered, and concentrated to afford a crude yellow solid. This crude yellow solid contained some desired material as well as leftover amine and catalyst. The rest of the product precipitated out and remained in the frit with the celite pad. The solid mixture from the frit was suspended in 20 mL of DMF which was then filtered. The DMF filtrate was diluted with EtOAc (120 mL) and washed with water. The organic layer was concentrated, suspended in $DCM/Et_2O$ and vacuumed dry in a frit. The collected solid was triturated with water and $Et_2O$ to provide 30 mg of brown solid. The crude yellow solid from the initial reaction filtration and workup was triturated with $Et_2O$ to give 98 mg of solid. Combined total of 128 mg of solid obtained, which was greater than quantitative recovery. The material was considered quantitative conversion to 4-((4-cyano-3-methoxypyridin-2-yl)amino)-N-trideuteromethyl-6-((4-methylpyridin-2-yl)amino)pyridazine-3-carboxamide (0.122 g, 0.311 mmol, 100% yield) LCMS RT=0.71 minutes (TS). MS (m+1)=394.1 and was carried forward without additional purification. A solution of hydroxylamine hydrochloride (0.216 g, 3.11 mmol) and KOH (0.174 g, 3.11 mmol) in ethanol (6.22 mL) was stirred for 1 hour at room temperature and then filtered. The filtrate was added to the material from above 4-((4-cyano-3-methoxypyridin-2-yl)amino)-N-trideuteromethyl-6-((4-methylpyridin-2-yl)amino)pyridazine-3-carboxamide (0.122 g, 0.311 mmol) and the resulting mixture was sealed and heated to 85° C. After 5 hours and 15 min, the reaction has finished. The reaction was cooled to room temperature, concentrated, and carried forward as is without purification. Consider quantitative yield of (Z)-4-((4-(N'-hydroxycarbamimidoyl)-3-methoxypyridin-2-yl)amino)-N-trideuteromethyl-6-((4-methylpyridin-2-yl)amino)pyridazine-3-carboxamide (0.133 g, 3.11 mmol, 100% yield). LCMS RT=0.55 minutes (TS). MS (m+1)=427.1.

Step 3

To a solution of (Z)-4-((4-(N'-hydroxycarbamimidoyl)-3-methoxypyridin-2-yl)amino)-N-trideuteromethyl-6-((4-methylpyridin-2-yl)amino)pyridazine-3-carboxamide (44.4 mg, 0.104 mmol) and 2-morpholinoacetic acid (45.3 mg, 0.312 mmol) in DMF (1 mL) was added DIC (0.065 mL, 0.416 mmol). After 30 minutes, TBAF (0.624 mL, 0.624 mmol) was added in a single portion. After 30 minutes, another aliquot of TBAF (0.624 mL, 0.624 mmol) was added. After 10 minutes more, the reaction was diluted with DCM, water, and ~1.5 mL of $NaHCO_3$ to keep the solution basic. The organic layer was washed with water five times, dried over sodium sulfate, filtered, and concentrated to afford a crude brown material. This material was taken up in DMF and purified by preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 20 minutes, then a 5-minute hold at 100% B; Flow: 20 mL/min. Fractions containing the desired product were combined and dried via centrifugal evaporation to give 4-((3-methoxy-4-(5-(morpholinomethyl)-1,2,4-oxadiazol-3-yl)pyridin-2-yl)amino)-N-trideuteromethyl-6-((4-methylpyridin-2-yl)amino)pyridazine-3-carboxamide, TFA (11.1 mg, 0.017 mmol, 16.19% yield), and its estimated purity by LCMS analysis was 98%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm. LCMS RT=1.73 minutes (QC-ACN-AA-XB). MS (m+1)=536.3. ¹H NMR (500 MHz, DMSO-d₆) δ 12.64 (s 1H), 9.32 (s, 1H), 9.22 (s, 1H), 8.33 (d, J=5.1 Hz, 1H), 8.29 (d, J=5.6 Hz, 1H), 7.94 (s, 1H), 7.55 (d, J=5.1 Hz, 1H), 7.37 (s, 1H), 7.07 (br d, J=5.4 Hz, 1H), 4.25 (s, 2H), 3.92 (s, 3H), 3.67 (br s, 4H), 2.79 (br s 4H) 2.41 (s 3H)

The Examples in Table 2 were prepared using a similar procedure used to prepare Example 41 and Example 42.

TABLE 2

| Ex. No. | Structure | Mol Wt | LCMS m/z observed | HPLC $t_R$ (min) | HPLC method |
|---|---|---|---|---|---|
| 43 | 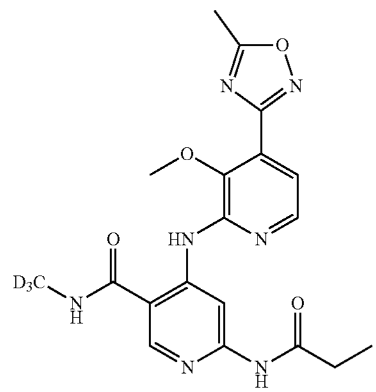 [SMILES: [2H]C([2H])([2H])NC(=O)c1cnc(NC(=O)CC)cc1Nc1nccc(-c2noc(C)n2)c1OC] | 414.4 | 415.3 | 1.09 | D |
| 44 | 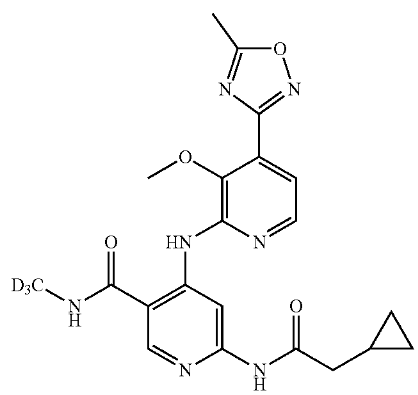 [SMILES: [2H]C([2H])([2H])NC(=O)c1cnc(NC(=O)CC2CC2)cc1Nc1nccc(-c2noc(C)n2)c1OC] | 440.5 | 441.2 | 1.48 | D |
| 45 | 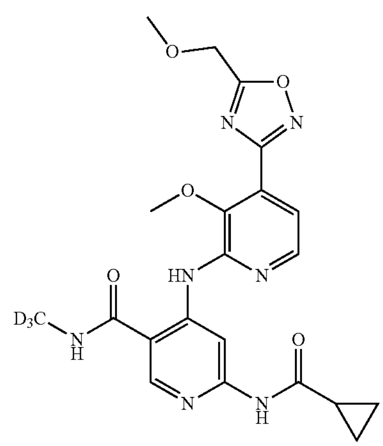 [SMILES: [2H]C([2H])([2H])NC(=O)c1cnc(NC(=O)C2CC2)cc1Nc1nccc(-c2noc(COC)n2)c1OC] | 456.5 | 457.2 | 1.17 | D |

TABLE 2-continued
| Ex. No. | Structure | Mol Wt | LCMS m/z observed | HPLC $t_R$ (min) | HPLC method |
|---|---|---|---|---|---|
| 46 | 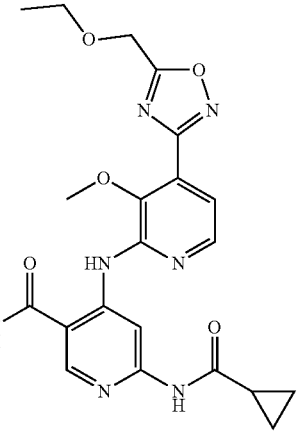 | 470.5 | 471.0 | 1.54 | D |
| 47 | 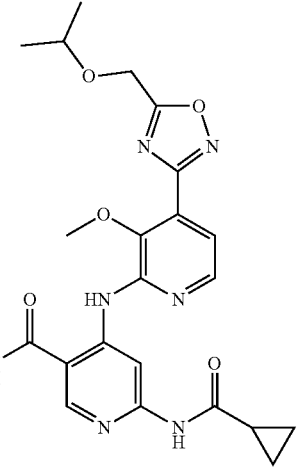 | 484.5 | 485.0 | 1.67 | D |
| 48 | 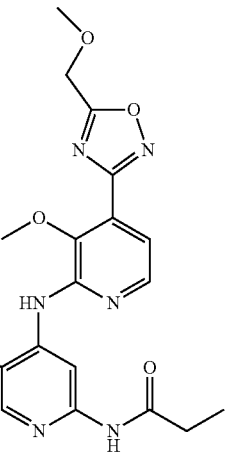 | 444.5 | 445.0 | 1.14 | D |

TABLE 2-continued

| Ex. No. | Structure | Mol Wt | LCMS m/z observed | HPLC t$_R$ (min) | HPLC method |
|---|---|---|---|---|---|
| 49 | 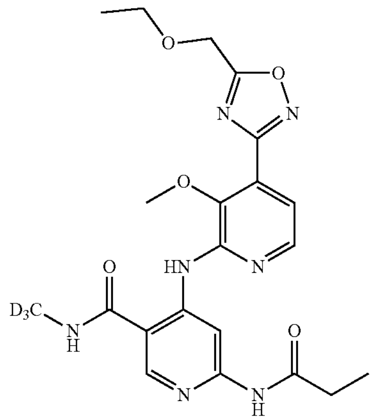 [SMILES: [2H]C([2H])([2H])NC(=O)c1cnc(NC(=O)CC)cc1Nc1nccc(-c2noc(COCC)n2)c1OC] | 458.5 | 459.2 | 1.25 | D |
| 50 | 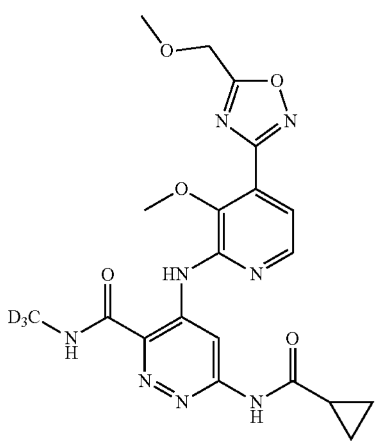 [SMILES: [2H]C([2H])([2H])NC(=O)c1nnc(NC(=O)C2CC2)cc1Nc1nccc(-c2noc(COC)n2)c1OC] | 457.5 | 458.2 | 1.47 | D |
| 51 | 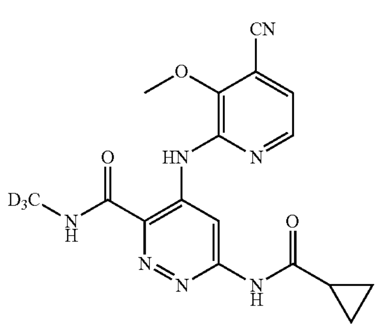 [SMILES: [2H]C([2H])([2H])NC(=O)c1nnc(NC(=O)C2CC2)cc1Nc1nccc(C#N)c1OC] | 370.4 | 371.2 | 1.31 | D |

TABLE 2-continued
| Ex. No. | Structure | Mol Wt | LCMS m/z observed | HPLC $t_R$ (min) | HPLC method |
|---|---|---|---|---|---|
| 52 | 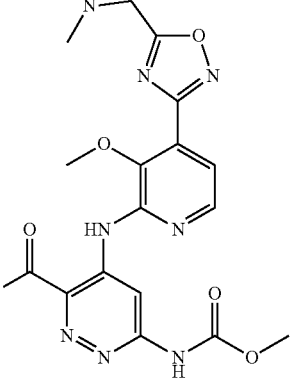 | 524.5 | 525.1 | 1.32 | D |
| 53 | 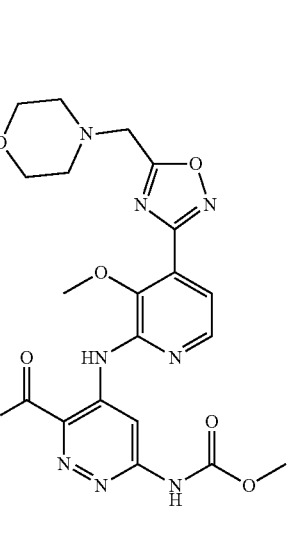 | 502.5 | 503.0 | 0.93 | D |
| 54 | 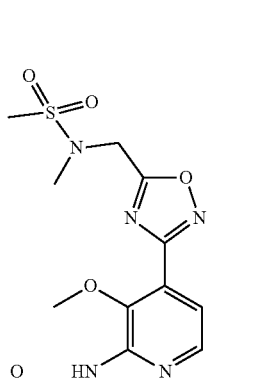 | 534.6 | 535.2 | 1.46 | D |

TABLE 2-continued

| Ex. No. | Structure | Mol Wt | LCMS m/z observed | HPLC $t_R$ (min) | HPLC method |
|---|---|---|---|---|---|
| 55 | 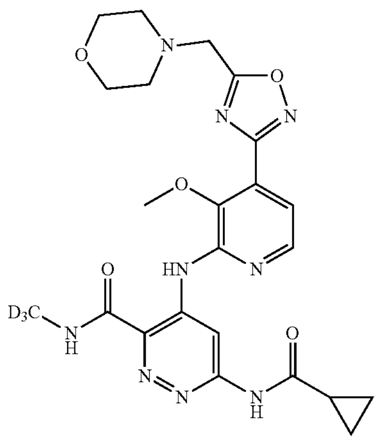 [SMILES: [2H]C([2H])([2H])NC(=O)c1nnc(NC(=O)C2CC2)cc1Nc1nccc(-c2noc(CN3CCOCC3)n2)c1OC] | 512.5 | 513.3 | 1.45 | D |
| 56 | 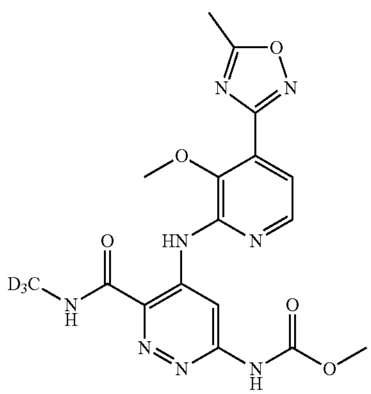 [SMILES: [2H]C([2H])([2H])NC(=O)c1nnc(NC(=O)OC)cc1Nc1nccc(-c2noc(C)n2)c1OC] | 417.4 | 418.0 | 1.38 | D |
| 57 | 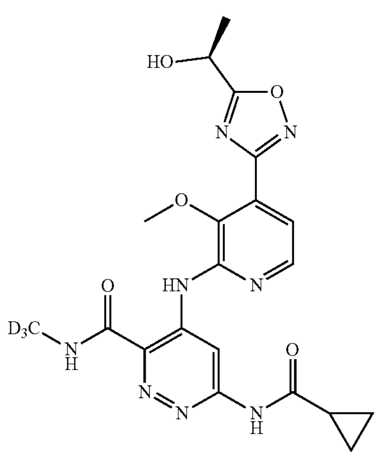 [SMILES: [2H]C([2H])([2H])NC(=O)c1nnc(NC(=O)C2CC2)cc1Nc1nccc(-c2noc([C@H](C)O)n2)c1OC] | 457.5 | 458.2 | 1.37 | D |

TABLE 2-continued
| Ex. No. | Structure | Mol Wt | LCMS m/z observed | HPLC $t_R$ (min) | HPLC method |
|---|---|---|---|---|---|
| 58 | 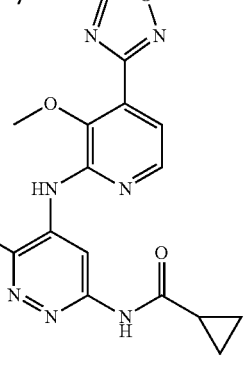 | 470.5 | 471.0 | 0.9 | D |
| 59 | 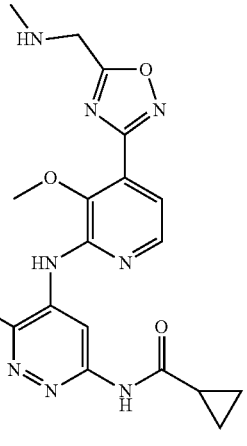 | 456.5 | 457.1 | 1.25 | D |
| 60 | 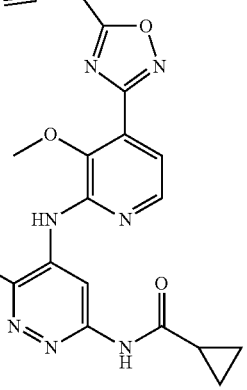 | 452.4 | 453.0 | 1.39 | D |

TABLE 2-continued

| Ex. No. | Structure | Mol Wt | LCMS m/z observed | HPLC $t_R$ (min) | HPLC method |
|---|---|---|---|---|---|
| 61 | 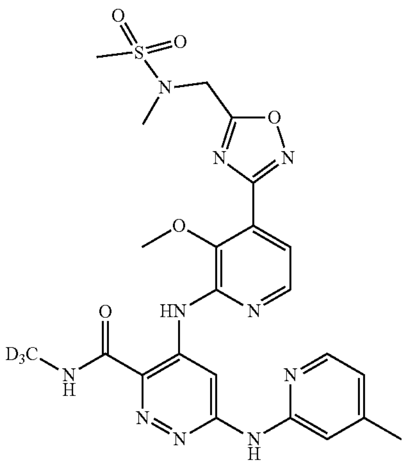 [SMILES: [2H]C([2H])([2H])NC(=O)c1nnc(Nc2cc(C)ccn2)cc1Nc1nccc(-c2noc(CN(C)S(C)(=O)=O)n2)c1OC] | 557.6 | 558.3 | 1.26 | D |
| 62 | 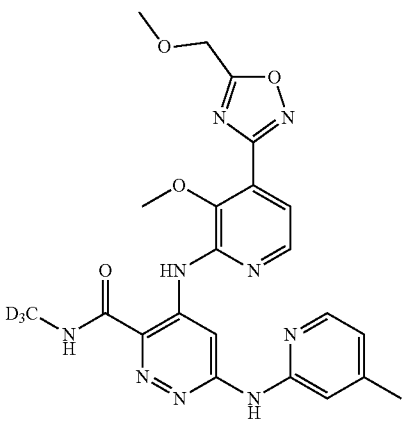 [SMILES: [2H]C([2H])([2H])NC(=O)c1nnc(Nc2cc(C)ccn2)cc1Nc1nccc(-c2noc(COC)n2)c1OC] | 480.5 | 481.3 | 1.81 | D |
| 63 | 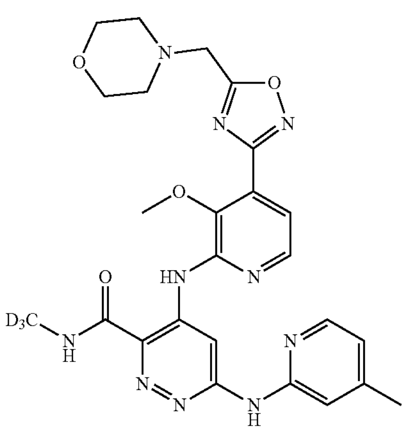 [SMILES: [2H]C([2H])([2H])NC(=O)c1nnc(Nc2cc(C)ccn2)cc1Nc1nccc(-c2noc(CN3CCOCC3)n2)c1OC] | 535.6 | 536.3 | 1.01 | D |

TABLE 2-continued
| Ex. No. | Structure | Mol Wt | LCMS m/z observed | HPLC $t_R$ (min) | HPLC method |
|---|---|---|---|---|---|
| 64 | 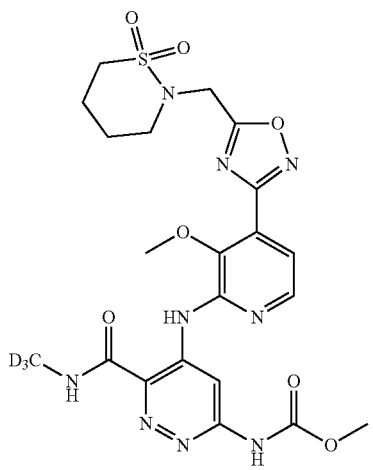 [SMILES: [2H]C([2H])([2H])NC(=O)c1nnc(NC(=O)OC)cc1Nc1nccc(-c2noc(CN3CCCCS3(=O)=O)n2)c1OC] | 550.6 | 551.1 | 1.4 | D |
| 65 | 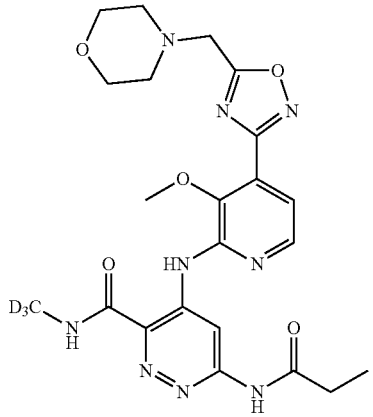 [SMILES: [2H]C([2H])([2H])NC(=O)c1nnc(NC(=O)CC)cc1Nc1nccc(-c2noc(CN3CCOCC3)n2)c1OC] | 500.5 | 501.0 | 1.36 | D |
| 66 | 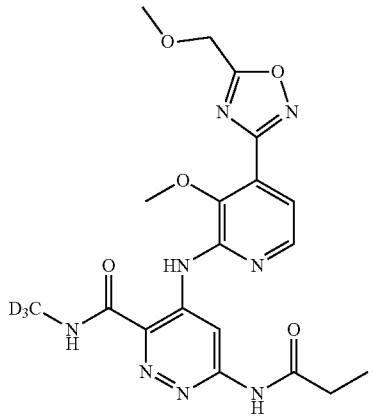 [SMILES: [2H]C([2H])([2H])NC(=O)c1nnc(NC(=O)CC)cc1Nc1nccc(-c2noc(COC)n2)c1OC] | 445.5 | 446.2 | 1.47 | D |

TABLE 2-continued
| Ex. No. | Structure | Mol Wt | LCMS m/z observed | HPLC $t_R$ (min) | HPLC method |
|---|---|---|---|---|---|
| 67 | 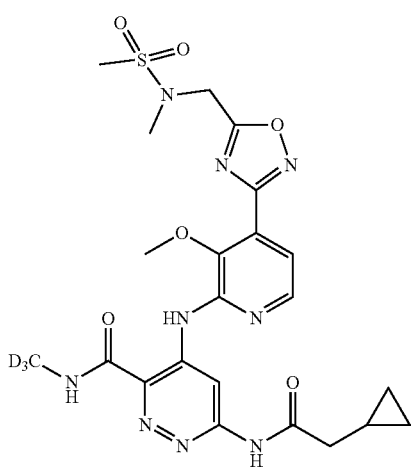 [SMILES: [2H]C([2H])([2H])NC(=O)c1nnc(NC(=O)CC2CC2)cc1Nc1nccc(-c2noc(CN(C)S(C)(=O)=O)n2)c1OC] | 548.6 | 549.3 | 1.56 | D |
| 68 | 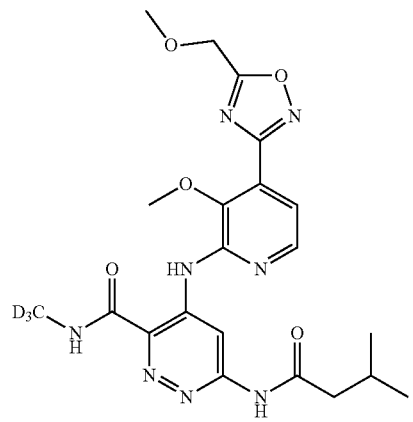 [SMILES: [2H]C([2H])([2H])NC(=O)c1nnc(NC(=O)CC(C)C)cc1Nc1nccc(-c2noc(COC)n2)c1OC] | 473.5 | 474.0 | 1.5 | D |
| 69 | 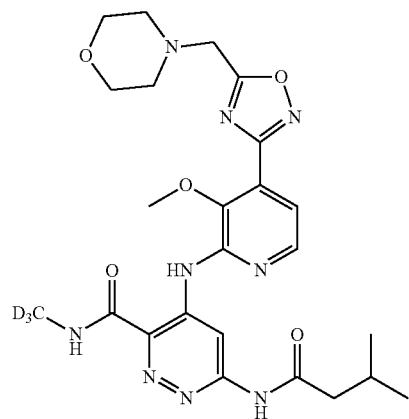 [SMILES: [2H]C([2H])([2H])NC(=O)c1nnc(NC(=O)CC(C)C)cc1Nc1nccc(-c2noc(CN3CCOCC3)n2)c1OC] | 528.6 | 529.3 | 1.15 | D |

TABLE 2-continued
| Ex. No. | Structure | Mol Wt | LCMS m/z observed | HPLC $t_R$ (min) | HPLC method |
|---|---|---|---|---|---|
| 70 | 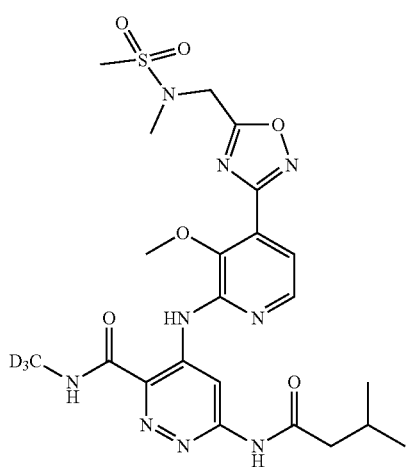 [SMILES: [2H]C([2H])([2H])NC(=O)c1nnc(NC(=O)CC(C)C)cc1Nc1nccc(-c2noc(CN(C)S(C)(=O)=O)n2)c1OC] | 550.6 | 551.3 | 1.66 | D |
| 71 | 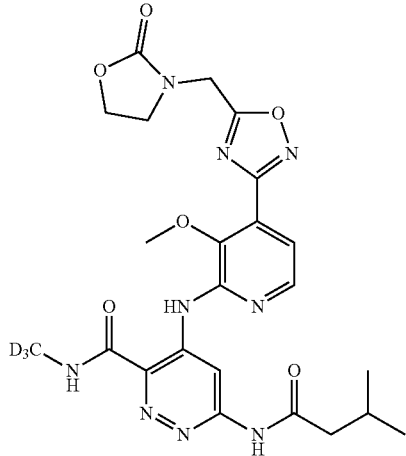 [SMILES: [2H]C([2H])([2H])NC(=O)c1nnc(NC(=O)CC(C)C)cc1Nc1nccc(-c2noc(CN3CCOC3=O)n2)c1OC] | 528.5 | 529.3 | 1.36 | D |
| 72 | 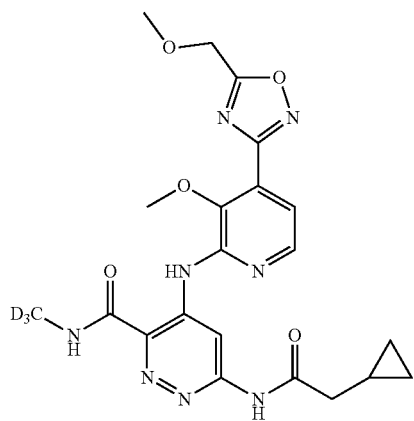 [SMILES: [2H]C([2H])([2H])NC(=O)c1nnc(NC(=O)CC2CC2)cc1Nc1nccc(-c2noc(COC)n2)c1OC] | 471.5 | 472.0 | 1.42 | D |

TABLE 2-continued

| Ex. No. | Structure | Mol Wt | LCMS m/z observed | HPLC $t_R$ (min) | HPLC method |
|---|---|---|---|---|---|
| 73 | 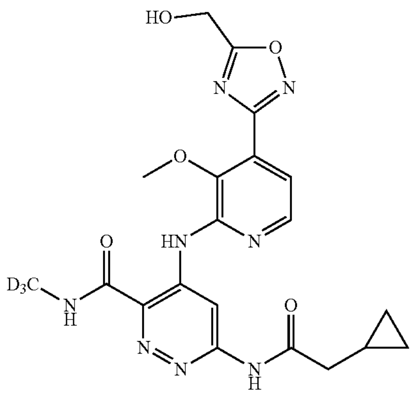 [SMILES: [2H]C([2H])([2H])NC(=O)c1nnc(NC(=O)CC2CC2)cc1Nc1nccc(-c2noc(CO)n2)c1OC] | 457.5 | 458.2 | 1.15 | D |
| 74 | 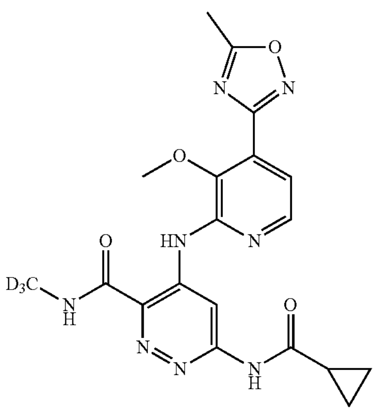 [SMILES: [2H]C([2H])([2H])NC(=O)c1nnc(NC(=O)C2CC2)cc1Nc1nccc(-c2noc(C)n2)c1OC] | 427.4 | 428.3 | 1.27 | D |
| 75 | 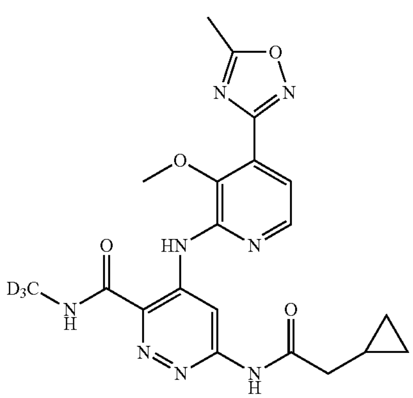 | 441.5 | 442.2 | 1.38 | D |

TABLE 2-continued

| Ex. No. | Structure | Mol Wt | LCMS m/z observed | HPLC $t_R$ (min) | HPLC method |
|---|---|---|---|---|---|
| 76 | 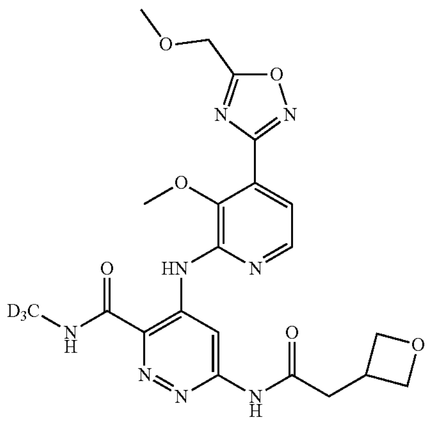 [SMILES: [2H]C([2H])([2H])NC(=O)c1nnc(NC(=O)CC2COC2)cc1Nc1nccc(-c2noc(COC)n2)c1OC] | 487.5 | 488.3 | 1.17 | D |
| 77 | 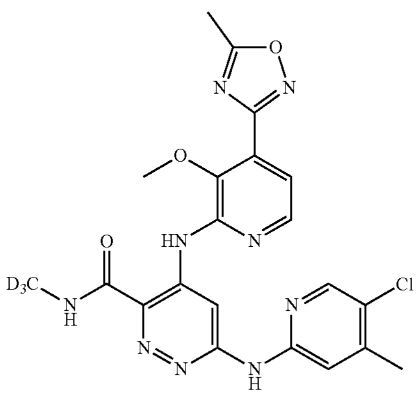 [SMILES: [2H]C([2H])([2H])NC(=O)c1nnc(Nc2cc(C)c(Cl)cn2)cc1Nc1nccc(-c2noc(C)n2)c1OC] | 484.9 | 484.9 | 2.02 | D |
| 78 | 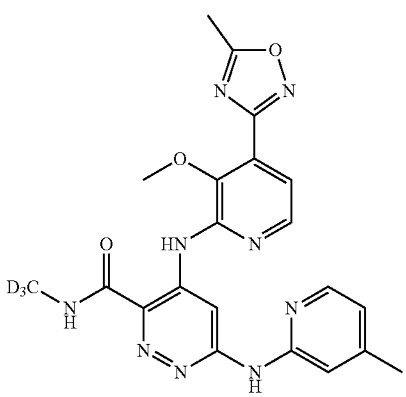 [SMILES: [2H]C([2H])([2H])NC(=O)c1nnc(Nc2cc(C)ccn2)cc1Nc1nccc(-c2noc(C)n2)c1OC] | 450.5 | 451.3 | 1.28 | D |
| 79 | 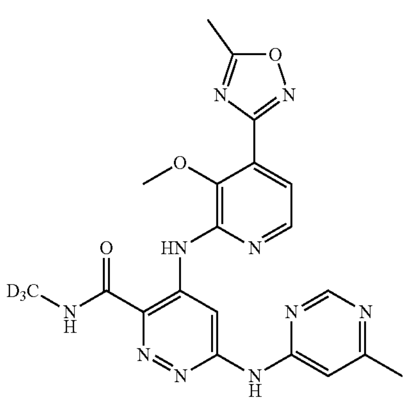 [SMILES: [2H]C([2H])([2H])NC(=O)c1nnc(Nc2cc(C)ncn2)cc1Nc1nccc(-c2noc(C)n2)c1OC] | 451.5 | 452.0 | 1.1 | D |

TABLE 2-continued

| Ex. No. | Structure | Mol Wt | LCMS m/z observed | HPLC $t_R$ (min) | HPLC method |
|---|---|---|---|---|---|
| 80 | 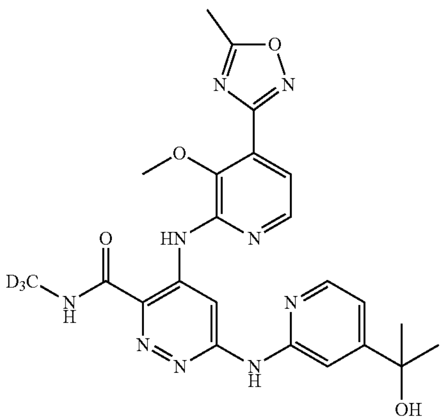 [SMILES: [2H]C([2H])([2H])NC(=O)c1nnc(Nc2cc(C(C)(C)O)ccn2)cc1Nc1nccc(-c2noc(C)n2)c1OC] | 494.5 | 495.2 | 1.26 | D |
| 81 | 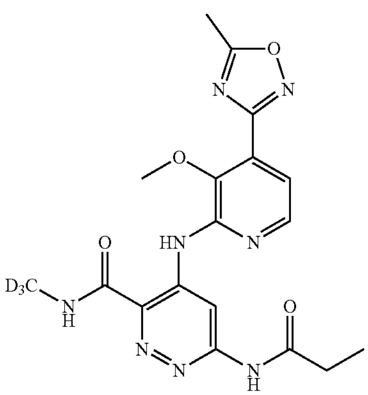 | 415.4 | 416.2 | 1.23 | D |
| 82 | 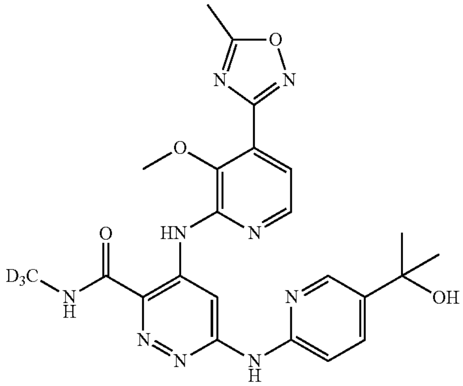 [SMILES: [2H]C([2H])([2H])NC(=O)c1nnc(Nc2ccc(C(C)(C)O)cn2)cc1Nc1nccc(-c2noc(C)n2)c1OC] | 494.5 | 495.0 | 1.49 | D |

Example 83

6-(cyclopropanecarboxamido)-4-((3'-methoxy-[2,4'-bipyridin]-2'-yl)amino)-N-(methyl-d3)pyridazine-3-carboxamide

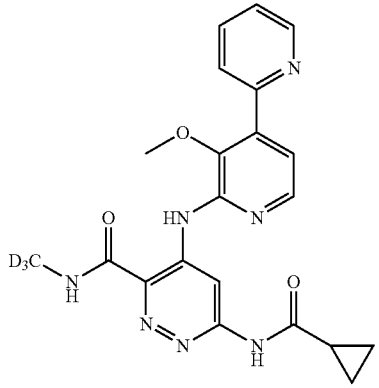 [SMILES: [2H]C([2H])([2H])NC(=O)c1nnc(NC(=O)C2CC2)cc1Nc1nccc(-c2ccccn2)c1OC]

Step 1. Synthesis of 3'-Methoxy-[2,4'-bipyridin]-2'-amine

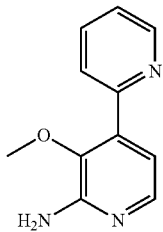

A mixture of 4-bromo-3-methoxypyridin-2-amine (90 mg, 0.443 mmol), 2-(tributylstannyl)pyridine (245 mg, 0.665 mmol), and bis(triphenylphosphine) palladium(II) chloride (46.7 mg, 0.066 mmol) in 1,4-dioxane (3.5 mL) was heated at 115° C. for 16 h. Upon cooling to rt, the mixture was diluted with ethyl acetate (15 mL) and filtered through Celite. The filtrate was concentrated under vacuum. The residue was subjected to flash chromatograph (24 g silica gel, solid loading, 100% ethyl acetate) to provide the desired product, 3'-methoxy-[2,4'-bipyridin]-2'-amine (64.0 mg, 0.318 mmol, 71.8% yield), as a white solid. LCMS m/z=202.1 (M+H)$^+$.

Step 2. Synthesis of 6-Chloro-4-((3'-methoxy-[2,4'-bipyridin]-2'-yl)amino)-N-(methyl-d3)pyridazine-3-carboxamide

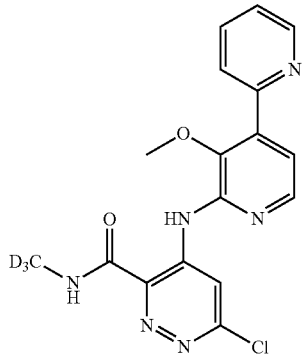 [SMILES: [2H]C([2H])([2H])NC(=O)c1nnc(Cl)cc1Nc1nccc(-c2ccccn2)c1OC]

To a solution of 4,6-dichloro-N-trideuteromethylpyridazine-3-carboxamide and 3'-methoxy-[2,4'-bipyridin]-2'-amine (63.7 mg, 0.316 mmol) in tetrahydrofuran (4 mL) at rt was added lithium bis(trimethylsilyl)amide in THF (0.753 mL, 0.753 mmol) over 2 min. The resulting mixture was stirred at rt for 1 h. The reaction was quenched with water (2 mL). The mixture was adjusted with 1 N HCl solution to pH 9-10, diluted with ethyl acetate (80 mL), and washed with water (20 mL) and brine (20 mL). The organic layer was dried over anhydrous MgSO$_4$ and concentrated under vacuum. The residue was subjected to flash chromatograph (24 g silica gel, solid loading, 35-80% ethyl acetate/dichloromethane) to provide the desired product, 6-chloro-4-((3'-methoxy-[2,4'-bipyridin]-2'-yl)amino)-N-trideuteromethylpyridazine-3-carboxamide (47.6 mg, 0.127 mmol, 42.3% yield), as a white solid. LCMS m/z=373.9 (M+H)$^+$.

Step 3. Synthesis of 6-(Cyclopropanecarboxamido)-4-((3'-methoxy-[2,4'-bipyridin]-2'-yl)amino)-N-(methyl-d3)pyridazine-3-carboxamide A mixture of 6-chloro-4-((3'-methoxy-[2,4'-bipyridin]-2'-yl)amino)-N-trideuteromethylpyridazine-3-carboxamide (47.6 mg, 0.127 mmol), cyclopropanecarboxamide (27.1 mg, 0.318 mmol), tris(dibenzylideneacetone) dipalladium (0) (17.49 mg, 0.019 mmol), xantphos (11.05 mg, 0.019 mmol), and cesium carbonate (104 mg, 0.318 mmol) in 1,4-dioxane (2.2 mL) and NMP (0.3 mL) was heated under microwave at 145° C. for 1 h. The mixture was diluted with ethyl acetate (8 mL) and filtered through celite. The filtrate was concentrated under vacuum. To the residue was added DMSO (1.5 mL), followed by water (20 mL). The insoluble material was collected as beige solid by suction filtration and dried at 50° C. under vacuum. This material was further purified by flash chromatograph (24 g silica gel, solid loading, 0-6% MeOH/CH2Cl2) to provide the desired product, 6-(cyclopropanecarboxamido)-4-((3'-methoxy-[2,4'-bipyridin]-2'-yl)amino)-N-trideuteromethylpyridazine-3-carboxamide (21.9 mg, 0.050 mmol, 39.5% yield), as a pale yellow solid. LCMS m/z=423.0 (M+H)$^+$; $^1$H NMR (400 MHz, DMSO-d$_6$) δ 12.44 (s, 1H), 11.34 (s, 1H), 9.88 (s, 1H), 9.24 (s, 1H), 8.85-8.72 (m, 1H), 8.19 (d, J=5.3 Hz, 1H), 8.03-7.95 (m, 2H), 7.53-7.48 (m, 1H), 7.37 (d, J=5.3 Hz, 1H), 3.63 (s, 3H), 2.19-2.10 (m, 1H), 0.96-0.84 (m, 4H).

Example 84

6-(Cyclopropanecarboxamido)-4-((3'-methoxy-[2,4'-bipyridin]-2'-yl)amino)-N-(methyl-d3)nicotinamide

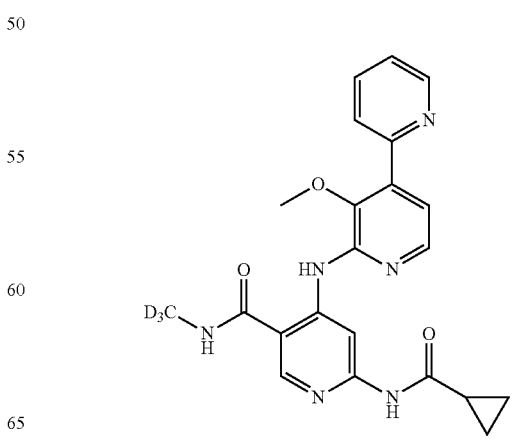

Step 1. Synthesis of 6-Chloro-4-((3'-methoxy-[2,4'-bipyridin]-2'-yl)amino)-N-(methyl-d3)nicotinamide

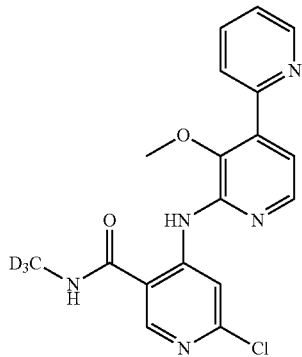 [SMILES: [2H]C([2H])([2H])NC(=O)c1cnc(Cl)cc1Nc1nccc(-c2ccccn2)c1OC]

To a solution of 4,6-dichloro-N-trideuteromethylpyridazine-3-carboxamide and 3'-methoxy-[2,4'-bipyridin]-2'-amine (62.6 mg, 0.311 mmol) in tetrahydrofuran (4 mL) at rt was added lithium bis(trimethylsilyl)amide in THF (0.740 mL, 0.740 mmol) over 2 min. The resulting mixture was stirred at rt for 2.5 h. The reaction was quenched with water (2 mL). The mixture was adjusted with 1 N HCl solution to pH 9-10, diluted with ethyl acetate (80 mL), and washed with water (20 mL) and brine (20 mL). The organic layer was dried over anhydrous MgSO₄ and concentrated under vacuum. The residue was subjected to flash chromatograph (24 g silica gel, solid loading, 50-100% ethyl acetate/dichloromethane) to provided the desired product (37.0 mg, 0.099 mmol, 33.5% yield) as a white solid. LCMS m/z=372.9 (M+H)⁺.

Step 2. Synthesis of 6-(Cyclopropanecarboxamido)-4-((3'-methoxy-[2,4'-bipyridin]-2'-yl)amino)-N-(methyl-d3)nicotinamide A mixture of 6-chloro-4-((3'-methoxy-[2,4'-bipyridin]-2'-yl)amino)-N-trideuteromethylnicotinamide (37 mg, 0.099 mmol), cyclopropanecarboxamide (21.11 mg, 0.248 mmol), tris(dibenzylideneacetone)dipalladium(0) (13.63 mg, 0.015 mmol), xantphos (8.61 mg, 0.015 mmol), and cesium carbonate (81 mg, 0.248 mmol) in 1,4-dioxane (2.2 mL) and NMP (0.3 mL) was heated under microwave at 145° C. for 1 h. The mixture was diluted with ethyl acetate (8 mL) and filtered through celite. The filtrate was diluted with DMSO and MeOH, and injected to prep. HPLC. The correct practions were combined, concentrated under vacuum, basified with 1.5 M K₂HPO₄ solution to pH 9-10, and extracted with dichloromethane (3×30 mL). The combined extract was dried over anhydrous NaSO₄ and concentrated under vacuum. The residue was further purified by flash chromatograph (12 g silica gel, solid loading, 1-8% methano/dichloromethane) to provide the desired product, 6-(cyclopropanecarboxamido)-4-((3'-methoxy-[2,4'-bipyridin]-2'-yl)amino)-N-trideuteromethylnicotinamide (13.2 mg, 0.031 mmol, 30.9% yield), as a pale solid. LCMS m/z=422.0 (M+H)⁺; ¹H NMR (400 MHz, DMSO-d₆) δ 12.01 (s, 1H), 10.77 (br s, 1H), 9.57 (s, 1H), 8.80-8.74 (m, 1H), 8.67 (s, 1H), 8.60 (s, 1H), 8.14 (d, J=5.1 Hz, 1H), 8.04-7.94 (m, 2H), 7.49 (ddd, J=6.7, 4.7, 2.1 Hz, 1H), 7.31 (d, J=5.3 Hz, 1H), 3.60 (s, 3H), 2.10-1.99 (m, 1H), 0.90-0.78 (m, 4H).

Example 85

6-(Cyclopropanecarboxamido)-4-((5-(cyclopropanecarboxamido)-3'-methoxy-[2,4'-bipyridin]-2'-yl)amino)-N-(methyl-d3)nicotinamide

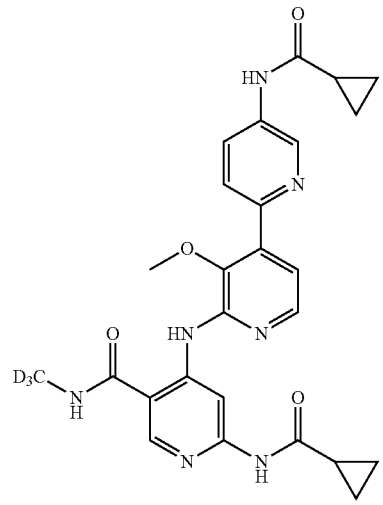 [SMILES: [2H]C([2H])([2H])NC(=O)c1cnc(NC(=O)C2CC2)cc1Nc1nccc(-c2ccc(NC(=O)C3CC3)cn2)c1OC]

Step 1. Synthesis of 5-Chloro-3'-methoxy-[2,4'-bipyridin]-2'-amine

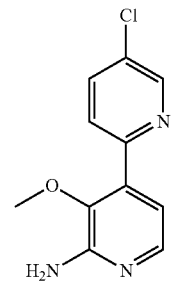 [SMILES: COc1c(-c2ccc(Cl)cn2)ccnc1N]

A mixture of 4-bromo-3-methoxypyridin-2-amine (180 mg, 0.887 mmol), 5-chloro-2-(tributylstannyl)pyridine (535 mg, 1.330 mmol), and bis(triphenylphosphine)palladium(II) chloride (93 mg, 0.133 mmol) in 1,4-dioxane (8 mL) was heated at 115° C. for 16 h. The mixture was diluted with ethyl acetate (15 mL) and filtered through Celite. The filtrate was concentrated under vacuum. The residue was subjected to flash chromatograph (24 g silica gel, solid loading, 100% ethyl acetate) to provide the desired product, 5-chloro-3'-methoxy-[2,4'-bipyridin]-2'-amine (177 mg, 0.751 mmol, 85% yield), as a white solid. LCMS m/z=236.0 (M+H)⁺.

Step 2. Synthesis of 6-Chloro-4-((5-chloro-3'-methoxy-[2,4'-bipyridin]-2'-yl)amino)-N-(methyl-d3)nicotinamide

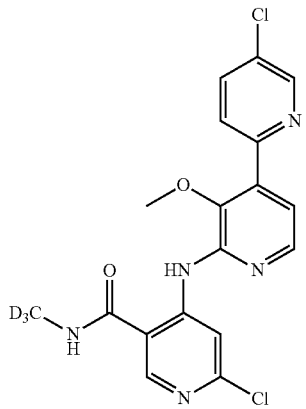 [SMILES: [2H]C([2H])([2H])NC(=O)c1cnc(Cl)cc1Nc1nccc(-c2ccc(Cl)cn2)c1OC]

To a solution of 4,6-dichloro-N-trideuteromethylpyridazine-3-carboxamide and 5-chloro-3'-methoxy-[2,4'-bipyridin]-2'-amine (88 mg, 0.373 mmol) in tetrahydrofuran (5 mL) at rt was added lithium bis(trimethylsilyl)amide in THF (0.889 mL, 0.889 mmol) over 2 min. The resulting mixture was stirred at rt for 90 min. The reaction was quenched with water (2 mL). The mixture was adjusted with 1 N HCl solution to pH 9-10, diluted with ethyl acetate (80 mL), and washed with water (20 mL) and brine (20 mL). The organic layer was dried over anhydrous $MgSO_4$ and concentrated under vacuum. The residue was subjected to flash chromatograph (24 g silica gel, solid loading, 50-100% ethyl acetate/dichloromethane) to provide the desired product (68 mg, 0.167 mmol, 46.9% yield) as a white solid.

Step 3. Synthesis of 6-(Cyclopropanecarboxamido)-4-((5-(cyclopropanecarboxamido)-3'-methoxy-[2,4'-bipyridin]-2'-yl)amino)-N-(methyl-d3)nicotinamide A mixture of 6-Chloro-4-((5-chloro-3'-methoxy-[2,4'-bipyridin]-2'-yl)amino)-N-(methyl-d3)nicotinamide (40 mg, 0.098 mmol), cyclopropanecarboxamide (20.90 mg, 0.246 mmol), tris(dibenzylideneacetone)dipalladium(0) (13.49 mg, 0.015 mmol), xantphos (8.52 mg, 0.015 mmol), and cesium carbonate (80 mg, 0.246 mmol) in 1,4-dioxane (2.2 mL) and NMP (0.3 mL) was heated under microwave at 140° C. for 1 h. The mixture was diluted with ethyl acetate (8 mL) and filtered through celite. The filtrate was concentrated under vacuum. The residue was dissolved in DMSO (2 mL) and submitted to SCP group for purification to provide the desired product (20 mg, 37% yield). LCMS m/z=505.2 (M+H)$^+$; $^1$H NMR (500 MHz, DMSO-$d_6$) δ 11.98 (br s, 1H), 10.76 (s, 1H), 10.67 (s, 1H), 9.58 (s, 1H), 8.90 (s, 1H), 8.68 (s, 1H), 8.58 (s, 1H), 8.22 (br d, J=8.2 Hz 1H), 8.11 (d. J=5.1 Hz, 1H), 8.01 (br d, J=8.6 Hz, 1H), 7.34 (d, J=5.1 Hz, 1H), 3.60 (s, 3H), 2.03 (br s, 1H), 1.88-1.81 (m, 1H), 0.93-0.76 (m, 8H).

Example 86

4-((5-Chloro-3'-methoxy-[2,4'-bipyridin]-2'-yl)amino)-6-(cyclopropanecarboxamido)-N-(methyl-d3)nicotinamide

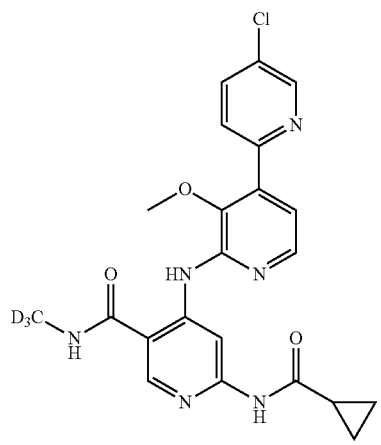 [SMILES: [2H]C([2H])([2H])NC(=O)c1cnc(NC(=O)C2CC2)cc1Nc1nccc(-c2ccc(Cl)cn2)c1OC]

A mixture of 6-chloro-4-((5-chloro-3'-methoxy-[2,4'-bipyridin]-2'-yl)amino)-N-trideuteromethylnicotinamide (53 mg, 0.130 mmol), cyclopropanecarboxamide (11.30 mg, 0.133 mmol), tris(dibenzylideneacetone)dipalladium(0) (17.88 mg, 0.020 mmol), xantphos (11.29 mg, 0.020 mmol), and cesium carbonate (106 mg, 0.325 mmol) in 1,4-dioxane (2.5 mL) and NMP (0.3 mL) was heated under microwave at 135° C. for 1 h. The mixture was diluted with ethyl acetate (8 mL) and filtered through celite. The filtrate was concentrated under vacuum. The residue was dissolved in DMSO and MeOH, and injected to prep. HPLC. The correct fractions were combined, concentrated under vacuum, basified with 1.5 M $K_2HPO_4$ solution to pH 9-10, and extracted with dichloromethane (3×35 mL). The combined extract was dried over anhydrous $MgSO_4$. Removal of solvent under vacuum provided the desired product, 4-((5-chloro-3'-methoxy-[2,4'-bipyridin]-2'-yl)amino)-6-(cyclopropanecarboxamido)-N-trideuteromethyl nicotinamide (4.6 mg, 9.38 μmol, 7.21% yield), as a yellow solid. LCMS m/z=455.9 (M+H)$^+$; $^1$H NMR (400 MHz, DMSO-$d_6$) δ 12.05 (s, 1H), 10.93-10.72 (m, 1H), 9.55 (s, 1H), 8.82 (dd, J=2.5, 0.7 Hz, 1H), 8.72-8.67 (m, 1H), 8.60 (s, 1H), 8.18-8.09 (m, 2H), 8.07-8.02 (m, 1H), 7.31 (d, J=5.3 Hz, 1H), 3.61 (s, 3H), 2.09-1.99 (m, 1H), 0.90-0.81 (m, 4H)

Example 87

6-(Cyclopropanecarboxamido)-4-((4-(5-(dimethyl-carbamoyl)pyrazin-2-yl)-3-methoxypyridin-2-yl)amino)-N-(methyl-d3)pyridazine-3-carboxamide

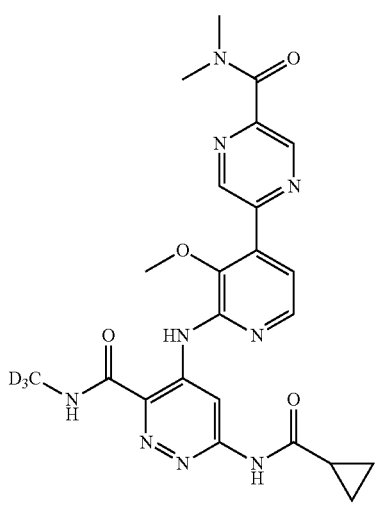 [SMILES: [2H]C([2H])([2H])NC(=O)c1nnc(NC(=O)C2CC2)cc1Nc1nccc(-c2cnc(C(=O)N(C)C)cn2)c1OC]

Step 1. Synthesis of 5-Chloro-N,N-dimethylpyrazine-2-carboxamide

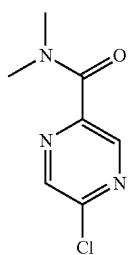

To a suspension of 5-chloropyrazine-2-carboxylic acid (1.00 g, 6.31 mmol) in dichloromethane (12 mL) and DMF (0.015 mL) at rt was added oxalyl chloride (0.804 mL, 7.25 mmol) dropwise over 10 min. The mixture was stirred at rt for 2 h before it was concentrated under vacuum to dryness. The residue was dissolved in dichloromethane (15 mL). Dimethylamine in THF (3.94 mL, 7.88 mmol) was added at rt over 10 min, followed by triethylamine (1.934 mL, 13.88 mmol). The mixture was stirred at rt for 2 h. The mixture was diluted with ethyl acetate (50 mL) and filtered through Celite. The filtrate was concentrated under vacuum to dryness, and the residue was applied to flash chromatograph (80 g silica gel, solid loading, 65-100% ethyl acetate) to provide the desired product, 5-chloro-N,N-dimethylpyrazine-2-carboxamide (1.07 g, 5.76 mmol, 91% yield), as a white solid. LCMS m/z=186.1 (M+H)+.

Step 2. Synthesis of N,N-Dimethyl-5-(trimethyl-stannyl)pyrazine-2-carboxamide

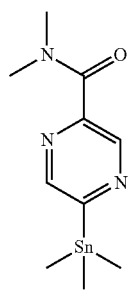

A mixture of 5-chloro-N,N-dimethylpyrazine-2-carboxamide (300 mg, 1.616 mmol), tetrabutylammonium iodide (657 mg, 1.778 mmol), 1,1,1,2,2,2-hexamethyldistannane (0.402 mL, 1.940 mmol), and tetrakis(triphenylphosphine)palladium(0)(112 mg, 0.097 mmol) in toluene (8 mL) was degassed and heated at 105° C. for 16 h. Upon cooling to rt, the mixture was diluted with ethyl acetate (15 mL) and filtered through Celite. The filtrate was concentrated under vacuum, and the residue was subjected to flash chromatograph (80 g silica gel, solid loading, 35-85% ethyl acetate/hexane) to provide the desired product, N,N-dimethyl-5-(trimethylstannyl)pyrazine-2-carboxamide (96 mg, 0.306 mmol, 18.92% yield), as a light yellow solid. LCMS m/z=315.9 (M+H)+.

Step 3. Synthesis of 5-(2-Amino-3-methoxypyridin-4-yl)-N,N-dimethylpyrazine-2-carboxamide

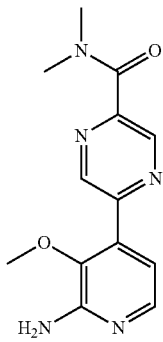 [SMILES: COc1c(-c2cnc(C(=O)N(C)C)cn2)ccnc1N]

A mixture of 4-bromo-3-methoxypyridin-2-amine (133 mg, 0.655 mmol), N,N-dimethyl-5-(trimethylstannyl)pyrazine-2-carboxamide (226 mg, 0.721 mmol), and bis(triphenylphosphine)palladium(II) chloride (69.0 mg, 0.098 mmol) in 1,4-dioxane (6 mL) was heated at 115° C. for 16 h. The mixture was diluted with ethyl acetate (15 mL) and filtered through Celite. The filtrate was concentrated under vacuum. The residue was subjected to flash chromatograph (24 g silica gel, solid loading, 0-6% MeOH/CH2Cl2) to provide the desired product, 5-(2-amino-3-methoxypyridin-4-yl)-N,N-dimethylpyrazine-2-carboxamide (88 mg, 0.322 mmol, 49.2% yield), as a white solid. LCMS m/z=274.0 (M+H)+.

Step 4. Synthesis of 6-Chloro-4-((4-(5-(dimethylcarbamoyl)pyrazin-2-yl)-3-methoxypyridin-2-yl)amino)-N-(methyl-d3)pyridazine-3-carboxamide

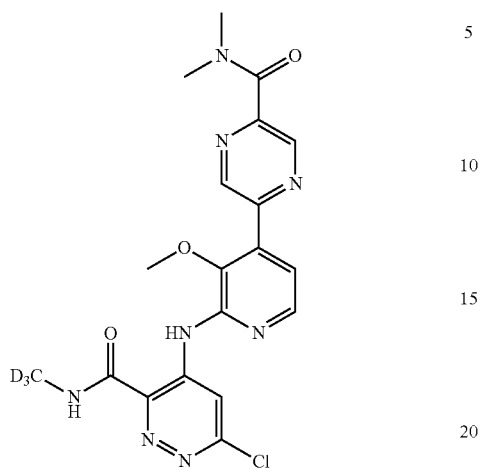

To a solution of 4,6-dichloro-N-trideuteromethylpyridazine-3-carboxamide and 5-(2-amino-3-methoxypyridin-4-yl)-N,N-dimethylpyrazine-2-carboxamide (109 mg, 0.400 mmol) in tetrahydrofuran (6 mL) at rt was added lithium bis(trimethylsilyl)amide in THF (0.981 mL, 0.981 mmol) over 2 min. The resulting mixture was stirred at rt for 1 h. The reaction was quenched with water (60 mL). The mixture was adjusted with 1 N HCl solution to pH 9-10. The insoluble product, 6-chloro-4-((4-(5-(dimethylcarbamoyl)pyrazin-2-yl)-3-methoxypyridin-2-yl)amino)-N-trideuteromethylpyridazine-3-carboxamide (91 mg, 0.204 mmol, 52.0% yield), was collected as a beige solid by suction filtration and dried at 50° C. under vacuum. LCMS m/z=445.9 (M+H)$^+$.

Step 5. Synthesis of 6-(Cyclopropanecarboxamido)-4-((4-(5-(dimethylcarbamoyl)pyrazin-2-yl)-3-methoxypyridin-2-yl)amino)-N-(methyl-d3)pyridazine-3-carboxamide A mixture of Reactant 1 (45 mg, 0.101 mmol), cyclopropanecarboxamide (21.47 mg, 0.252 mmol), tris(dibenzylideneacetone)dipalladium(0) (13.86 mg, 0.015 mmol), xantphos (8.76 mg, 0.015 mmol), and cesium carbonate (82 mg, 0.252 mmol) in 1,4-dioxane (2.6 mL) and NMP (0.4 mL) was heated under microwave at 145° C. for 1 h. The mixture was diluted with ethyl acetate (8 mL) and filtered through celite. The filtrate was concentrated under vacuum. The residue was dissolved in DMSO and MeOH, and injected to prep. HPLC. The correct fractions were combined, concentrated under vacuum, basified with 1.5 M K$_2$HPO$_4$ solution to pH 9, and extracted with dichloromethane (3×35 mL). The combined extract was dried over anhydrous Na$_2$SO$_4$, and concentrated under vacuum. The residue was further purified by flash chromatograph (24 g silica gel, solid loading, 0-7% MeOH/dichloromethane) to give the desired product, 6-(cyclopropanecarboxamido)-4-((4-(5-(dimethylcarbamoyl)pyrazin-2-yl)-3-methoxypyridin-2-yl)amino)-N-trideuteromethylpyridazine-3-carboxamide (10.4 mg, 0.021 mmol, 20.63% yield), as a yellow solid. LCMS m/z=495.0 (M+H)$^+$; $^1$H NMR (400 MHz, DMSO-d$_6$) δ 12.50 (s, 1H), 11.36 (s, 1H), 9.88 (s, 1H), 9.26 (s, 1H), 9.21 (d, J=1.5 Hz, 1H), 9.02 (d, J=1.5 Hz, 1H), 8.26 (d, J=5.3 Hz, 1H), 7.44 (d, J=5.3 Hz, 1H), 3.71 (s, 3H), 3.08 (s, 3H), 3.06 (s, 3H), 2.19-2.11 (m, 1H), 0.95-0.86 (m, 4H).

Example 88

6-(Cyclopropanecarboxamido)-4-((4-(5-(ethyl(methyl)carbamoyl)pyrazin-2-yl)-3-methoxypyridin-2-yl)amino)-N-(methyl-d3)pyridazine-3-carboxamide

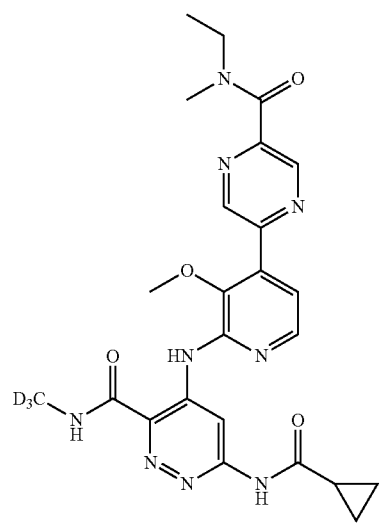 [SMILES: [2H]C([2H])([2H])NC(=O)c1nnc(NC(=O)C2CC2)cc1Nc1nccc(-c2cnc(C(=O)N(C)CC)cn2)c1OC]

This compound was prepared using a similar procedure used to prepare Example 87. LCMS m/z=509.0 (M+H)$^+$; $^1$H NMR (400 MHz, DMSO-d$_6$) δ 12.52 (s, 1H), 11.40 (s, 1H), 9.89 (d, J=2.4 Hz, 1H), 9.29 (s, 1H), 9.21 (dd, J=5.0, 1.5 Hz, 1H), 9.02 (dd, J=2.9, 1.5 Hz, 1H), 8.26 (d, J=5.3 Hz, 1H), 7.44 (d, J=5.1 Hz, 1H), 3.70 (s, 3H), 3.55 (q, J=7.1 Hz, 1H), 3.41-3.35 (m, 1H), 3.04 (d, J=8.3 Hz, 3H), 2.20-2.07 (m, 1H), 1.23-1.12 (m, 3H), 0.96-0.82 (m, 4H).

Example 89

6-(2-Cyclopropylacetamido)-4-((4-(5-(dimethylcarbamoyl)pyrazin-2-yl)-3-methoxypyridin-2-yl)amino)-N-(methyl-d3)pyridazine-3-carboxamide

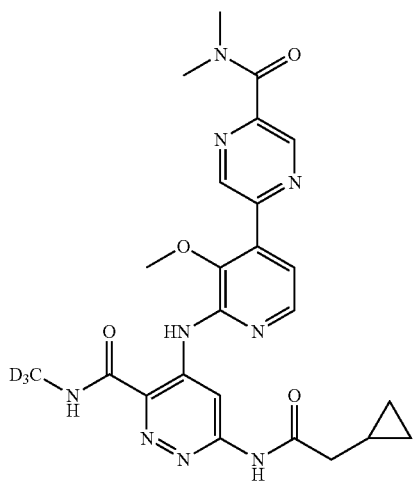 [SMILES: [2H]C([2H])([2H])NC(=O)c1nnc(NC(=O)CC2CC2)cc1Nc1nccc(-c2cnc(C(=O)N(C)C)cn2)c1OC]

This compound was prepared using a similar procedure used to prepare Example 87. LCMS m/z=509.1 (M+H)+; 1H NMR (400 MHz, DMSO-d6) δ 12.51 (s, 1H), 10.95 (s, 1H), 9.93 (s, 1H), 9.26 (s, 1H), 9.22 (d, J=1.5 Hz, 1H), 9.03 (d, J=1.5 Hz, 1H), 8.30 (d, J=5.3 Hz, 1H), 7.46 (d, J=5.3 Hz, 1H), 3.72 (s, 3H), 3.09 (s, 3H), 3.06 (s, 3H), 2.40 (d, J=7.0 Hz, 2H), 1.17-1.05 (m, 1H), 0.55-0.48 (m, 2H), 0.26-0.20 (m, 2H).

Example 90

4-((4-(5-(Dimethylcarbamoyl)pyrazin-2-yl)-3-methoxypyridin-2-yl)amino)-N-(methyl-d3)-6-((1-methyl-1H-pyrazol-3-yl)amino)pyridazine-3-carboxamide

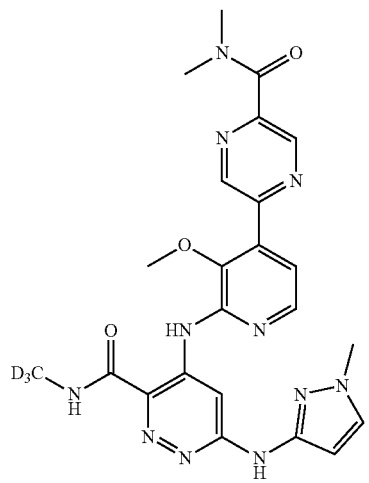 [SMILES: [2H]C([2H])([2H])NC(=O)c1nnc(Nc2ccn(C)n2)cc1Nc1nccc(-c2cnc(C(=O)N(C)C)cn2)c1OC]

A mixture of 6-chloro-4-((4-(5-(dimethylcarbamoyl)pyrazin-2-yl)-3-methoxypyridin-2-yl)amino)-N-trideuteromethylpyridazine-3-carboxamide (30 mg, 0.067 mmol), 1-methyl-1H-pyrazol-3-amine (13.07 mg, 0.135 mmol), and 4-methylbenzenesulfonic acid monohydrate (19.20 mg, 0.101 mmol) in THF (2.0 mL) was heated in a closed vial at 100° C. for 20 h. The mixture was then concentrated under vacuum to dryness. The residue was dissolved in DMSO and MeOH, and injected to prep. HPLC. The correct fractions were combined, concentrated under vacuum basified with 1.5 M $K_2HPO_4$ solution to pH 9-10, and extracted with dichloromethane (3×35 mL). The combined extract was dried over anhydrous $NaSO_4$. Removal of solvent under vacuum provided the desired product, 4-((4-(5-(dimethylcarbamoyl)pyrazin-2-yl)-3-methoxypyridin-2-yl)amino)-N-trideuteromethyl-6-((1-methyl-1H-pyrazol-3-yl)amino)pyridazine-3-carboxamide (14.3 mg, 0.027 mmol, 40.7% yield), as a yellow solid. LCMS m/z=507.2 (M+H)+; 1H NMR (400 MHz, DMSO-d6) δ 12.39 (s, 1H), 9.91 (s, 1H), 9.28 (s, 1H), 9.22 (d, J=1.6 Hz, 1H), 9.15 (s, 1H), 9.02 (d, J=1.5 Hz, 1H), 8.28 (d, J=5.1 Hz, 1H), 7.60 (d, J=2.1 Hz, 1H), 7.42 (d, J=5.3 Hz, 1H), 6.30 (d, J=2.1 Hz, 1H), 3.82 (s, 3H), 3.71 (s, 3H), 3.09 (s, 3H), 3.06 (s, 3H).

Example 91

6-((1,5-Dimethyl-1H-pyrazol-3-yl)amino)-4-((4-(5-(dimethylcarbamoyl)pyrazin-2-yl)-3-methoxypyridin-2-yl)amino)-N-(methyl-d3)pyridazine-3-carboxamide

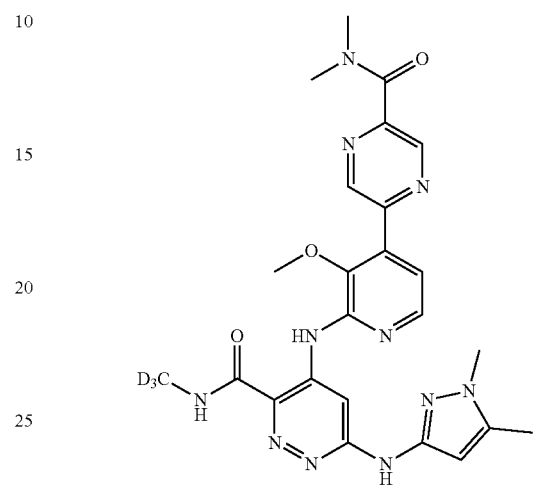

This compound was prepared using a similar procedure used to prepare Example 90. LCMS m/z=521.2 (M+H); 1H NMR (400 MHz, DMSO-d6) δ 12.38 (s, 1H), 9.80 (s, 1H), 9.31 (s, 1H), 9.22 (d, J=1.5 Hz, 1H), 9.13 (s, 1H), 9.02 (d, J=1.6 Hz, 1H), 8.28 (d, J=5.3 Hz, 1H), 7.42 (d, J=5.1 Hz, 1H), 6.11 (s, 1H), 3.71 (s, 3H), 3.70 (s, 3H), 3.09 (s, 3H), 3.06 (s, 3H), 2.26 (s, 3H).

Example 92

6-((5-Chloro-1-methyl-1H-pyrazol-3-yl)amino)-4-((4-(5-(dimethylcarbamoyl)pyrazin-2-yl)-3-methoxypyridin-2-yl)amino)-N-(methyl-d3)pyridazine-3-carboxamide

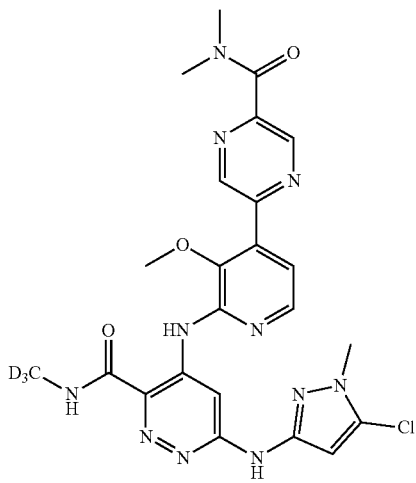 [SMILES: [2H]C([2H])([2H])NC(=O)c1nnc(Nc2cc(Cl)n(C)n2)cc1Nc1nccc(-c2cnc(C(=O)N(C)C)cn2)c1OC]

This compound was prepared using a similar procedure used to prepare Example 90. LCMS m/z=541.1 (M+H)+; 1H NMR (400 MHz, DMSO-d$_6$) δ 12.41 (s, 1H), 10.06 (s, 1H), 9.24-9.20 (m, 2H), 9.17 (s, 1H), 9.02 (d, J=1.5 Hz, 1H), 8.29 (d, J=5.1 Hz, 1H), 7.43 (d, J=5.1 Hz, 1H), 6.48 (s, 1H), 3.78 (s, 3H), 3.71 (s, 3H), 3.08 (s, 3H), 3.06 (s, 3H).

Example 93

4-((4-(5-fluoropyrimidin-2-yl)-3-methoxypyridin-2-yl)amino)-6-((5-(2-hydroxypropan-2-yl)pyridin-2-yl)amino)-N-(methyl-d3)pyridazine-3-carboxamide

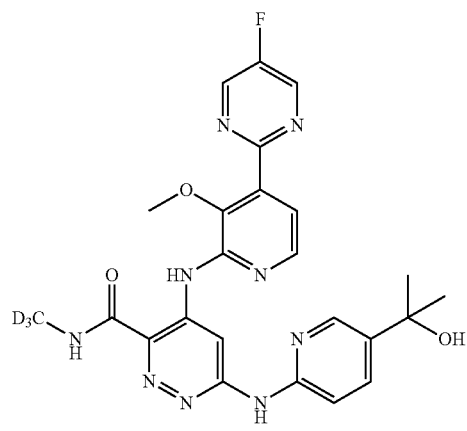 [SMILES: [2H]C([2H])([2H])NC(=O)c1nnc(Nc2ccc(C(C)(C)O)cn2)cc1Nc1nccc(-c2ncc(F)cn2)c1OC]

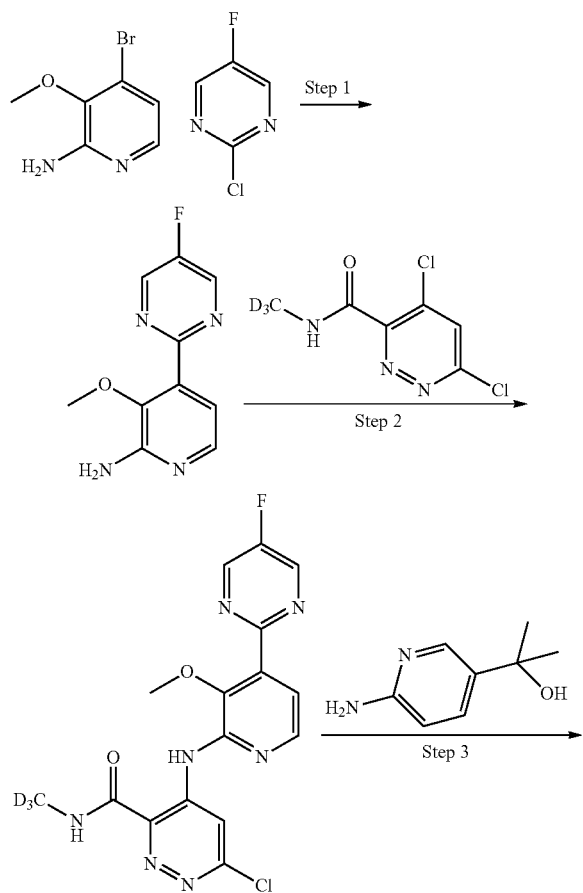

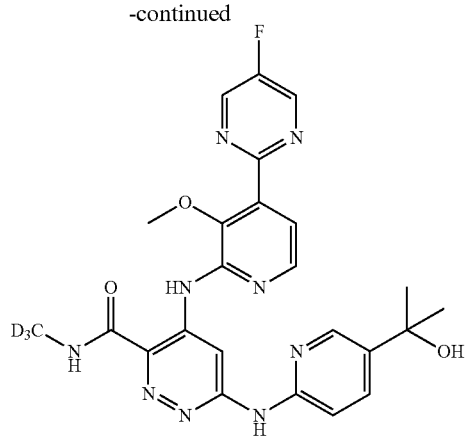

Step 1

4-bromo-3-methoxypyridin-2-amine (500 mg, 2.463 mmol), bis(pinacolato)diboron (1376 mg, 5.42 mmol), 1,1'-bis(diphenylphosphino)ferrocene-palladium(II)dichloride dichloromethane complex (201 mg, 0.246 mmol) and potassium acetate (725 mg, 7.39 mmol) were mixed in dioxane (20 mL), degassed with nitrogen for 5 min then heated at 100° C. for o/n. After cooling to rt, the reaction mixture was filtered and 1,1'-bis(diphenylphosphino)ferrocene-palladium(II)dichloride dichloromethane complex (201 mg, 0.246 mmol) and 2-chloro-5-fluoropyrimidine (424 mg, 3.20 mmol) were added, then Na2CO3 (3694 µl, 7.39 mmol) (2 M) solution, the mixture was degassed with nitrogen and heated at 105° C. for 4.5 h. LC-MS indicated the completion of the reaction. The mixture was diluted with MeOH (15 mL), and was filtered through a pad of celite and the filtrate was concentrated, the residue was mixed with DCM, and purified with ISCO column (12 g, AcOEt/Hexane=0-100%, gradient time=15 min) to provide 4-(5-fluoropyrimidin-2-yl)-3-methoxypyridin-2-amine. Yield 260 mg (47.9%). LCMS m/z 221.2 (M+H)+; HPLC tR 0.726 min (analytical HPLC Method A); 1H NMR (400 MHz, METHANOL-d4) δ 9.00-8.72 (m, 2H), 7.78 (d, J=5.5 Hz, 1H), 7.00 (d, J=5.3 Hz, 1H), 3.73 (s, 3H).

Step 2

To a clear solution of 4,6-dichloro-N-(methyl-d3)pyridazine-3-carboxamide (195 mg, 0.931 mmol) and 4-(5-fluoropyrimidin-2-yl)-3-methoxypyridin-2-amine (205 mg, 0.931 mmol) in THF (6 ml) was added lithium bis(trimethylsilyl)amide (2327 µl, 2.327 mmol) dropwise at 0° C. slowly, the mixture was stirred at 0-rt for 2.5 h. The mixture was added water (1 ml) at 0° C. with stirring, then with 1N HCl (3 ml), the mixture was stirred at 0° C. for 30 min and the solid was collected with filtration and washed with water (2×), dried to give the desired compound as off white solid: 6-chloro-4-((4-(5-fluoropyrimidin-2-yl)-3-methoxypyridin-2-yl)amino)-N-(methyl-d3)pyridazine-3-carboxamide. Yield 170 mg (46.5%). LCMS m/z 221.2 (M+H)+; HPLC tR 1.13 min (analytical HPLC Method A); 1H NMR (400 MHz, DMSO-d6) δ 12.60 (s, 1H), 9.58-9.45 (m, 1H), 9.26 (s, 1H), 9.13 (d, J=0.9 Hz, 2H), 8.30 (d, J=5.3 Hz, 1H), 7.45 (d, J=5.3 Hz, 1H), 3.82 (s, 3H)

Step 3

To a clear solution of 4,6-dichloro-N-(methyl-d3)pyridazine-3-carboxamide (195 mg, 0.931 mmol) and 4-(5- fluoropyrimidin-2-yl)-3-methoxypyridin-2-amine (205 mg, 0.931 mmol) in THF (6 ml) was added lithium bis(trimethylsilyl)amide (2327 µl, 2.327 mmol) dropwise at 0° C. slowly, the mixture was stirred at 0-rt for 2.5 h. The mixture was added water (1 ml) at 0° C. with stirring, then with 1N HCl (3 ml), the mixture was stirred at 0° C. for 30 min and the solid was collected with filtration and washed with water (2×), dried to give the desired compound as off white solid: 6-chloro-4-((4-(5-fluoropyrimidin-2-yl)-3-methoxypyridin-2-yl)amino)-N-(methyl-d3)pyridazine-3-carboxamide.

Yield 170 mg (46.5%). LCMS m/z 221.2 (M+H)+; HPLC tR 1.13 min (analytical HPLC Method A); 1H NMR (400 MHz, DMSO-d6) δ 12.60 (s, 1H), 9.58-9.45 (m, 1H), 9.26 (s, 1H), 9.13 (d, J=0.9 Hz, 2H), 8.30 (d, J=5.3 Hz, 1H), 7.45 (d, J=5.3 Hz, 1H), 3.82 (s, 3H)

The Examples in Table 3 were prepared using a similar procedure used to prepare Example 93.

TABLE 3

| Ex. Number | Structure | Mol Wt | LCMS m/z observed | HPLC t$_R$ (min) | HPLC method |
|---|---|---|---|---|---|
| 94 | 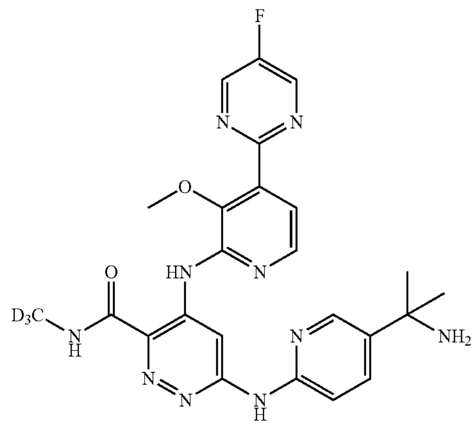 [SMILES: [2H]C([2H])([2H])NC(=O)c1nnc(Nc2ccc(C(C)(C)N)cn2)cc1Nc1nccc(-c2ncc(F)cn2)c1OC] | 507 | 508.4 | 1.09 | A |
| 95 | 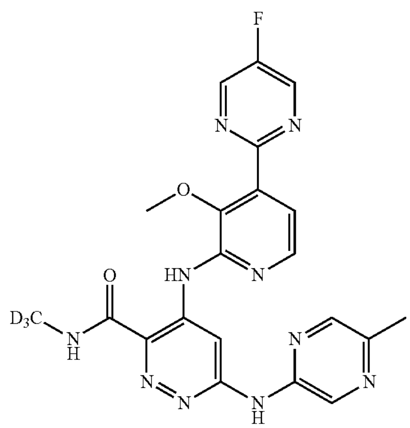 [SMILES: [2H]C([2H])([2H])NC(=O)c1nnc(Nc2cnc(C)cn2)cc1Nc1nccc(-c2ncc(F)cn2)c1OC] | 465 | 466.3 | 0.95 | A |
| 96 | 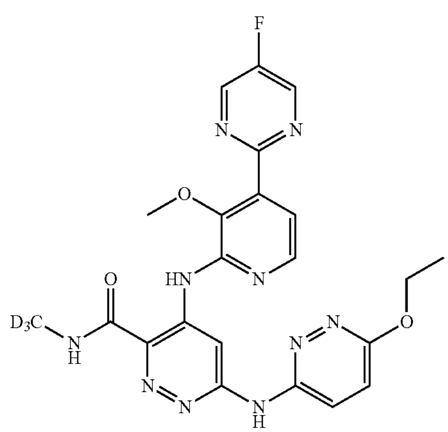 [SMILES: [2H]C([2H])([2H])NC(=O)c1nnc(Nc2ccc(OCC)nn2)cc1Nc1nccc(-c2ncc(F)cn2)c1OC] | 495 | 496.3 | 0.996 | A |

TABLE 3-continued

| Ex. Number | Structure | Mol Wt | LCMS m/z observed | HPLC t$_R$ (min) | HPLC method |
|---|---|---|---|---|---|
| 97 | 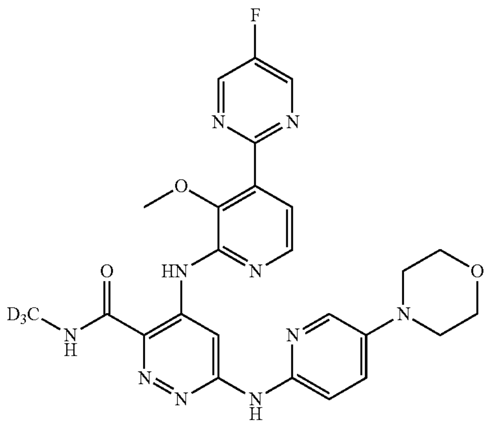 [SMILES: [2H]C([2H])([2H])NC(=O)c1nnc(Nc2ccc(N3CCOCC3)cn2)cc1Nc1nccc(-c2ncc(F)cn2)c1OC] | 535 | 536.6 | 1.06 | A |
| 98 | 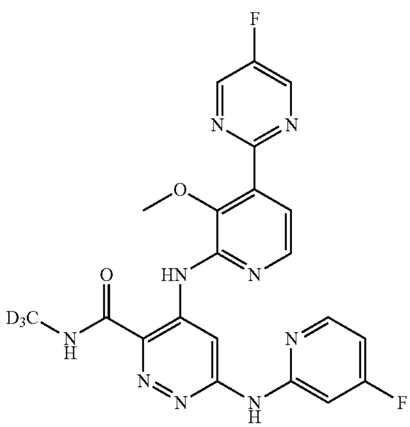 [SMILES: [2H]C([2H])([2H])NC(=O)c1nnc(Nc2cc(F)ccn2)cc1Nc1nccc(-c2ncc(F)cn2)c1OC] | 468 | 469.4 | 0.96 | A |
| 99 | 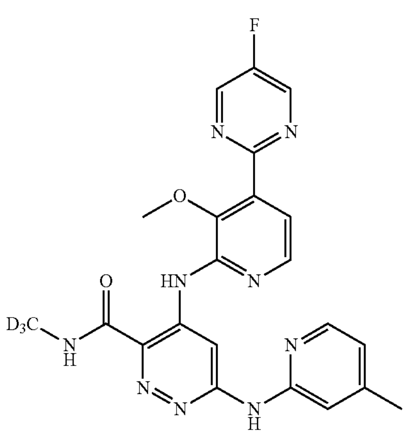 [SMILES: [2H]C([2H])([2H])NC(=O)c1nnc(Nc2cc(C)ccn2)cc1Nc1nccc(-c2ncc(F)cn2)c1OC] | 464 | 465.4 | 0.96 | A |

TABLE 3-continued

| Ex. Number | Structure | Mol Wt | LCMS m/z observed | HPLC $t_R$ (min) | HPLC method |
|---|---|---|---|---|---|
| 100 | 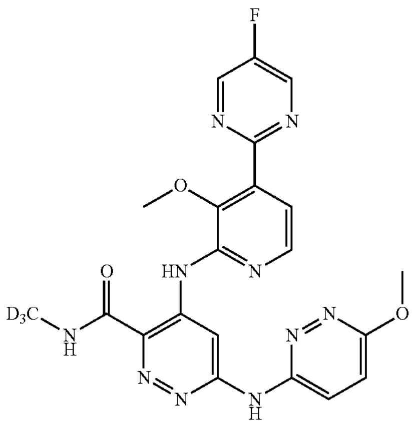 [SMILES: [2H]C([2H])([2H])NC(=O)c1nnc(Nc2ccc(OC)nn2)cc1Nc1nccc(-c2ncc(F)cn2)c1OC] | 481 | 482.3 | 0.96 | A |
| 101 | 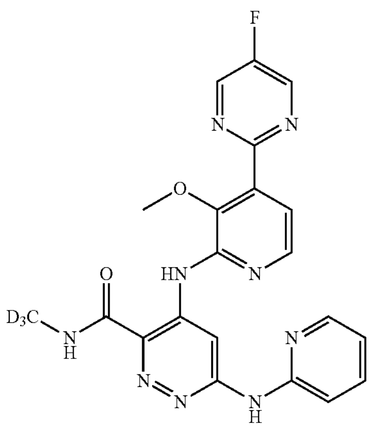 [SMILES: [2H]C([2H])([2H])NC(=O)c1nnc(Nc2ccccn2)cc1Nc1nccc(-c2ncc(F)cn2)c1OC] | 450 | 451.3 | 0.96 | A |
| 102 | 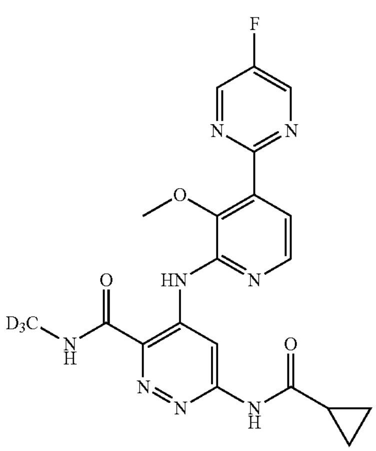 [SMILES: [2H]C([2H])([2H])NC(=O)c1nnc(NC(=O)C2CC2)cc1Nc1nccc(-c2ncc(F)cn2)c1OC] | 441 | 442.3 | 1.04 | A |

Example 103

4-((3-methoxy-4-(2-methyl-2H-tetrazol-5-yl)pyridin-2-yl)amino)-N-(methyl-d3)-6-((4-methylpyridin-2-yl)amino)nicotinamide

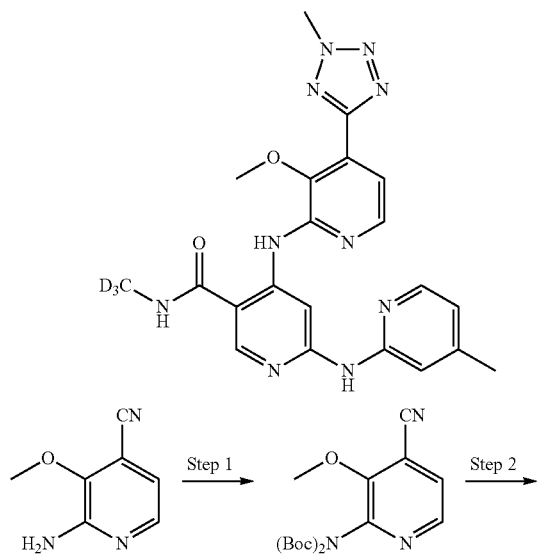

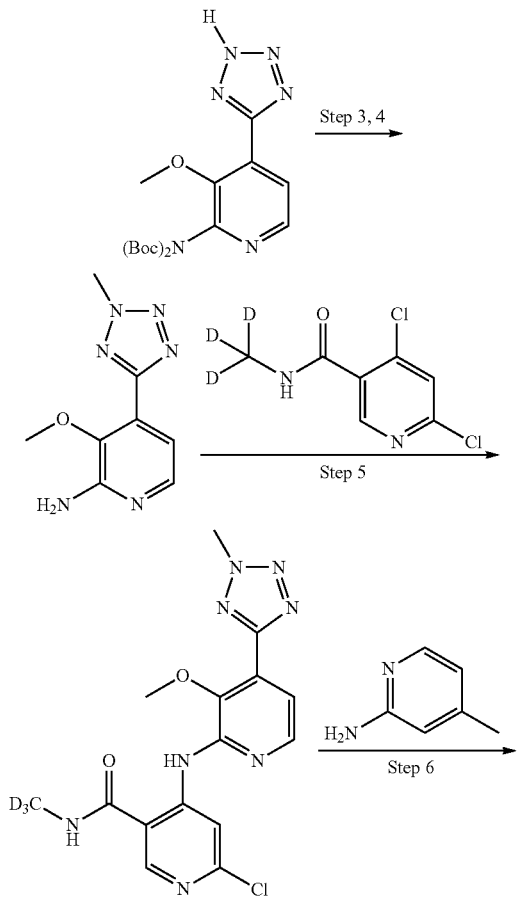

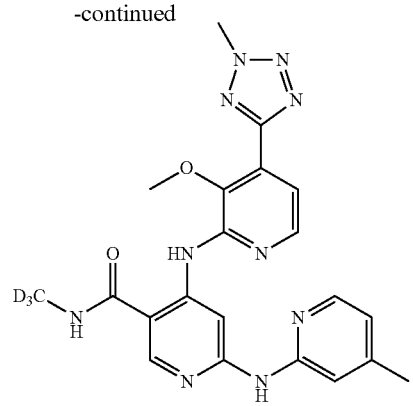

Step 1

To the mixture of 2-amino-3-methoxyisonicotinonitrile (200 mg, 1.341 mmol), Boc-Anhydride (934 μl, 4.02 mmol) in DCM (10 ml) was added TEA (561 μl, 4.02 mmol) and DMAP (164 mg, 1.341 mmol), the mixture was stirred at rt for o/n, and the mixture was quenched with water (5 ml) at 0° C. and diluted with DCM (50 ml), which was washed with sat. NaHCO3 (40 ml), dried (Na2SO4) and concentrated under vacuo and the residue was purified with isco column (25 g, AcOEt/Hexane=0-100%, gradient time=12 min), peak1 (t11, out@35% AcOEt) was the desired product. Yield 320 mg (68.3%). LCMS m/z 350.3 (M+H)+; HPLC tR 1.26 min (analytical HPLC Method A); 1H NMR (400 MHz, CHLOROFORM-d) δ 8.46-8.16 (m, 1H), 7.47 (d, J=5.1 Hz, 1H), 4.15 (s, 3H), 1.46 (s, 18H)

Step 2

The product of step one (320 mg, 0.916 mmol) in anisole (2 ml), TEA (511 μl, 3.66 mmol) were added at 60° C., then AcOH (210 μl, 3.66 mmol) and NaN3 (208 mg, 3.21 mmol), heated at 130° C. (N2) for 4.5 h. The mixture was cooled, then mixed with AcOEt (30 ml) and water (15 ml), shaked and the aqueous layer was extracted one more time with AcOEt (10 ml), the aqueous layer was acidified with 1N HCl to pH=4-5 and extracted with AcOEt (2×20 ml), this organic layer was washed with brine, dried (Na$_2$SO$_4$) and concentrated under vacuo to get the desired product which was used to the next step without further purification. Crude yield 150 mg (41.7%). LCMS m/z 393.4 (M+H)+; HPLC tR 1.06 min (analytical HPLC Method A); 1H NMR (400 MHz, METHANOL-d4) δ 8.59-8.30 (m, 1H), 8.04 (d, J=5.1 Hz, 1H), 3.85 (s, 3H), 1.45 (s, 18H)

Steps 3 and 4

To the product of step 2 (150 mg, 0.382 mmol) in DMF (2 mL) was added K$_2$CO$_3$ (106 mg, 0.765 mmol) and MeI (47.8 μl, 0.765 mmol), the mixture was stirred at rt for o/n. The mixture was diluted with AcOEt (50 ml) and water (20 ml), the org. layer was washed with NaHCO$_3$ (2×20 ml), brine (20 ml), dried (Na$_2$SO$_4$) and concentrated under reduced pressure, the residue was purified with isco column (12 g, AcOEt/Hexane=0-100%, 30 ml/min, gradient 15 min) to get the 2 regioisomers. The less polar one (peak1) is the desired product (out at 50% AcOEt). The product was used to next step. The above product was mixed with DCM (4 ml) and 2 ml of TFA was added and the mixture was stirred at rt for 1.5 h., concentrated under vacuo and the residue was dissolved in DCM (30 ml), which was washed with sat. NaHCO$_3$ (15 ml), the aqueous layer was extracted with DCM (20 ml) and the organic layers were combined and dried (Na2SO4) and concentrated under vacuo to give the desired product. Yield 40 mg (50.7%); LCMS m/z 207.3 (M+H)+; HPLC tR 0.52 min (analytical HPLC Method A): 1H NMR (400 MHz, CHLOROFORM-d) δ 7.95 (d, J=5.3 Hz, 1H), 7.39-7.16 (m, 1H), 4.97 (br. s., 2H), 4.47 (s, 3H), 3.86 (s, 3H)

Step 5

A solution of 3-methoxy-4-(2-methyl-2H-tetrazol-5-yl)pyridin-2-amine (38 mg, 0.184 mmol) and 4,6-dichloro-N-(methyl-d3)nicotinamide (38.3 mg, 0.184 mmol) in DMF (3 ml) was cooled to 0° C. and NaH (29.5 mg, 0.737 mmol) was added in a single portion, after 15 minutes the reaction was taken up to room temp. The reaction was monitored by LCMS. The solution was slowly turned darker and yellowish brown. Quenched after o/n by stirring with saturated aqueous ammonium chloride (2 ml) and water (0.5 ml) at 0° C. Brown precipitate was formed, the mixture was stirred for 30 min. The solid was collected with filtration, washed with water and dried under vacuo to give the desired product which was used as is. Yield 46 mg (66.1%). LCMS m/z 378.0 (M+H)+; HPLC tR 0.83 min (analytical HPLC Method A): 1H NMR (400 MHz, DMSO-d6) δ 12.34-12.05 (m, 1H), 9.01 (s, 1H), 8.96-8.84 (m, 1H), 8.67 (s, 1H), 8.30 (d, J=5.1 Hz, 1H), 7.55 (d, J=5.3 Hz, 1H), 4.51 (s, 3H), 3.90 (s, 3H)

Step 6

A mixture of 6-chloro-4-((3-methoxy-4-(2-methyl-2H-tetrazol-5-yl)pyridin-2-yl)amino)-N-(methyl-d3)nicotinamide (12 mg, 0.032 mmol), 4-methyl pyridine amine (6.87 mg, 0.064 mmol), xantphos (3.68 mg, 6.35 μmol), Cs2CO3 (20.70 mg, 0.064 mmol) and Pd2(dba)3 (2.91 mg, 3.18 μmol) in dioxane (0.5 mL) was sparged with nitrogen for 2 min., then it was stirred at 130° C. for 3 h. After cooling the mixture was concentrated and diluted with DMSO and purified with preparative HPLC.

Yield 4.4 mg (30.6%). LCMS m/z 450.4 (M+H)+; HPLC tR 0.96 min (analytical HPLC Method A); 1H NMR (500 MHz, DMSO-d6) δ 12.12 (s, 1H), 9.77 (br s, 1H), 9.36 (s, 1H), 8.58 (s, 2H), 8.24 (d, J=5.1 Hz, 1H), 8.16 (d, J=5.0 Hz, 1H), 7.53 (s, 1H), 7.47 (d, J=5.1 Hz, 1H), 6.77 (br d, J=5.0 Hz, 1H), 4.51 (s, 3H), 3.45-3.42 (m, 3H), 2.29 (s, 3H)

The Examples in Table 4 were prepared using a similar procedure used to prepare Example 103.

TABLE 4

| Ex. number | Structure | Mol Wt | LCMS m/z observed | HPLC t$_R$ (min) | HPLC method |
|---|---|---|---|---|---|
| 104 | 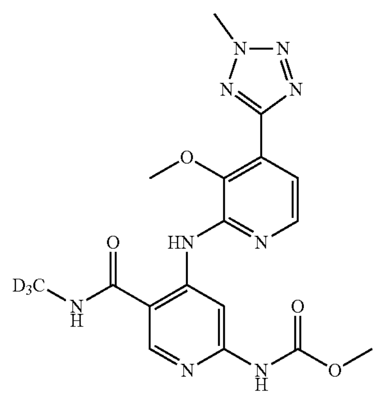 [SMILES: [2H]C([2H])([2H])NC(=O)c1cnc(NC(=O)OC)cc1Nc1nccc(-c2nnn(C)n2)c1OC] | 416 | 417.3 | 0.87 | A |
| 105 | 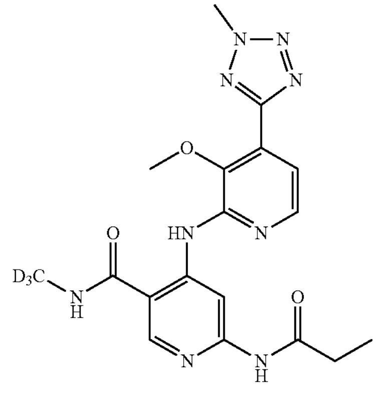 [SMILES: [2H]C([2H])([2H])NC(=O)c1cnc(NC(=O)CC)cc1Nc1nccc(-c2nnn(C)n2)c1OC] | 414 | 415.4 | 0.91 | A |

TABLE 4-continued

| Ex. number | Structure | Mol Wt | LCMS m/z observed | HPLC $t_R$ (min) | HPLC method |
|---|---|---|---|---|---|
| 106 | 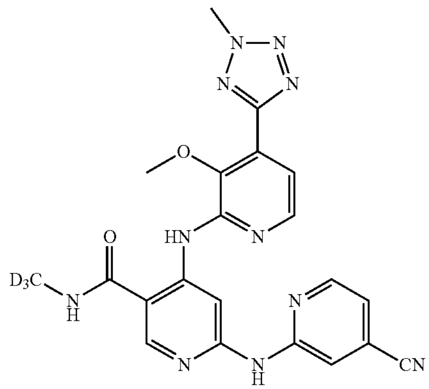 [SMILES: [2H]C([2H])([2H])NC(=O)c1cnc(Nc2cc(C#N)ccn2)cc1Nc1nccc(-c2nnn(C)n2)c1OC] | 460 | 461.4 | 0.96 | A |
| 107 | 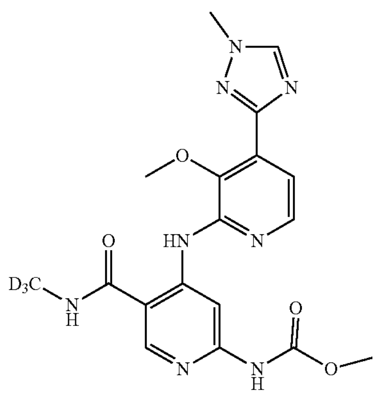 [SMILES: [2H]C([2H])([2H])NC(=O)c1cnc(NC(=O)OC)cc1Nc1nccc(-c2ncn(C)n2)c1OC] | 415 | 416.3 | 0.85 | A |

The Examples in Table 5 were prepared using a similar procedure used to prepare the preceding examples.

TABLE 5

| Ex. number | Structure | Mol Wt | LCMS m/z observed | HPLC $t_R$ (min) | HPLC method |
|---|---|---|---|---|---|
| 108 | 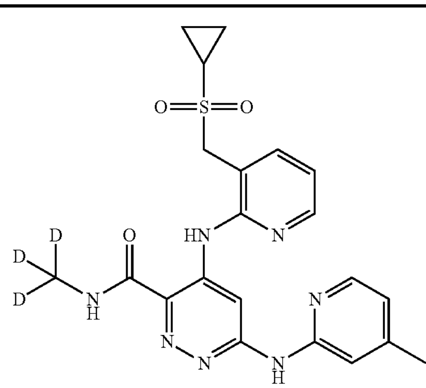 | 456.5 | 457.2 | 1.56 | D |

TABLE 5-continued

| Ex. number | Structure | Mol Wt | LCMS m/z observed | HPLC $t_R$ (min) | HPLC method |
|---|---|---|---|---|---|
| 109 | 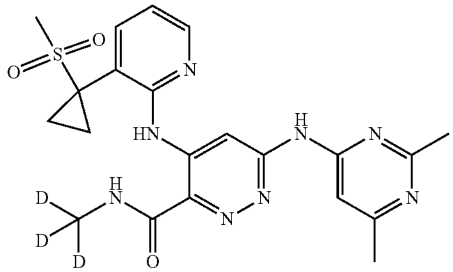 [SMILES: [2H]C([2H])([2H])NC(=O)c1nnc(Nc2cc(C)nc(C)n2)cc1Nc1ncccc1C1(S(C)(=O)=O)CC1] | 471.6 | 472.3 | 0.94 | A |
| 110 | 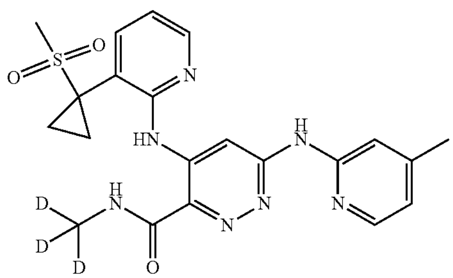 [SMILES: [2H]C([2H])([2H])NC(=O)c1nnc(Nc2cc(C)ccn2)cc1Nc1ncccc1C1(S(C)(=O)=O)CC1] | 456.5 | 457.3 | 1.5 | D |
| 111 | 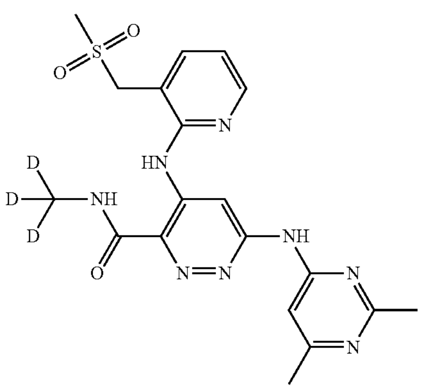 [SMILES: [2H]C([2H])([2H])NC(=O)c1nnc(Nc2cc(C)nc(C)n2)cc1Nc1ncccc1CS(C)(=O)=O] | 445.5 | 446.3 | 1.09 | D |
| 112 | 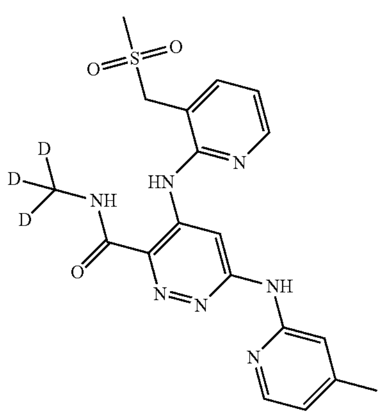 [SMILES: [2H]C([2H])([2H])NC(=O)c1nnc(Nc2cc(C)ccn2)cc1Nc1ncccc1CS(C)(=O)=O] | 430.5 | 431.2 | 0.94 | A |

TABLE 5-continued

| Ex. number | Structure | Mol Wt | LCMS m/z observed | HPLC t_R (min) | HPLC method |
|---|---|---|---|---|---|
| 113 | 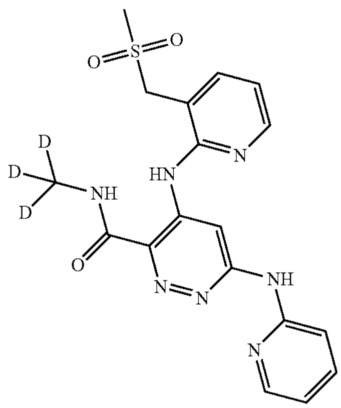 [SMILES: [2H]C([2H])([2H])NC(=O)c1nnc(Nc2ccccn2)cc1Nc1ncccc1CS(C)(=O)=O] | 416.5 | 417.2 | 1.21 | D |
| 114 | 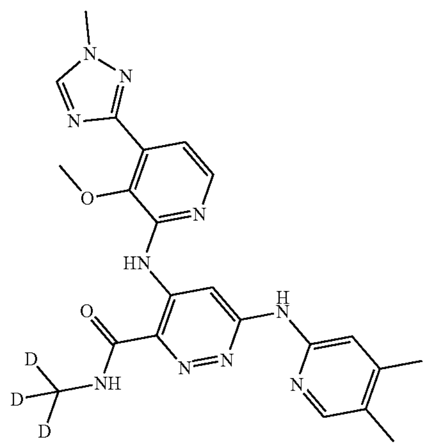 [SMILES: [2H]C([2H])([2H])NC(=O)c1nnc(Nc2cc(C)c(C)cn2)cc1Nc1nccc(-c2ncn(C)n2)c1OC] | 463.5 | 464.3 | 1.16 | A |
| 115 | 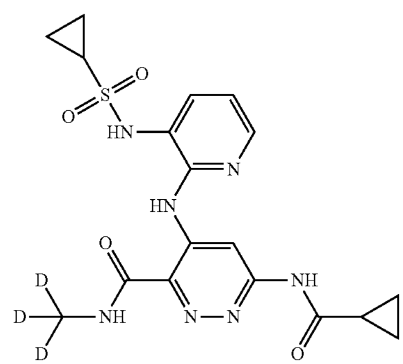 [SMILES: [2H]C([2H])([2H])NC(=O)c1nnc(NC(=O)C2CC2)cc1Nc1ncccc1NS(=O)(=O)C1CC1] | 434.5 | 435.0 | 1.15 | D |
| 116 | 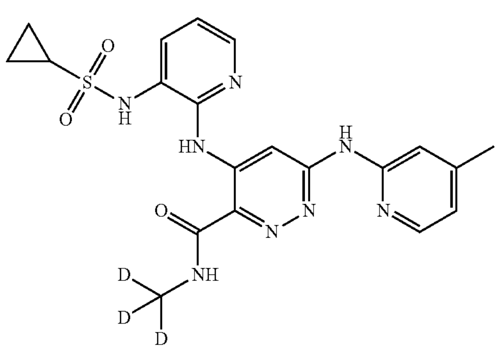 [SMILES: [2H]C([2H])([2H])NC(=O)c1nnc(Nc2cc(C)ccn2)cc1Nc1ncccc1NS(=O)(=O)C1CC1] | 457.5 | 458.0 | 1.42 | D |

TABLE 5-continued
| Ex. number | Structure | Mol Wt | LCMS m/z observed | HPLC $t_R$ (min) | HPLC method |
|---|---|---|---|---|---|
| 117 | 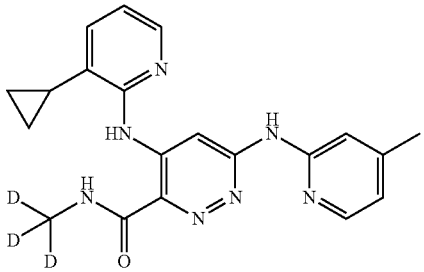 [SMILES: [2H]C([2H])([2H])NC(=O)c1nnc(Nc2cc(C)ccn2)cc1Nc1ncccc1C1CC1] | 378.5 | 379.0 | 1.53 | A |
| 118 | 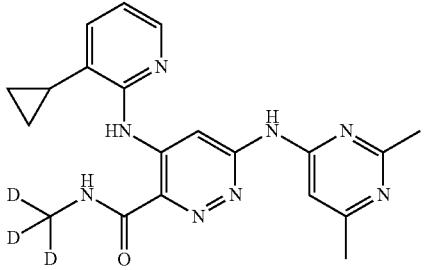 [SMILES: [2H]C([2H])([2H])NC(=O)c1nnc(Nc2cc(C)nc(C)n2)cc1Nc1ncccc1C1CC1] | 393.5 | 394.2 | 1.67 | D |
| 119 | 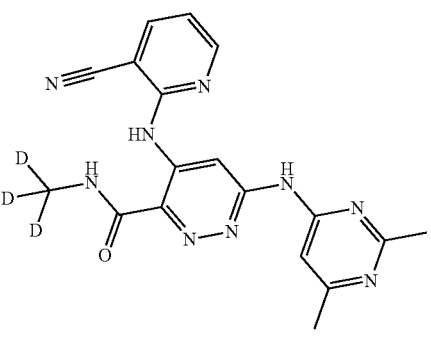 [SMILES: [2H]C([2H])([2H])NC(=O)c1nnc(Nc2cc(C)nc(C)n2)cc1Nc1ncccc1C#N] | 378.4 | 379.3 | 0.98 | A |
| 120 | 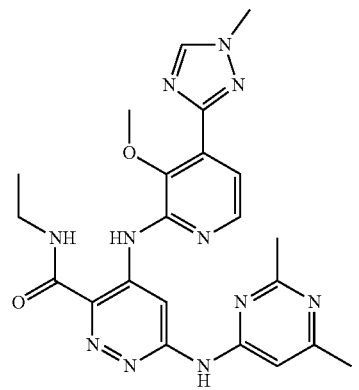 [SMILES: CCNC(=O)c1nnc(Nc2cc(C)nc(C)n2)cc1Nc1nccc(-c2ncn(C)n2)c1OC] | 475.5 | 476.0 | 1.51 | D |
| 121 | 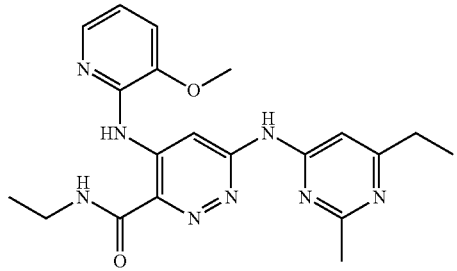 [SMILES: CCNC(=O)c1nnc(Nc2cc(CC)nc(C)n2)cc1Nc1ncccc1OC] | 424.5 | 425.2 | 1.21 | A |

TABLE 5-continued

| Ex. number | Structure | Mol Wt | LCMS m/z observed | HPLC $t_R$ (min) | HPLC method |
|---|---|---|---|---|---|
| 122 | 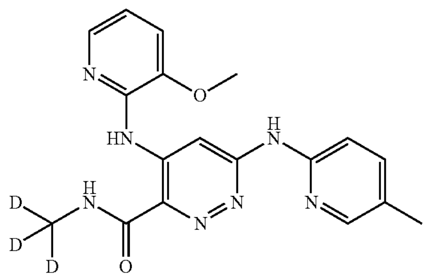 [SMILES: [2H]C([2H])([2H])NC(=O)c1nnc(Nc2ccc(C)cn2)cc1Nc1ncccc1OC] | 368.4 | 369.0 | 1.21 | A |
| 123 | 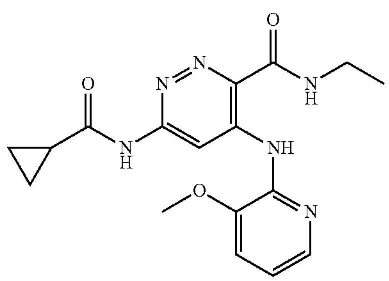 [SMILES: CCNC(=O)c1nnc(NC(=O)C2CC2)cc1Nc1ncccc1OC] | 356.4 | 357.0 | 1.22 | A |
| 124 | 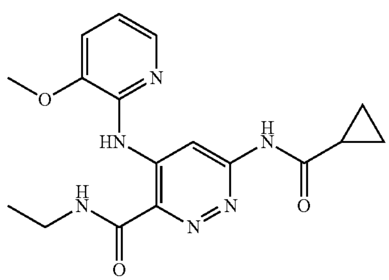 [SMILES: CCNC(=O)c1nnc(NC(=O)C2CC2)cc1Nc1ncccc1OC] | 345.4 | 346.0 | 1.34 | D |
| 125 | 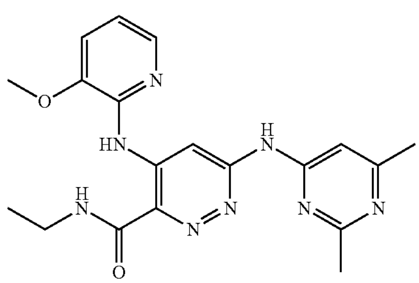 [SMILES: CCNC(=O)c1nnc(Nc2cc(C)nc(C)n2)cc1Nc1ncccc1OC] | 394..4 | 395.0 | 1.51 | D |
| 126 | 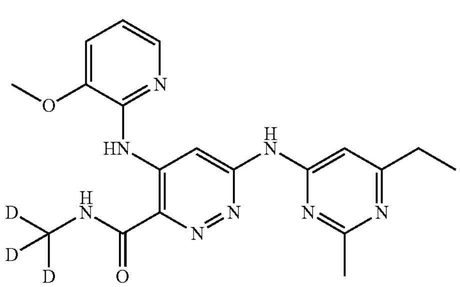 [SMILES: [2H]C([2H])([2H])NC(=O)c1nnc(Nc2cc(CC)nc(C)n2)cc1Nc1ncccc1OC] | 413.5 | 414.0 | 1.42 | D |

TABLE 5-continued

| Ex. number | Structure | Mol Wt | LCMS m/z observed | HPLC $t_R$ (min) | HPLC method |
|---|---|---|---|---|---|
| 127 | 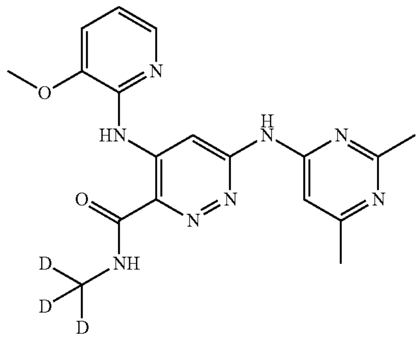 | 383.4 | 384.2 | 1.02 | A |
| 128 | 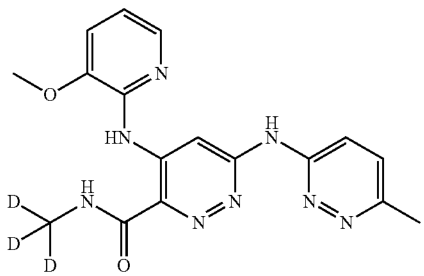 [SMILES: [2H]C([2H])([2H])NC(=O)c1nnc(Nc2ccc(C)nn2)cc1Nc1ncccc1OC] | 369.4 | 370.0 | 1.23 | D |

Biological Assays

The following assay is used to show the activity for compounds of the invention. IFNα-Induced STAT Phosphorylation in Human Whole Blood After an hour long incubation with compound, human whole blood (drawn with either EDTA or ACD-A as anticoagulant) was stimulated with 1000 U/mL recombinant human IFNα A/D (R&D Systems 11200-2) for 15 min. The stimulation was stopped by adding Fix/Lyse buffer (BD 558049). Cells were stained with a CD3 FITC antibody (BD 555916), washed, and permeabilized on ice using Perm III buffer (BD 558050). Cells were then stained with an Alexa-Fluor 647 pSTAT5 (pY694) antibody (BD 612599) for min prior to analysis on the FACS Canto 11. The amount of pSTAT5 expression was quantitated by median fluorescence intensity after gating on the CD3 positive population.

| IFNα-Induced STAT Phosphorylation in Human Whole Blood Inhibition Data | |
|---|---|
| Example No. | LE Human WB IFNα-Induced Stat Phosph. (IC$_{50}$, µM) |
| 1 | 0.01 |
| 2 | 0.05 |
| 3 | 0.07 |
| 4 | ND |
| 5 | 0.13 |
| 6 | 0.03 |
| 7 | 0.11 |
| 8 | 0.05 |
| 9 | 0.17 |
| 10 | 0.04 |
| 11 | 0.02 |
| 12 | 0.13 |
| 13 | >10 |
| 15 | 0.10 |
| 16 | 0.12 |
| 17 | 0.05 |
| 18 | ND |
| 19 | 0.03 |
| 20 | 1.51 |
| 21 | 0.03 |
| 22 | ND |
| 23 | ND |
| 24 | 0.03 |
| 25 | 0.05 |
| 26 | 0.03 |
| 27 | 0.03 |
| 28 | 0.27 |
| 29 | ND |
| 30 | ND |
| 31 | ND |
| 32 | 0.09 |
| 33 | 0.02 |
| 34 | 0.30 |
| 35 | 0.20 |
| 36 | 0.03 |
| 37 | 0.13 |
| 38 | 0.01 |
| 39 | 0.22 |
| 40 | 0.01 |
| 41 | 0.03 |
| 42 | 0.58 |
| 43 | 0.12 |
| 44 | 0.09 |
| 45 | 0.01 |
| 46 | 0.03 |
| 47 | 0.02 |
| 48 | 0.20 |
| 49 | ND |
| 50 | 0.04 |
| 51 | >10 |
| 52 | 0.11 |

IFNα-Induced STAT Phosphorylation in Human Whole Blood Inhibition Data

| Example No. | LE Human WB IFNα-Induced Stat Phosph. (IC$_{50}$, µM) |
| --- | --- |
| 53 | 0.50 |
| 54 | 0.01 |
| 55 | 0.03 |
| 56 | 1.34 |
| 57 | 0.06 |
| 58 | 0.06 |
| 59 | 0.06 |
| 60 | 0.13 |
| 61 | 0.30 |
| 62 | 1.13 |
| 63 | 0.58 |
| 64 | 0.09 |
| 65 | 0.12 |
| 66 | 0.21 |
| 67 | 0.07 |
| 68 | 1.42 |
| 69 | 0.70 |
| 70 | 0.24 |
| 71 | 0.42 |
| 72 | ND |
| 73 | ND |
| 74 | 0.08 |
| 75 | ND |
| 76 | 0.18 |
| 77 | ND |
| 78 | ND |
| 79 | ND |
| 80 | 0.60 |
| 81 | 0.22 |
| 82 | 0.03 |
| 83 | 0.31 |
| 84 | 0.08 |
| 85 | 0.15 |
| 86 | 0.48 |
| 87 | 0.03 |
| 88 | 0.13 |
| 89 | 0.21 |
| 90 | 0.06 |
| 91 | 0.09 |
| 92 | 0.09 |
| 93 | 0.04 |
| 94 | 0.02 |
| 95 | 0.09 |
| 96 | 0.29 |
| 97 | 0.05 |
| 98 | 2.61 |
| 99 | ND |
| 100 | 0.23 |
| 101 | 0.34 |
| 102 | 0.08 |
| 103 | 0.28 |
| 104 | ND |
| 105 | 0.09 |
| 106 | 0.07 |
| 107 | ND |
| 108 | ND |
| 109 | ND |
| 110 | ND |
| 111 | ND |
| 112 | ND |
| 113 | ND |
| 114 | ND |
| 115 | ND |
| 116 | ND |
| 117 | ND |
| 118 | ND |
| 119 | ND |
| 120 | ND |
| 121 | ND |
| 122 | ND |
| 123 | ND |
| 124 | ND |
| 125 | ND |
| 126 | ND |
| 127 | ND |
| 128 | ND |

ND — no data available

We claim:

1. A compound of the formula

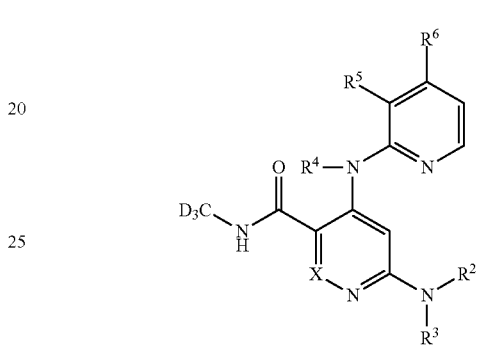

wherein
X is N;
R$^2$ is —C(O)R$^{2a}$; C$_{1-6}$ alkyl, —(CH$_2$)$_r$-3-14 membered carbocycle substituted with 0-1 R$^{2a}$ or a 5-12 membered heterocycle containing 1-4 heteroatoms selected from N, O, and S, substituted with 0-4 R$^{2a}$;
R$^{2a}$ at each occurrence is independently H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, (CH$_2$)$_r$NR$^{11}$R$^{11}$, —(CH$_2$)$_r$C(O)NR$^{11}$R$^{11}$, —(CH$_2$)$_r$NR$^b$C(O) (CH$_2$)$_r$NR$^b$C(O)OR$^c$, —NR$^b$C(O)NR$^{11}$R$^{11}$, —S(O)$_p$NR$^{11}$R$^{11}$, —NR$_b$S(O)$_p$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle containing 1-4 heteroatoms selected from N, O, and S(O)$_p$ substituted with 0-2 R$^a$;
R$^3$ is H, C$_1$-3 alkyl or C$_3$-6 cycloalkyl;
R$^4$ is H, C$_1$-3 alkyl or C$_3$-6 cycloalkyl;
R$^5$ is C$_1$-4 alkyl substituted with 0-1 R$^{5a}$, C$_{1-4}$ alkoxy substituted with 0-1 R$^{5a}$, (CH$_2$)$_r$-phenyl substituted with 0-3R$^{5a}$ or a —(CH$_2$)-5-7 membered heterocycle containing 1-4 heteroatoms selected from N, O, and S(O)$_p$;
R$^{5a}$ is is independently at each occurrence, H, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;
R$^6$ is C$_1$-4 alkyl substituted with 0-1 R$^{6a}$, (CH$_2$)$_r$-phenyl substituted with 0-3 R$^{6a}$ or a —(CH$_2$)-5-7 membered heterocycle containing 1-4 heteroatoms selected from N, O, and S(O)$_p$ substituted with 0-3 R$^{6a}$;
R$^{6a}$ is H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

$R^{11}$ at each occurrence is independently H, $C_{1-4}$ alkyl substituted with 0-3 $R^f$, $CF_3$, $C_{3-10}$ cycloalkyl substituted with 0-1 $R^f$, $(CH)_r$-phenyl substituted with 0-3 $R^d$ or —$(CH_2)_r$-5-7 membered heterocycle containing 1-4 heteroatoms selected from N, O, and $S(O)_p$ substituted with 0-3 $R^d$;

$R^a$ at each occurrence is independently H, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, $(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle or —$(CH_2)_r$-5-7 membered heterocycle containing 1-4 heteroatoms selected from N, O, and $S(O)_p$ substituted with 0-3 $R^f$;

$R^b$ is H, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle containing 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a —$(CH_2)_r$-5-7 membered heterocycle containing 1-4 heteroatoms selected from N, O, and $S(O)_p$;

p is 0, 1, or 2;

r is 0, 1, 2, 3, or 4;

or a stereoisomer or pharmaceutically acceptable salt thereof.

2. The compound according to claim 1 of the formula

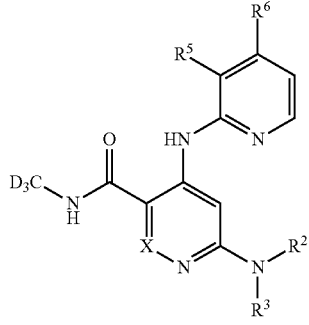

wherein

X is N;

$R^2$ is —$C(O)R^{2a}$; $C_{1-6}$ alkyl, —$(CH_2)_r$-3-14 membered carbocycle substituted with 0-1 $R^{2a}$ or a 5-12 membered heterocycle containing 1-4 heteroatoms selected from N, O, and S, substituted with 0-4 $R^{2a}$;

$R^{2a}$ at each occurrence is independently H, $OCF_3$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_r$ $NR^{11}R^{11}$, —$(CH_2)_rC(O)NR^{11}R^{11}$, —$(CH_2)_rNR^bC(O)R^c$, —$(CH_2)_rNR^bC(O)OR^c$, —$NR^bC(O)NR^{11}R^{11}$, —$S(O)_pNR^{11}R^{11}$, —$NR^bS(O)_pR^c$, —$S(O)_pR^c$, $C_{1-6}$ alkyl substituted with 0-3 $R^a$, $C_{1-6}$ haloalkyl, $C_{2-6}$ alkenyl substituted with 0-3 $R^a$, —$(CH_2)_r$-3-14 membered carbocycle substituted with 0-1 $R^a$ or a —$(CH_2)_r$-5-7 membered heterocycle containing 1-4 heteroatoms selected from N, O, and $S(O)_p$ substituted with 0-2 $R^a$;

$R^3$ is H, $C_{1-3}$ alkyl or $C_{3-6}$ cycloalkyl;

$R^5$ is $C_{1-4}$ alkyl substituted with 0-1 $R^{5a}$, $C_{1-4}$ alkoxy substituted with 0-1 $R^{5a}$, $(CH_2)_r$-phenyl substituted with 0-3 $R^{5a}$ or a —$(CH_2)$-5-7 membered heterocycle containing 1-4 heteroatoms selected from N, O, and $S(O)_p$;

$R^{5a}$ is is independently at each occurrence, H, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl or $(CH_2)_r$-phenyl substituted with 0-3 $R^f$;

$R^6$ is $C_{1-4}$ alkyl substituted with 0-1 $R^{6a}$, $(CH_2)_r$-phenyl substituted with 0-3 $R^{6a}$ or a —$(CH_2)$-5-7 membered heterocycle containing 1-4 heteroatoms selected from N, O, and $S(O)_p$ substituted with 0-3 $R^{6a}$;

$R^{6a}$ is H, $C_{1-4}$ alkyl substituted with 0-3 $R^f$, $CF_3$, $C_{3-10}$ cycloalkyl substituted with 0-1 $R^f$, $(CH)_r$-phenyl substituted with 0-3 $R^d$ or —$(CH_2)_r$-5-7 membered heterocycle containing 1-4 heteroatoms selected from N, O, and $S(O)_p$ substituted with 0-3 $R^d$;

$R^{11}$ at each occurrence is independently H, $C_{1-4}$ alkyl substituted with 0-3 $R^f$, $CF_3$, $C_{3-10}$ cycloalkyl substituted with 0-1 $R^f$, $(CH)_r$-phenyl substituted with 0-3 $R^d$ or —$(CH_2)_r$-5-7 membered heterocycle containing 1-4 heteroatoms selected from N, O, and $S(O)_p$ substituted with 0-3 $R^d$;

$R^a$ at each occurrence is independently H, F, Cl, Br, $OCF_3$, $CF_3$, $CHF_2$, CN, $NO_2$, —$(CH_2)_rOR^b$, —$(CH_2)_rSR^b$, —$(CH_2)_rC(O)R^b$, —$(CH_2)_rC(O)OR^b$, —$(CH_2)_rOC(O)R^b$, —$(CH_2)_rNR^{11}R^{11}$, $(CH_2)_rC(O)NR^{11}R^{11}$, —$(CH_2)_r$ $NR^bC(O)R^c$, —$(CH_2)_rNR^bC(O)OR^c$, —$NR^bC(O)NR^{11}R^{11}$, $S(O)_pNR^{11}R^{11}$, —$NR^bS(O)_pR^c$, —$S(O)R^c$, —$S(O)_2R^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —$(CH_2)_r$-3-14 membered carbocycle or —$(CH_2)_r$-5-7 membered heterocycle containing 1-4 heteroatoms selected from N, O, and $S(O)_p$ substituted with 0-3 $R^f$;

$R^b$ is H, $C_{1-6}$ alkyl substituted with 0-3 $R^d$, $C_{1-6}$ haloalkyl, $C_{3-6}$ cycloalkyl substituted with 0-2 $R^d$, or —$(CH_2)_r$-5-7 membered heterocycle containing 1-4 heteroatoms selected from N, O, and $S(O)_p$ substituted with 0-3 $R^f$ or $(CH_2)_r$-phenyl substituted with 0-3 $R^d$;

$R^c$ is $C_{1-6}$ alkyl substituted with 0-3 $R^f$, $(CH_2)_r$—$C_{3-6}$ cycloalkyl substituted with 0-3 $R^f$ or $(CH_2)_r$-phenyl substituted with 0-3 $R^f$;

$R^d$ is independently at each occurrence, hydrogen, F, Cl, Br, $OCF_3$, $CF_3$, CN, $NO_2$, —$(CH_2)_rC(O)R^c$, —$NR^eR^e$, —$NR^eC(O)OR^c$, $C_{1-6}$ alkyl or $(CH_2)_r$-phenyl substituted with 0-3 $R^f$;

$R^e$ is independently at each occurrence, hydrogen, $C_{1-6}$ alkyl, $C_{3-6}$ cycloalkyl or $(CH_2)_r$-phenyl substituted with 0-3 $R^f$;

$R^f$ is independently at each occurrence, hydrogen, halo, CN, $NH_2$, OH, $C_{3-6}$ cycloalkyl, $CF_3$, $O(C_{1-6}$ alkyl) or a —$(CH_2)_r$-5-7 membered heterocycle containing 1-4 heteroatoms selected from N, O, and $S(O)_p$;

p is 0, 1, or 2;

r is 0, 1, 2, 3, or 4;

or a stereoisomer or pharmaceutically acceptable salt thereof.

3. The compound according to claim 2 of the formula

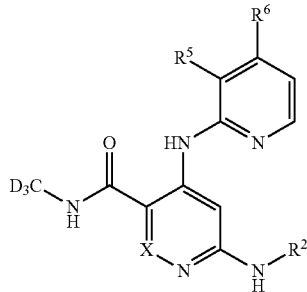

wherein

X is N;

$R^2$ is —C(O)$R^{2a}$; $C_{1-6}$ alkyl, —(CH$_2$)$_r$-3-14 membered carbocycle substituted with 0-1 $R^{2a}$ or a 5-12 membered heterocycle containing 1-4 heteroatoms selected from N, O, and S, substituted with 0-4 $R^{2a}$;

$R^{2a}$ at each occurrence is independently H, OCF$_3$, CN, NO$_2$, —(CH$_2$)$_r$O$R^b$, —(CH$_2$)$_r$S$R^b$, —(CH$_2$)$_r$C(O)$R^b$, —(CH$_2$)$_r$C(O)O$R^b$, —(CH$_2$)$_r$OC(O)$R^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, $C_{1-6}$ alkyl substituted with 0-3 $R^a$, $C_{1-6}$ haloalkyl, $C_{2-6}$ alkenyl substituted with 0-3 $R^a$, —(CH$_2$)$_r$-3-14 membered carbocycle substituted with 0-1 $R^a$ or a —(CH$_2$)$_r$-5-7 membered heterocycle containing 1-4 heteroatoms selected from N, O, and S(O)$_p$ substituted with 0-2 $R^a$;

$R^5$ is $C_{1-4}$ alkyl substituted with 0-1 $R^{5a}$, $C_{1-4}$ alkoxy substituted with 0-1 $R^5$a, (CH$_2$)$_r$-phenyl substituted with 0-3 $R^{5a}$ or a —(CH$_2$)-5-7 membered heterocycle containing 1-4 heteroatoms selected from N, O, and S(O)$_p$;

$R^{5a}$ is is independently at each occurrence, H, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, $C_{1-6}$ alkyl or (CH$_2$)$_r$-phenyl substituted with 0-3 $R^f$;

$R^6$ is $C_{1-4}$ alkyl substituted with 0-1 $R^{6a}$, (CH$_2$)$_r$-phenyl substituted with 0-3 $R^{6a}$ or a —(CH$_2$)$_r$-5-7 membered heterocycle containing 1-4 heteroatoms selected from N, O, and S(O)$_p$ substituted with 0-3 $R^{6a}$;

$R^{6a}$ is H, $C_{1-4}$ alkyl substituted with 0-3 $R^f$, CF$_3$, $C_{3-10}$ cycloalkyl substituted with 0-1 $R^f$, (CH)$_r$-phenyl substituted with 0-3 $R^d$ or —(CH$_2$)$_r$-5-7 membered heterocycle containing 1-4 heteroatoms selected from N, O, and S(O)$_p$ substituted with 0-3 $R^d$;

$R^{11}$ at each occurrence is independently is H, $C_{1-4}$ alkyl substituted with 0-3 $R^f$, CF$_3$, $C_{3-10}$ cycloalkyl substituted with 0-1 $R^f$, (CH)$_r$-phenyl substituted with 0-3 $R^d$ or —(CH$_2$)$_r$-5-7 membered heterocycle containing 1-4 heteroatoms selected from N, O, and S(O)$_p$ substituted with 0-3 $R^d$;

$R^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, (CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, S(O)$_p$NR$^{11}$R$^{11}$, —NR$^b$S(O)$_p$R$^c$, —S(O)R$^c$, —S(O)$_2$R$^c$, $C_{1-6}$ alkyl substituted with 0-3 $R^f$, $C_{1-6}$ haloalkyl, $C_{2-6}$ alkenyl substituted with 0-3 $R^a$, $C_{2-6}$ alkynyl substituted with 0-3 $R^a$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 $R^f$;

$R^b$ is H, $C_{1-6}$ alkyl substituted with 0-3 $R^d$, $C_{1-6}$ haloalkyl, $C_{3-6}$ cycloalkyl substituted with 0-2 $R^d$, or —(CH$_2$)$_r$-5-7 membered heterocycle containing 1-4 heteroatoms selected from N, O, and S(O)$_p$ substituted with 0-3 $R^f$ or (CH$_2$)$_r$-phenyl substituted with 0-3 $R^d$;

$R^c$ is $C_{1-6}$ alkyl substituted with 0-3 $R^f$, (CH$_2$)$_r$—$C_{3-6}$ cycloalkyl substituted with 0-3 $R^f$ or (CH$_2$)$_r$-phenyl substituted with 0-3 $R^f$;

$R^d$ is independently at each occurrence, hydrogen, F, Cl, Br, OCF$_3$, CF$_3$, CN, NO$_2$, —(CH$_2$)$_r$C(O)R$^c$, —NR$^e$R$^e$, —NR$^e$C(O)OR$^c$, $C_{1-6}$ alkyl or (CH$_2$)$_r$-phenyl substituted with 0-3 $R^f$;

$R^e$ is independently at each occurrence, hydrogen, $C_{1-6}$ alkyl, $C_{3-6}$ cycloalkyl or (CH$_2$)$_r$-phenyl substituted with 0-3 $R^f$;

$R^f$ is independently at each occurrence, hydrogen, halo, CN, NH$_2$, OH, $C_{3-6}$ cycloalkyl, CF$_3$, O($C_{1-6}$ alkyl) or a —(CH$_2$)$_r$-5-7 membered heterocycle containing 1-4 heteroatoms selected from N, O, and S(O)$_p$;

p is 0, 1, or 2;

r is 0, 1, 2, 3, or 4;

or a stereoisomer or pharmaceutically acceptable salt thereof.

4. The compound according to claim 3 of the formula

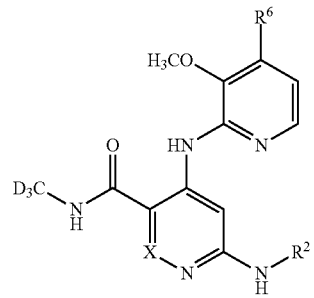

wherein

X is N;

$R^2$ is —C(O)$R^{2a}$; $C_{1-6}$ alkyl, —(CH$_2$)$_r$-3-14 membered carbocycle substituted with 0-1 $R^{2a}$ or a 5-12 membered heterocycle containing 1-4 heteroatoms selected from N, O, and S, substituted with 0-4 $R^{2a}$;

$R^{2a}$ at each occurrence is independently H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, $C_{1-6}$ alkyl substituted with 0-3 $R^a$, $C_{1-6}$ haloalkyl, $C_{2-6}$ alkenyl substituted with 0-3 $R^a$, —(CH$_2$)$_r$-3-14 membered carbocycle substituted with 0-1 $R^a$ or a —(CH$_2$)$_r$-5-7 membered heterocycle containing 1-4 heteroatoms selected from N, O, and S(O)$_p$ substituted with 0-2 $R^a$;

$R^3$ is H, $C_{1-3}$ alkyl or $C_{3-6}$ cycloalkyl;

$R^5$ is $C_{1-4}$ alkyl substituted with 0-1 $R^{5a}$, $C_1$-4 alkoxy substituted with 0-1 $R^{5a}$, (CH$_2$)$_r$-phenyl substituted with 0-3 $R^{5a}$ or a —(CH$_2$)-5-7 membered heterocycle containing 1-4 heteroatoms selected from N, O, and S(O)$_p$;

R$^{5a}$ is is independently at each occurrence, H, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^6$ is C$_{1-4}$ alkyl substituted with 0-1 R$^{6a}$, (CH$_2$)$_r$-phenyl substituted with 0-3 R$^{6a}$ or a —(CH$_2$)-5-7 membered heterocycle containing 1-4 heteroatoms selected from N, O, and S(O)$_p$ substituted with 0-3 R$^{6a}$;

R$^{6a}$ is H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^{11}$ at each occurrence is independently H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, (CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle containing 1-4 heteroatoms selected from N, O, and S(O)$_p$ substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —(CH$_2$)$_r$C(O)R$^c$, —NR$^e$R$^e$, —NR$^e$C(O)OR$^c$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle containing 1-4 heteroatoms selected from N, O, and S(O)$_p$;

p is 0, 1, or 2;

r is 0, 1, 2, 3, or 4;

or a stereoisomer or pharmaceutically acceptable salt thereof.

5. The compound according to claim 4 of the formula

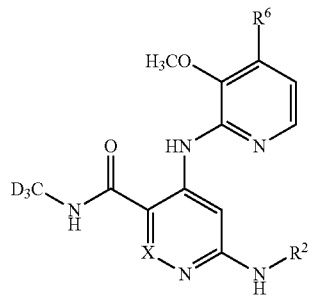

wherein

R$^2$ is —C(O)R$^{2a}$; C$_{1-6}$ alkyl, —(CH$_2$)$_r$-3-14 membered carbocycle substituted with 0-1 R$^{2a}$ or a 5-12 membered heterocycle containing 1-4 heteroatoms selected from N, O, and S, substituted with 0-4 R$^2$a;

R$^{2a}$ at each occurrence is independently H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^d$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle containing 1-4 heteroatoms selected from N, O, and S(O)$_p$ substituted with 0-2 R$^a$;

R$^6$ is C$_{1-4}$ alkyl substituted with 0-1 R$^{6a}$, (CH$_2$)$_r$-phenyl substituted with 0-3 R$^{6a}$ or a —(CH$_2$)-5-7 membered heterocycle containing 1-4 heteroatoms selected from N, O, and R$^{6a}$ is H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^{11}$ at each occurrence is independently H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle containing 1-4 heteroatoms selected from N, O, and S(O)$_p$ substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —OR$^e$, —(CH$_2$)$_r$C(O)R$^e$, —NR$^e$R$^e$, —NR$^e$C(O)OR$^e$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle containing 1-4 heteroatoms selected from N, O, and S(O)$_p$;

p is 0, 1, or 2;

r is 0, 1, 2, 3, or 4;

or a stereoisomer or pharmaceutically acceptable salt thereof.

6. The compound according to claim 5 of the formula

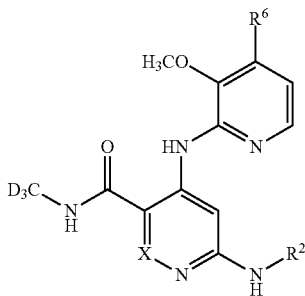

wherein

R$^2$ is —C(O)R$^{2a}$; C$_{1-6}$ alkyl, —(CH$_2$)$_r$-3-14 membered carbocycle substituted with 0-1 R$^{2a}$ or a 5-12 membered heterocycle containing 1-4 heteroatoms selected from N, O, and S, substituted with 0-4 R$^{2a}$;

R$^{2a}$ at each occurrence is independently H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(o)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^d$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle containing 1-4 heteroatoms selected from N, O, and S(O)$_p$ substituted with 0-2 R$^a$;

R$^6$ is C$_{1-4}$ alkyl substituted with 0-1 R$^{6a}$, (CH$_2$)$_r$-phenyl substituted with 0-3 R$^{6a}$ or a —(CH$_2$)-5-7 membered heterocycle containing 1-4 heteroatoms selected from N, O, and S(O)$_p$ substituted with 0-3 R$^{6a}$;

R$^{6a}$ is H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^{11}$ at each occurrence is independently H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^a$ at each occurrence is independently H, F, C$_1$, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)R$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle containing 1-4 heteroatoms selected from N, O, and S(O)$_p$ substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —OR$^e$, —(CH$_2$)$_r$C(O)R$^c$, —NR$^e$R$^e$, —NR$^e$C(O)OR$^e$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle containing 1-4 heteroatoms selected from N, O, and S(O)$_p$;

p is 0, 1, or 2;

r is 0, 1, 2 or 3;

or a stereoisomer or pharmaceutically acceptable salt thereof.

7. The compound according to claim 6 of the formula

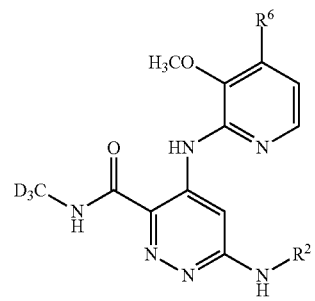

wherein

R$^2$ is —C(O)R$^{2a}$ or a 5-12 membered heterocycle containing 1-4 heteroatoms selected from N, O, and S, substituted with 0-4 R$^{2a}$;

R$^{2a}$ at each occurrence is independently H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^e$, —NR$^b$C(O)NR$^{11}$R$^{11}$, —S(O)$_p$NR$^{11}$R$^{11}$), —NR$^b$S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle containing 1-4 heteroatoms selected from N, O, and S(O)$_p$ substituted with 0-2 R$^a$;

R$^6$ is C$_{1-4}$ alkyl substituted with 0-1 R$^{6a}$, (CH$_2$)$_r$-phenyl substituted with 0-3 R$^{6a}$ or a —(CH$_2$)-5-7 membered heterocycle containing 1-4 heteroatoms selected from N, O, and S(O)$_p$ substituted with 0-3 R$^{6a}$;

R$^{6a}$ is H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^{11}$ at each occurrence is independently H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle containing 1-4 heteroatoms selected from N, O, and S(O)$_p$ substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —(CH$_2$)$_r$C(O)R$^e$, —NR$^e$R$^e$, —NR$^e$C(O)OR$^e$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle containing 1-4 heteroatoms selected from N, O, and S(O)$_p$;

p is 0, 1, or 2;

r is 0, 1, 2 or 3;

or a stereoisomer or pharmaceutically acceptable salt thereof.

8. The compound according to claim 7 of the formula

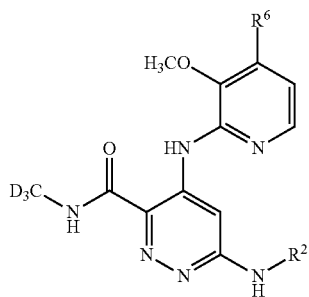

wherein

R$^2$ is —C(O)R$^{2a}$ or a 5-12 membered heterocycle containing 1-4 heteroatoms selected from N, O, and S, substituted with 0-4 R$^{2a}$;

R$^{2a}$ at each occurrence is independently H, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)$_p$R$^c$, C$_{1-6}$ alkyl substituted with 0-3 R$^a$, C$_{1-6}$ haloalkyl, C$_{2-6}$ alkenyl substituted with 0-3 R$^a$, —(CH$_2$)$_r$-3-14 membered carbocycle substituted with 0-1 R$^a$ or a —(CH$_2$)$_r$-5-7 membered heterocycle containing 1-4 heteroatoms selected from N, O, and S(O)$_p$ substituted with 0-2 R$^a$;

R$^6$ is a —(CH$_2$)-5-7 membered heterocycle containing 1-4 heteroatoms selected from N, O, and S(O)$_p$ substituted with 0-3 R$^{6a}$;

R$^{6a}$ is H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^{11}$ at each occurrence is independently H, C$_{1-4}$ alkyl substituted with 0-3 R$^f$, CF$_3$, C$_{3-10}$ cycloalkyl substituted with 0-1 R$^f$, (CH)$_r$-phenyl substituted with 0-3 R$^d$ or —(CH$_2$)$_r$-5-7 membered heterocycle containing 1-4 heteroatoms selected from N, O, and S(O)$_p$ substituted with 0-3 R$^d$;

R$^a$ at each occurrence is independently H, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-3 R$^f$, C$_{1-6}$ haloalkyl, C$_{2-6}$ alkenyl substituted with 0-3 R$^a$, C$_{2-6}$ alkynyl substituted with 0-3 R$^a$, —(CH$_2$)$_r$-3-14 membered carbocycle or —(CH$_2$)$_r$-5-7 membered heterocycle containing 1-4 heteroatoms selected from N, O, and S(O)$_p$ substituted with 0-3 R$^f$;

R$^b$ is H, C$_{1-6}$ alkyl substituted with 0-3 R$^d$, C$_{1-6}$ haloalkyl, C$_{3-6}$ cycloalkyl substituted with 0-2 R$^d$, or —(CH$_2$)$_r$-5-7 membered heterocycle containing 1-4 heteroatoms selected from N, O, and S(O)$_p$ substituted with 0-3 R$^f$ or (CH$_2$)$_r$-phenyl substituted with 0-3 R$^d$;

R$^c$ is C$_{1-6}$ alkyl substituted with 0-3 R$^f$, (CH$_2$)$_r$—C$_{3-6}$ cycloalkyl substituted with 0-3 R$^f$ or (CH$_2$)$_r$-phenyl substituted with 0-3 R$^f$;

R$^d$ is independently at each occurrence, hydrogen, F, Cl, Br, OCF$_3$, CF$_3$, CN, NO$_2$, —OR$^e$, —(CH$_2$)$_r$C(O)R$^e$, —NR$^e$R$^e$, —NR$^e$C(O)OR$^e$, C$_{1-6}$ alkyl or (CH$_2$)$_r$-phenyl substituted with 0-3 R$^f$;

R$^e$ is independently at each occurrence, hydrogen, C$_{1-6}$ alkyl, C$_{3-6}$ cycloalkyl or (CH$_2$)$_r$-phenyl substituted with 0-3 R$^f$;

R$^f$ is independently at each occurrence, hydrogen, halo, CN, NH$_2$, OH, C$_{3-6}$ cycloalkyl, CF$_3$, O(C$_{1-6}$ alkyl) or a —(CH$_2$)$_r$-5-7 membered heterocycle containing 1-4 heteroatoms selected from N, O, and S(O)$_p$;

p is 0, 1, or 2;

r is 0, 1, 2 or 3;

or a stereoisomer or pharmaceutically acceptable salt thereof.

9. A compound which is 6-cyclopropaneamido-4-{[3-methoxy-4-(1-methyl-1H-1,2,4-triazol-3-yl)pyridin-2-yl] amino}—N-($^2$H$_3$)methylpyridazine-3-carboxamide, 4-{[3-methoxy-4-(1-methyl-1H-1,2,4-triazol-3-yl)pyridin-2-yl]amino}-N-($^2$H$_3$)methyl-6-[(pyridin-2-yl) amino]pyridazine-3-carboxamide, 6-cyclobutaneamido-4-{[3-methoxy-4-(1-methyl-1H-1,2,4-triazol-3-yl)pyridin-2-yl]amino}-N-($^2$H$_3$)methylpyridazine-3-carboxamide, 4-{[3-methoxy-4-(1-methyl-1H-1,2,4-triazol-3-yl)pyridin-2-yl]amino}-N-($^2$H$_3$)methyl-6]2-(morpholin-4-yl)acetamido]pyridazine-3-carboxamide, 6-acetamido-4-{[3-methoxy-4-(1-methyl-1H-1,2,4-triazol-3-yl)pyridin-2-yl]amino}-N-($^2$H$_3$)methylpyridazine-3-carboxamide, 6-[(5-fluoropyridin-2-yl)amino]-4-{[3-methoxy-4-(1-methyl-1H-1,2,4-triazol-3-yl)pyridin-2-yl] amino}—N-($^2$H$_3$)methylpyridazine-3-carboxamide, 6-butanamido-4-{[3-methoxy-4-(1-methyl-1H-1,2,4-triazol-3-yl)pyridin-2-yl]amino}-N-($^2$H$_3$)methylpyridazine-3-carboxamide, 4-{[3-methoxy-4-(1-methyl-1H-1,2,4-triazol-3-yl)pyridin-2-yl]amino}-N-($^2$H$_3$)methyl-6-propanamidopyridazine-3-carboxamide, methyl N-(5-{[3-methoxy-4-(1-methyl-1H-1,2,4-triazol-3-yl)pyridin-2-yl] amino}-6-[($^2$H$_3$)methylcarbamoyl]pyridazin-3-yl)carbamate, 6-(2-cyclopropylacetamido)-4-{[3-methoxy-4-(1-methyl-1H-1,2,4-triazol-3-yl)pyridin-2-yl] amino}—N-($^2$H$_3$)methylpyridazine-3-carboxamide, 4-{[3-methoxy-4-(1-methyl-1H-1,2,4-triazol-3-yl)pyridin-2-yl]amino}-N-($^2$H$_3$)methyl-6-[(4-methylpyridin-2-yl)amino]pyridazine-3-carboxamide, 4-{[3-methoxy-4-(1-methyl-1H-1,2,4-triazol-3-yl)pyridin-2-yl]amino}-6-[(4-methoxypyridin-2-yl)amino]-N-($^2$H$_3$)methylpyridazine-3-carboxamide, 6-[(4-cyanopyridin-2-yl)amino]-4-{[3-methoxy-4-(1-methyl-1H-1,2,4-triazol-3-yl)pyridin-2-yl] amino}-N-($^2$H$_3$)methylpyridazine-3-carboxamide, 6-[(5-fluoropyridin-2-yl)amino]-4-{[3-methoxy-4-(1-methyl-1H-1,2,4-triazol-3-yl)pyridin-2-yl] amino}-N-($^2$H$_3$)methylpyridazine-3-carboxamide, 6-[(4,5-dimethylpyridin-2-yl)amino]-4-{[3-methoxy-4-(1-methyl-1H-1,2,4-triazol-3-yl)pyridin-2-yl] amino}-N-($^2$H$_3$)methylpyridazine-3-carboxamide, 6-[(5-fluoro-4-methylpyridin-2-yl)amino]-4-{[3-methoxy-4-(1-methyl-1H-1,2,4-triazol-3-yl)pyridin-2-yl] amino}-N-($^2$H$_3$)methylpyridazine-3-carboxamide, 6-[(4-ethylpyridin-2-yl)amino]-4-{[3-methoxy-4-(1-methyl-1H-1,2,4-triazol-3-yl)pyridin-2-yl] amino}-N-($^2$H$_3$)methylpyridazine-3-carboxamide, 4-{[3-methoxy-4-(1-methyl-1H-1,2,4-triazol-3-yl)pyridin-2-yl]amino}-N-($^2$H$_3$)methyl-6-{[5-(2-oxopyrrolidin-1-yl)pyridin-2-yl]amino} pyridazine-3-carboxamide, 6-[(4-fluoropyridin-2-yl)amino]-4-{[3-methoxy-4-(1-methyl-1H-1,2,4-triazol-3-yl)pyridin-2-yl] amino}-N-($^2$H$_3$)methylpyridazine-3-carboxamide, 4-{[3-methoxy-4-(1-methyl-1H-1,2,4-triazol-3-yl)pyridin-2-yl]amino}-N-($^2$H$_3$)methyl-6-[(5-methyl-1,3,4-thiadiazol-2-yl)amino]pyridazine-3-carboxamide, 6-[(4-chloropyridin-2-yl)amino]-4-{[3-methoxy-4-(1-methyl-1H-1,2,4-triazol-3-yl)pyridin-2-yl] amino}-N-($^2$H$_3$)methylpyridazine-3-carboxamide, 6-[(5-chloro-4-methylpyridin-2-yl)amino]-4-{[3-methoxy-4-(1-methyl-1H-1,2,4-triazol-3-yl)pyridin-2-yl] amino}-N-($^2$H$_3$)methylpyridazine-3-carboxamide, 6-[(4-chloro-5-methylpyridin-2-yl)amino]-4-{[3-methoxy-4-(1-methyl-1H-1,2,4-triazol-3-yl)pyridin-2-yl] amino}-N-($^2$H$_3$)methylpyridazine-3-carboxamide, 4-{[3-methoxy-4-(1-methyl-1H-1,2,4-triazol-3-yl)pyridin-2-yl]amino}-N-($^2$H$_3$)methyl-6-({2-oxo-2H-[1,3'-bipyridine]-6'-yl} amino)pyridazine-3-carboxamide, 6-{[4-(2-hydroxypropan-2-yl)pyridin-2-yl] amino}-4-{[3-methoxy-4-(1-methyl-1H-1,2,4-triazol-3-yl)pyridin-2-yl] amino}-N-($^2$H$_3$)methylpyridazine-3-carboxamide, 4-{[3-methoxy-4-(1-methyl-1H-1,2,4-triazol-3-yl)pyridin-2-yl]amino}-N-($^2$H$_3$)methyl-6-{[2-oxo-3-(trifluoromethyl)-2H41,3 '-bipyridine]-6'-yl} amino 1 pyridazine-3-carboxamide, 4-{[3-methoxy-4-(1-methyl-1H-1,2,4-triazol-3-yl)pyridin-2-yl]amino}-6-[(6-methoxypyridin-2-yl)amino]-N-($^2$H$_3$)methylpyridazine-3-carboxamide, 4-{[3-methoxy-4-(1-methyl-1H-1,2,4-triazol-3-yl)pyridin-2-yl]amino}-N-($^2$H$_3$)methyl-6-(phenylamino)pyridazine-3-carboxamide, 6-[(4-acetylpyridin-2-yl)amino]-4-{[3-methoxy-4-(1-methyl-1H-1,2,4-triazol-3-yl)pyridin-2-yl] amino 1-N-($^2$H$_3$)methylpyridazine-3-carboxamide, 6-({5-chloro-2-oxo-2H-[1,3'-bipyridine]-6'-yl}amino)-4-{[3-methoxy-4-(1-methyl-1H-1,2,4-triazol-3-yl)pyridin-2-yl] amino 1-N-($^2$H$_3$)methylpyridazine-3-carboxamide, 4-{[3-methoxy-4-(1-methyl-1H-1,2,4-triazol-3-yl)pyridin-2-yl]amino}-N-($^2$H$_3$)methyl-6-({[1,3]thiazolo[5,4-b]pyridin-5-yl}amino)pyridazine-3-carboxamide, 4-{[3-methoxy-4-(1-methyl-1H-1,2,4-triazol-3-yl)pyridin-2-yl]amino}-N-($^2$H$_3$)methyl-6-{[4-(trifluoromethyl)pyridin-2-yl]amino}pyridazine-3-carboxamide, 6-{[5-(2-hydroxypropan-2-yl)pyridin-2-yl] amino}-4-{[3-methoxy-4-(1-methyl-1H-1,2,4-triazol-3-yl)pyridin-2-yl] amino 1-N-($^2$H$_3$)methylpyridazine-3-carboxamide, 6-[(4-fluorophenyl)amino]-4-{[3-methoxy-4-(1-methyl-1H-1,2,4-triazol-3-yl)pyridin-2-yl] amino 1-N-($^2$H$_3$)methylpyridazine-3-carboxamide, 4-{[3-methoxy-4-(1-methyl-1H-1,2,4-triazol-3-yl)pyridin-2-yl]amino}-N-($^2$H$_3$)methyl-6-[(pyridin-4-yl)amino]pyridazine-3-carboxamide, 6-[(6-ethoxypyridazin-3-yl)amino]-4-{[3-methoxy-4-(1-methyl-1H-1,2,4-triazol-3-yl)pyridin-2-yl] amino 1-N-($^2$H$_3$)methylpyridazine-3-carboxamide, 6-{[5-[3-tert-butyl-2-oxoimidazolidin-1-yl)pyridin-2-yl]amino}-4-{[3-methoxy-4-(1-methyl-1H-1,2,4-triazol-3-yl)pyridin-2-yl]amino 1-N-($^2$H$_3$)methylpyridazine-3-carb oxamide, 4-{[3-methoxy-4-(1-methyl-1H-1,2,4-triazol-3-yl)pyridin-2-yl]amino}-N-($^2$H$_3$)methyl-6-{[5-(morpholin-4-yl)pyridin-2-yl]amino}pyridazine-3-carboxamide, 6-[(4,5-difluoropyridin-2-yl)amino]-4-{[3-methoxy-4-(1-methyl-1H-1,2,4-triazol-3-yl)pyridin-2-yl] amino 1-N-($^2$H$_3$)methylpyridazine-3-carboxamide, 4-{[3-methoxy-4-(1-methyl-1H-1,2,4-triazol-3-yl)pyridin-2-yl]amino}-N-($^2$H$_3$)methyl-6-[(6-methylpyridin-2-yl)amino]pyridazine-3-carboxamide, 6-cyclopropaneamido-4-({3-methoxy-4-[5-(methoxymethyl)-1,2,4-oxadiazol-3-yl]pyridin-2-yl} amino)-N-($^2$H$_3$)methylpyridazine-3-carboxamide, 4-[(4-cyano-3-methoxypyridin-2-yl)amino]-6-cyclopropaneamido-N-($^2$H$_3$)methylpyridazine-3-carboxamide, methyl N-{5-[(3-methoxy-4-{5-[(N-methylmethanesulfonamido)methyl]-1,2,4-oxadiazol-3-yl}pyridin-2-yl)amino]-6-[($^2$H$_3$)methylcarbamoyl]pyridazin-3-yl} carbamate, methyl N-{5-[(3-methoxy-4-{5-[(morpholin-4-yl)methyl]-1,2,4-oxadiazol-3-yl}pyridin-2-yl)amino]-6-[($^2$H$_3$)methylcarbamoyl]pyridazin-3-yl} carbamate, 6-cyclopropaneamido-4-[(3-methoxy-4-{5-[(N-methyl-methanesulfonamido)methyl]-1,2,4-oxadiazol-3-yl}pyridin-2-yl)amino]-N-($^2$H$_3$)methylpyridazine-3-carboxamide, 6-cyclopropaneamido-4-[(3-methoxy-4-{5-[(morpholin-4-yl)methyl]-1,2,4-oxadiazol-3-yl}pyridin-2-yl)amino]-N-($^2$H$_3$)methylpyridazine-3-carboxamide, methyl N-(5-{[3-methoxy-4-(5-methyl-1,2,4-oxadiazol-3-yl)pyridin-2-yl]amino}-6-[($^2$H$_3$)methylcarbamoyl]pyridazin-3-yl)carbamate, 6-cyclopropaneamido-4[(4-{5-[(1 S)-1-hydroxyethyl]-1,2,4-oxadiazol-3-yl}-3-methoxypyridin-2-yl)amino]-N-($^2$H$_3$)methylpyridazine-3-carboxamide, 6-cyclopropaneamido-4-[(4-{5-[(dimethylamino) methyl]-1,2,4-oxadiazol-3-yl}-3-methoxypyridin-2-yl)amino]-N-($^2$H$_3$)methylpyridazine-3-carboxamide, 6-cyclopropaneamido-4-[(3-methoxy-4-{5-[(methyl-amino)methyl]-1,2,4-oxadiazol-3-yl}pyridin-2-yl)amino]-N-($^2$H$_3$)methylpyridazine-3-carboxamide, 4-({4-[5-(cyanomethyl)-1,2,4-oxadiazol-3-yl]-3-methoxypyridin-2-yl} amino)-6-cyclopropaneamido-N-($^2$H$_3$)methylpyridazine-3-carboxamide, 60

4-[(3-methoxy-4-{5-[(N-methylmethanesulfonamido) methyl]-1,2,4-oxadiazol-3-yl}pyridin-2-yl)amino]-N-($^2$H$_3$)methyl-6-[(4-methylpyridin-2-yl)amino] pyridazine-3-carboxamide, 4-({3-methoxy-4-[5-(methoxymethyl)-1,2,4-oxadiazol-3-yl]pyridin-2-yl} amino)-N-($^2$H$_3$)methyl-6-[(4-methylpyridin-2-yl)amino]pyridazine-3-carboxamide, 4-((3-methoxy-4-(5-(morpholinomethyl)-1,2,4-oxadi-azol-3-yl)pyridin-2-yl)amino)-N-(methyl-d3)-6-(4-methylpyridin-2-yl)amino)pyridazine-3-carboxamide, methyl N-{5-[(44 5-[(1,1-dioxo-1λ$^6$,2-thiazinan-2-yl) methyl]-1,2,4-oxadiazol-3-yl}-3-methoxypyridin-2-yl) amino]-6-[($^2$H$_3$)methylcarbamoyl]pyridazin-3-yl} carbamate, 4-[(3-methoxy-4-{5-[(morpholin-4-yl)methyl]-1,2,4-oxa-diazol-3-yl} pyridin-2-yl)amino]-N-($^2$H$_3$)methyl-6-propanamidopyridazine-3-carboxamide, 4-({3-methoxy-4-[5-(methoxymethyl)-1,2,4-oxadiazol-3-yl]pyridin-2-yl} amino)-N-($^2$H$_3$)methyl-6-propanamidopyridazine-3-carboxamide, 6-(2-cyclopropylacetamido)-4-[(3-methoxy-4-{5-[(N-methylmethanesulfonamido)methyl]-1,2,4-oxadiazol-3-yl}pyridin-2-yl)amino]-N-($^2$H$_3$)methylpyridazine-3-carboxamide, 4-({3-methoxy-4-[5-(methoxymethyl)-1,2,4-oxadiazol-3-yl]pyridin-2-yl} amino)-N-($^2$H$_3$)methyl-6-(3-methylbutanamido)pyridazine-3-carboxamide, 4-[(3-methoxy-4-{5-[(morpholin-4-yl)methyl]-1,2,4-oxadiazol-3-yl} pyridin-2-yl)amino]-N-($^2$H$_3$)methyl-6-(3-methylbutanamido)pyridazine-3-carboxamide, 4-((3-methoxy-4-{5-[(N-methylmethanesulfonamido) methyl]-1,2,4-oxadiazol-3-yl}pyridin-2-yl)amino]-N-($^2$H$_3$)methyl-6-(3-methylbutanamido)pyridazine-3-carboxamide, 4-[(3-methoxy-4-{5-[(2-oxo-1,3-oxazolidin-3-yl) methyl]-1,2,4-oxadiazol-3-yl}pyridin-2-yl)amino]-N-($^2$H$_3$)methyl-6-(3-methylbutanamido)pyridazine-3-carboxamide, 6-(2-cyclopropylacetamido)-4-({3-methoxy-4-[5-(methoxymethyl)-1,2,4-oxadiazol-3-yl]pyridin-2-yl} amino)-N-($^2$H$_3$)methylpyridazine-3-carboxamide, 6-(2-cyclopropylacetamido)-4-({4-[5-(hydroxymethyl)-1,2,4-oxadiazol-3-yl]-3-methoxypyridin-2-yl} amino)-N-($^2$H$_3$)methylpyridazine-3-carboxamide, 6-cyclopropaneamido-4-{[3-methoxy-4-(5-methyl-1,2,4-oxadiazol-3-yl)pyridin-2-yl]amino}-N-($^2$H$_3$)methylpyridazine-3-carboxamide 74

6-(2-cyclopropylacetamido)-4-{[3-methoxy-4-(5-methyl-1,2,4-oxadiazol-3-yl)pyridin-2-yl] amino}-N-(2H$_3$) methylpyridazine-3-carboxamide, 4-({3-methoxy-4-[5-(methoxymethyl)-1,2,4-oxadiazol-3-yl]pyridin-2-yl} amino)-N-($^2$H$_3$)methyl-6-[2-(oxetan-3-yl)acetamido]pyridazine-3-carboxamide, 6-[(5-chloro-4-methylpyridin-2-yl)amino]-4-{[3-methoxy-4-(5-methyl-1,2,4-oxadiazol-3-yl)pyridin-2-yl] amino}-N-($^2$H$_3$)methylpyridazine-3-carboxamide, 4-[3-methoxy-4-(5-methyl-1,2,4-oxadiazol-3-yl)pyridin-2-yl]amino}-N-($^2$H$_3$)methyl-6-[(4-methylpyridin-2-yl)amino]pyridazine-3-carboxamide, 4-[3-methoxy-4-(5-methyl-1,2,4-oxadiazol-3-yl)pyridin-2-yl]amino}-N-($^2$H$_3$)methyl-6-[(6-methylpyrimidin-4-yl)amino]pyridazine-3-carboxamide, 6-[4-(2-hydroxypropan-2-yl)pyridin-2-yl] amino}-4-{[3-methoxy-4-(5-methyl-1,2,4-oxadiazol-3-yl)pyridin-2-yl] amino}-N-($^2$H$_3$)methylpyridazine-3-carboxamide, 4-[3-methoxy-4-(5-methyl-1,2,4-oxadiazol-3-yl)pyridin-2-yl]amino}-N-($^2$H$_3$)methyl-6-propanamidopyridazine-3-carboxamide, 6-[5-(2-hydroxypropan-2-yl)pyridin-2-yl] amino}-4-{[3-methoxy-4-(5-methyl-1,2,4-oxadiazol-3-yl)pyridin-2-yl] amino}-N-($^2$H$_3$)methylpyridazine-3-carboxamide 6-cyclopropaneamido-4-({4-[5-(dimethylcarbamoyl) pyrazin-2-yl]-3-methoxypyridin-2-yl} amino)-N-($^2$H$_3$) methylpyridazine-3-carboxamide, 6-cyclopropaneamido-4-[(4-{5-[ethyl(methyl)carbamoyl]pyrazin-2-yl}-3-methoxypyridin-2-yl)amino]-N-($^2$H$_3$)methylpyridazine-3-carboxamide, 6-(2-cyclopropylacetamido)-4-({4-[5-(dimethylcarbamoyl)pyrazin-2-yl]-3-methoxypyridin-2-yl} amino)-N-($^2$H$_3$)methylpyridazine-3-carboxamide, 89

4-({4-[5-(dimethyl carbamoyl)pyrazin-2-yl]-3-methoxypyridin-2-yl} amino)-N-($^2$H$_3$)methyl-6-[(1-methyl-1H-pyrazol-3-yl)amino]pyridazine-3-carboxamide, 6-[(1,5-dimethyl-1H-pyrazol-3-yl)amino]-4-({4-[5-(dimethylcarbamoyl)pyrazin-2-yl]-3-methoxypyridin-2-yl} amino)-N-($^2$H$_3$)methylpyridazine-3-carboxamide, 6-[(5-chloro-1-methyl-1H-pyrazol-3-yl)amino]-4-({4-[5-(dimethylcarbamoyl)pyrazin-2-yl]-3-methoxypyridin-2-yl}amino)-N-($^2$H$_3$)methylpyridazine-3-carboxamide, 4-{[4-(5-fluoropyrimidin-2-yl)-3-methoxypyridin-2-yl] amino}-6-{[5-(2-hydroxypropan-2-yl)pyridin-2-yl] amino}-N-($^2$H$_3$)methylpyridazine-3-carboxamide, 6-{[5-(2-aminopropan-2-yl)pyridin-2-yl]amino}-4-{[4-(5-fluoropyrimidin-2-yl)-3-methoxypyridin-2-yl] amino}-N-($^2$H$_3$)methylpyridazine-3-carboxamide, 4-{[4-(5-fluoropyrimidin-2-yl)-3-methoxypyridin-2-yl] amino}—N-($^2$H$_3$)methyl-6-[(5-methylpyrazin-2-yl) amino]pyridazine-3-carboxamide, 6-[(6-ethoxypyridazin-3-yl)amino]-4-{[4-(5-fluoropyrimidin-2-yl)-3-methoxypyridin-2-yl]amino}-N-($^2$H$_3$) methylpyridazine-3-carboxamide, 4-{[4-(5-fluoropyrimidin-2-yl)-3-methoxypyridin-2-yl] amino}—N-($^2$H$_3$)methyl-6-{[5-(morpholin-4-yl)pyridin-2-yl]amino}pyridazine-3-carboxamide, 6-[(4-fluoropyridin-2-yl)amino]-4-{[4-(5-fluoropyrimidin-2-yl)-3-methoxypyridin-2-yl]amino}-N-($^2$H$_3$) methylpyridazine-3-carboxamide, 4-{[4-(5-fluoropyrimidin-2-yl)-3-methoxypyridin-2-yl] amino}—N-($^2$H$_3$)methyl-6-[(4-methylpyridin-2-yl) amino]pyridazine-3-carboxamide, 4-{[4-(5-fluoropyrimidin-2-yl)-3-methoxypyridin-2-yl]amino}-6-[(6-methoxypyridazin-3-yl)amino]-N-($^2$H$_3$)methylpyridazine-3-carboxamide, 4-{[4-(5-fluoropyrimidin-2-yl)-3-methoxypyridin-2-yl]amino}-N-($^2$H$_3$)methyl-6-[(pyridin-2-yl)amino]pyridazine-3-carboxamide, 6-cyclopropaneamido-4-{[4-(5-fluoropyrimidin-2-yl)-3-methoxypyridin-2-yl] amino}—N-($^2$H$_3$)methylpyridazine-3-carboxamide, or a stereoisomer or pharmaceutically acceptable salt thereof.

10. A pharmaceutical composition comprising one or more compounds according to claim 1, and a pharmaceutically acceptable carrier or diluent.

11. A method of treating a disease, comprising administering to a patient in need of such treatment a therapeutically-effective amount of a compound according to claim 1, wherein the disease is an inflammatory or autoimmune disease selected from the group consisting of multiple sclerosis, rheumatoid arthritis, ankylosing spondylitis, inflammatory bowel disease, systemic lupus erythematosus, psoriasis, psoriatic arthritis, Crohn's Disease, Sjögren's syndrome or scleroderma.

* * * * *

UNITED STATES PATENT AND TRADEMARK OFFICE
CERTIFICATE OF CORRECTION

PATENT NO. : 11,597,721 B2
APPLICATION NO. : 16/982937
DATED : March 7, 2023
INVENTOR(S) : Zili Xiao et al.

It is certified that error appears in the above-identified patent and that said Letters Patent is hereby corrected as shown below:

In the Claims

Column 136, Claim 1, Line 39-40, delete "$(CH_2)_rNR^{11}R^{11}$," and insert -- —$(CH_2)_rNR^{11}R^{11}$, --.

Column 136, Claim 1, Line 40, delete "—$(CH_2)_rNR^bC(O)$" and insert -- —$(CH_2)_rNR^bC(O)R^c$, --.

Column 136, Claim 1, Line 41, delete "$(CH_2)_rNR^bC(O)OR^c$," and insert -- —$(CH_2)_rNR^bC(O)OR^c$, --.

Column 136, Claim 1, Line 42, delete "—$NR_bS(O)_pR^c$, — $S(O)_pR^c$," and insert -- —$NR^bS(O)_pR^c$, —$S(O)_pR^c$, --.

Column 136, Claim 1, Line 48, delete "$C_1$-3" and insert -- $C_{1-3}$ --.

Column 136, Claim 1, Line 48, delete "$C_3$-6" and insert -- $C_{3-6}$ --.

Column 136, Claim 1, Line 49, delete "$C_1$-3" and insert -- $C_{1-3}$ --.

Column 136, Claim 1, Line 49, delete "$C_3$-6" and insert -- $C_{3-6}$ --.

Column 136, Claim 1, Line 50, delete "$C_1$-4" and insert -- $C_{1-4}$ --.

Column 136, Claim 1, Line 52, delete "0-3$R^{5a}$" and insert -- 0-3 $R^{5a}$ --.

Column 136, Claim 1, Line 55, delete "is is" and insert -- is --.

Column 136, Claim 1, Line 59, delete "$C_1$-4" and insert -- $C_{1-4}$ --.

Column 137, Claim 1, Line 1, delete "$C_1$-4" and insert -- $C_{1-4}$ --.

Column 137, Claim 1, Line 10, delete "$(CH_2)_rC(O)NR^{11}R^{11}$," and insert -- —$(CH_2)_rC(O)NR^{11}R^{11}$, --.

Signed and Sealed this
Sixth Day of February, 2024

Katherine Kelly Vidal
*Director of the United States Patent and Trademark Office*

CERTIFICATE OF CORRECTION (continued)

Column 138, Claim 2, Line 11, delete "$C_1$-4" and insert -- $C_{1-4}$ --.

Column 138, Claim 2, Line 16, delete "is is" and insert -- is --.

Column 138, Claim 2, Line 38, delete "$(CH_2)_rC(O)NR^{11}R^{11}$," and insert -- —$(CH_2)_rC(O)NR^{11}R^{11}$, --.

Column 138, Claim 2, Line 40, delete "$S(O)_pNR^{11}R^{11}$," and insert -- —$S(O)_pNR^{11}R^{11}$, --.

Column 138, Claim 2, Line 56, after "$NO_2$," insert -- —$OR^e$, --.

Column 139, Claim 3, Line 42, delete "is is" and insert -- is --.

Column 139, Claim 3, Line 64, delete "$(CH_2)_rC(O)NR^{11}R^{11}$," and insert -- —$(CH_2)_rC(O)NR^{11}R^{11}$, --.

Column 139, Claim 3, Line 66, delete "$S(O)_pNR^{11}R^{11}$," and insert -- —$S(O)_pNR^{11}R^{11}$, --.

Column 140, Claim 3, Line 15 (Approx.), after "$NO_2$," insert -- —$OR^e$, --.

Columns 140-141, Claim 4, Lines 62-67 (Column 140) - Lines 1-4 (Column 141), below "with 0-2 $R^a$;" delete "$R^3$ is H, $C_{1-3}$ alkyl or $C_{3-6}$ cycloalkyl; $R^5$ is $C_{1-4}$ alkyl substituted with 0-1 $R^{5a}$, $C_{1-4}$ alkoxy substituted with 0-1 $R^{5a}$, $(CH_2)_r$-phenyl substituted with 0-3 $R^{5a}$ or a —$(CH_2)$-5-7 membered heterocycle containing 1-4 heteroatoms selected from N, O, and $S(O)_p$; $R^{5a}$ is is independently at each occurrence, H, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl or $(CH_2)_r$-phenyl substituted with 0-3 $R^f$;".

Column 141, Claim 4, Line 30, delete "$(CH_2)_rC(O)NR^{11}R^{11}$," and insert -- —$(CH_2)_rC(O)NR^{11}R^{11}$, --.

Column 141, Claim 4, Line 32, delete "$S(O)_pNR^{11}R^{11}$," and insert -- —$S(O)_pNR^{11}R^{11}$, --.

Column 141, Claim 4, Line 52, after "$NO_2$," insert -- —$OR^e$, --.

Column 142, Claim 5, Lines 2-15 (Approx.), delete " 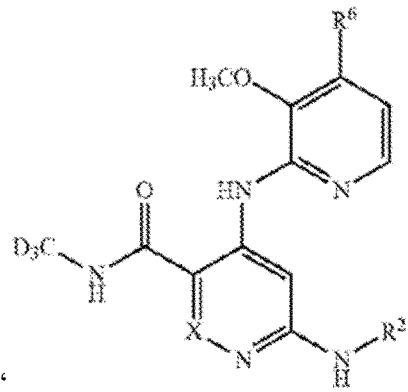 " and insert

CERTIFICATE OF CORRECTION (continued)
U.S. Pat. No. 11,597,721 B2

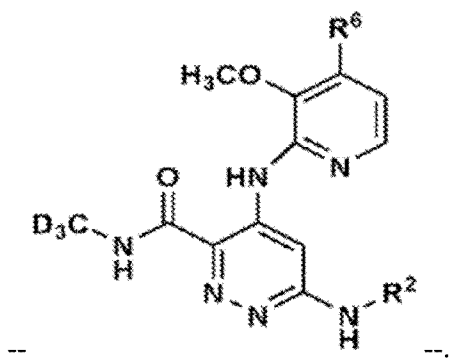
--.

Column 142, Claim 5, Line 20, delete "$R^2a$;" and insert -- $R^{2a}$; --.

Column 142, Claim 5, Lines 51-52, delete "—$NR_bS(O)_pR^c$," and insert -- —$NR^bS(O)_pR^c$, --.

Column 142, Claim 5, Line 63, delete "$R^{e''}$" and insert -- $R^c$ --.

Column 142, Claim 5, Line 67, delete "—$(CH_2)_rC(O)R^e$," and insert -- —$(CH_2)_rC(O)R^c$, --.

Column 143, Claim 5, Line 1, delete "—$NR^eC(O)OR^e$," and insert -- —$NR^eC(O)OR^c$, --.

Column 143, Claim 6, Lines 16-29 (Approx.), delete " 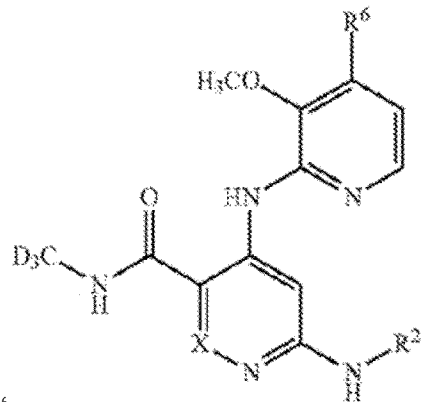 " and insert -- 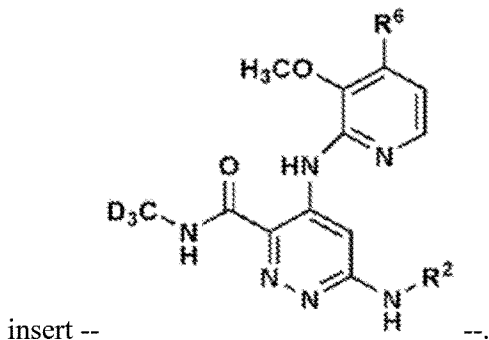 --.

Column 143, Claim 6, Line 39, delete "—$NR^bC(o)NR^{11}R^{11}$," and insert -- —$NR^bC(O)NR^{11}R^{11}$, --.

Column 143, Claim 6, Line 62, delete "$C_1$," and insert -- Cl, --.

Column 143, Claim 6, Lines 66-67, delete "—(CH$_2$)$_r$NR$^b$C(O)O)R$^c$," and insert -- —(CH$_2$)$_r$NR$^b$C(O)R$^c$, --.

Column 144, Claim 6, Line 1, delete "—S(O)R$^c$," and insert -- —S(O)$_2$R$^c$, --.

Column 144, Claim 7, Line 54, delete "—(CH$_2$)$_r$NR$^b$C(O)R$^e$," and insert -- —(CH$_2$)$_r$NR$^b$C(O)R$^c$, --.

Column 144, Claim 7, Line 55, delete "—S(O)$_p$NR$^{11}$R$^{11}$)," and insert -- —S(O)$_p$NR$^{11}$R$^{11}$, --.

Column 144, Claim 7, Line 55, after "—NR$^b$S(O)$_p$R$^c$," insert -- —S(O)$_p$R$^c$, --.

Column 146, Claim 8, Line 40, delete "R$^e$" and insert -- R$^c$ --.

Column 146, Claim 8, Line 44, delete "—(CH$_2$)$_r$C(O)R$^e$," and insert -- —(CH$_2$)$_r$C(O)R$^c$, --.

Column 146, Claim 8, Line 45, delete "—NR$^e$C(O)OR$^e$," and insert -- —NR$^e$C(O)OR$^c$, --.

Column 147, Claim 9, Line 2, delete "-6]2-" and insert -- -6-[2- --.

Column 147, Claim 9, Line 47, delete "-yl]amino} pyridazine" and insert -- -yl]amino}pyridazine --.

Column 148, Claim 9, Lines 7-8, delete "-2H41,3 '-bipyridine]-6'-yl] amino 1 pyridazine-" and insert -- -2H-[1,3'-bipyridine]-6'-yl]amino} pyridazine- --.

Column 148, Claim 9, Line 17, delete "yl] amino 1" and insert -- yl]amino} --.

Column 148, Claim 9, Line 21, delete "yl] amino 1" and insert -- yl]amino} --.

Column 148, Claim 9, Line 32 (Approx.), delete "yl] amino 1" and insert -- yl]amino} --.

Column 148, Claim 9, Line 35, delete "yl] amino 1" and insert -- yl]amino} --.

Column 148, Claim 9, Line 41, delete "yl] amino 1" and insert -- yl]amino} --.

Column 148, Claim 9, Line 43, delete "6-{[5-[3-" and insert -- 6-{[5-(3- --.

Column 148, Claim 9, Line 45, delete "yl]amino 1" and insert -- yl]amino} --.

Column 148, Claim 9, Line 46, delete "carb oxamide," and insert -- carboxamide, --.

Column 148, Claim 9, Line 51, delete "yl] amino 1" and insert -- yl]amino} --.

Column 148, Claim 9, Line 56, below "carboxamide," insert -- 4-[(3-methoxy-4-{5-[(morpholin-4-yl)methyl]-1,2,4-oxadiazol-3-yl}pyridin-2-yl)amino]-N-($^2$H$_3$)methyl-6-[(4-methylpyridin-2-yl)amino]pyridazine-3-carboxamide, --.

CERTIFICATE OF CORRECTION (continued)
U.S. Pat. No. 11,597,721 B2

Column 149, Claim 9, Line 11 (Approx.), delete "{5-[(1 S)-1" and insert -- {5-[(1S)-1 --.

Column 149, Claim 9, Line 32, delete "-6-(4-" and insert -- -6-((4- --.

Column 149, Claim 9, Line 34, delete "N-{5-[(44 5-" and insert -- N-{5-[(4-{5- --.

Column 149, Claim 9, Line 54, delete "4-((3-" and insert -- 4-[(3- --.

Column 150, Claim 9, Line 3, delete "carboxamide" and insert -- carboxamide, --.

Column 150, Claim 9, Line 7, delete "4-(}3-" and insert -- 4-({3- --.

Column 150, Claim 9, Line 13, delete "4-[3-" and insert -- 4-{[3- --.

Column 150, Claim 9, Line 16, delete "4-[3-" and insert -- 4-{[3- --.

Column 150, Claim 9, Line 19, delete "6-[4-" and insert -- 6-{[4- --.

Column 150, Claim 9, Line 22, delete "4-[3-" and insert -- 4-{[3- --.

Column 150, Claim 9, Line 25, delete "6-[5-" and insert -- 6-{[5- --.

Column 150, Claim 9, Line 27, delete "carboxamide" and insert -- carboxamide, --.

Column 150, Claim 9, Line 28, below "carboxamide" insert -- 6-cyclopropaneamido-4-({3'-methoxy-[2,4'-bipyridine]-2'-yl}amino)-N-($^{2}H_{3}$)methylpyridazine-3-carboxamide, --.

Column 150, Claim 9, Line 37, delete "4-(}4-" and insert -- 4-({4- --.

Column 151, Claim 10, Line 13, delete "claim 1," and insert -- claim 1 --.